US010072070B2

United States Patent
Wan et al.

(10) Patent No.: US 10,072,070 B2
(45) Date of Patent: Sep. 11, 2018

(54) POTENT ANTI-INFLUENZA A NEURAMINIDASE SUBTYPE N1 ANTIBODY

(71) Applicant: THE UNITED STATES OF AMERICA, as represented by the Secretary, Department of Health and Human Services, Washington, DC (US)

(72) Inventors: Hongquan Wan, Rockville, MD (US); Maryna C. Eichelberger, Silver Spring, MD (US); Hua Yang, City Johns Creek, GA (US); James Stevens, Lilburn, GA (US); David A. Shore, Decatur, GA (US); Rebecca J. Garten, Decatur, GA (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 15/532,059

(22) PCT Filed: Dec. 3, 2015

(86) PCT No.: PCT/US2015/063799
§ 371 (c)(1),
(2) Date: May 31, 2017

(87) PCT Pub. No.: WO2016/090170
PCT Pub. Date: Jun. 9, 2016

(65) Prior Publication Data
US 2017/0306002 A1    Oct. 26, 2017

Related U.S. Application Data

(60) Provisional application No. 62/088,388, filed on Dec. 5, 2014.

(51) Int. Cl.
*C07K 16/10* (2006.01)
*G01N 33/68* (2006.01)
*G01N 33/573* (2006.01)
*G01N 33/569* (2006.01)
*A61K 45/06* (2006.01)
*A61K 39/42* (2006.01)
*C07K 16/40* (2006.01)
*A61K 39/00* (2006.01)

(52) U.S. Cl.
CPC .......... *C07K 16/1018* (2013.01); *A61K 39/42* (2013.01); *A61K 45/06* (2013.01); *C07K 16/40* (2013.01); *C12Y 302/01018* (2013.01); *G01N 33/56983* (2013.01); *G01N 33/573* (2013.01); *G01N 33/6878* (2013.01); *A61K 2039/505* (2013.01); *A61K 2039/507* (2013.01); *C07K 2317/24* (2013.01); *C07K 2317/54* (2013.01); *C07K 2317/56* (2013.01); *C07K 2317/565* (2013.01); *C07K 2317/76* (2013.01); *G01N 2333/11* (2013.01); *G01N 2333/924* (2013.01); *G01N 2469/10* (2013.01)

(58) Field of Classification Search
CPC ................ C07K 16/1018; C07K 16/40; C07K 2317/565; C07K 2317/76; C07K 2317/54; C07K 2317/24; C07K 2317/56; G01N 33/6878; G01N 33/573; G01N 33/56983; G01N 2333/11; G01N 2333/924; G01N 2469/10; A61K 45/06; A61K 39/42; A61K 2039/507; A61K 2039/505; C12Y 302/01018
See application file for complete search history.

(56) References Cited

FOREIGN PATENT DOCUMENTS

WO    WO 2010/037046 A1    4/2010

OTHER PUBLICATIONS

Sela-Culang I, Kunik V, Ofran Y. The structural basis of antibody-antigen recognition. Front Immunol. Oct. 8, 2013;4:302.*
Cardoso et al., "Single-domain antibodies targeting neuraminidase protect against an H5N1 influenza virus challenge," *Journal of Virology* 88(15): 8278-8296 (Aug. 1, 2014).
Couzens et al., "An optimized enzyme-linked lectin assay to measure influenza A virus neuraminidase inhibition antibody titers in human sera," *Journal of Virological Methods* 210: 7-14 (Dec. 1, 2014).
Doyle et al., "The universal epitope of influenza a viral neuraminidase fundamentally contributes to enzyme activity and viral replication," *Journal of Biological Chemistry* 288(25): 18283-18289 (Epub May 3, 2013).
Doyle et al., "Universal anti-neuraminidase antibody inhibiting all influenza," *Antiviral Research* 100(2): 567-574 (Epub Sep. 30, 2013).
International Search Report from parent PCT Application No. PCT/US2015/063799, 7 pages (dated Feb. 25, 2016).
Król et al., "Antivirals—current trends in fighting influenza," *Acta Biochim Pol.* 61(3): 495-504 (Epub Sep. 1, 2014).
Sela-Culang et al., "The structural basis of antibody-antigen recognition," *Frontiers in Immunology* 4(302): 13 pages (Jan. 1, 2013).
Shoji et al., "An influenza N1 neuraminidase-specific monoclonal antibody with broad neuraminidase inhibition activity against H5N1 HPA1 viruses," *Human Vaccines* 7(0): 199-204 (Jan. 2011).
Wan et al., "Molecular basis for broad neuraminidase immunity: conserved epitopes in seasonal and pandemic H1N1 as well as H5N1 influenza viruses," Journal of Virology 87(16): 9290-9300 (Epub Jun. 19, 2013).
Wan et al., "Structural characterization of a protective epitope spanning A(H1N1)pdm09 influenza virus neuraminidase monomers," *Nature Communications* 6(10): 6114-6123 (Feb. 10, 2015).
Written Opinion from parent PCT Application No. PCT/US2015/063799, 11 pages (dated Feb. 25, 2016).

* cited by examiner

Primary Examiner — Rachel B Gill
(74) Attorney, Agent, or Firm — Klarquist Sparkman, LLP

(57) ABSTRACT

Isolated monoclonal antibodies and antigen binding fragments thereof that specifically bind neuraminidase (NA) of an N1 subtype influenza virus are disclosed herein. These antibodies and antigen binding fragments can be used for the detection of an N1 subtype influenza virus and for determining the immunogenicity of vaccines. The antibodies and antigen binding fragments also can be used for the treatment of a subject to prevent or ameliorate an influenza infection.

39 Claims, 25 Drawing Sheets
Specification includes a Sequence Listing.

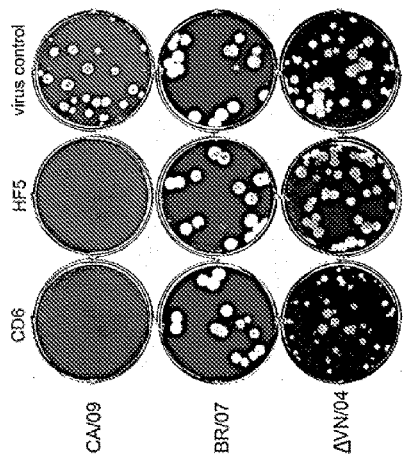
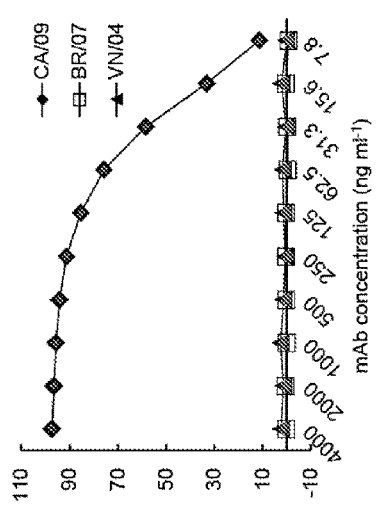
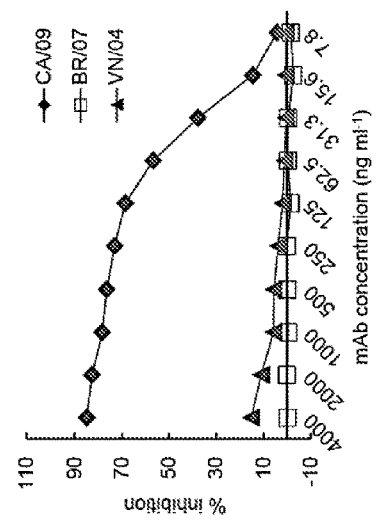
FIG. 1A
FIG. 1B
FIG. 1C

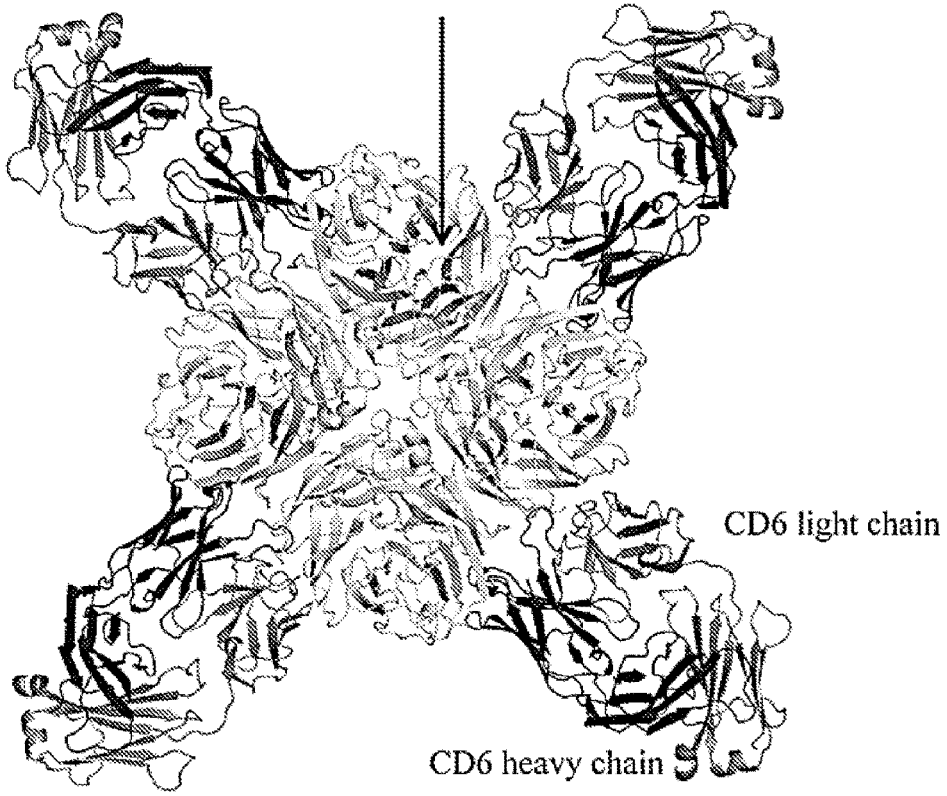

FIG. 3A

NA active site

CD6 light chain

CD6 heavy chain

FIG. 3B

CD6 heavy chain

HCDR1                              HCDR2
QVKLQESGGGLVQPKGSLKLSCAASGFTFNTYAMNWVRQAPGKGLEWVARIRSKSNNYAT

HCDR3
FYADSVKDRFTISRDDSQSMLYLQMHNLKTDDTAMYYCVRPSIYYYASGYLDVWGAGTTVT

VSSA

CD6 light chain

LCDR1                        LCDR2
QIVLSQSPAILSASPGEKVTMTCRTSSSVSYMHWYQQKPGSSPKWIYATSNLASGVPER

LCDR3
FSGSGSGTSYSLTISRVEAEDAATYYCQQWNSNPPTFGGGTKLEIK

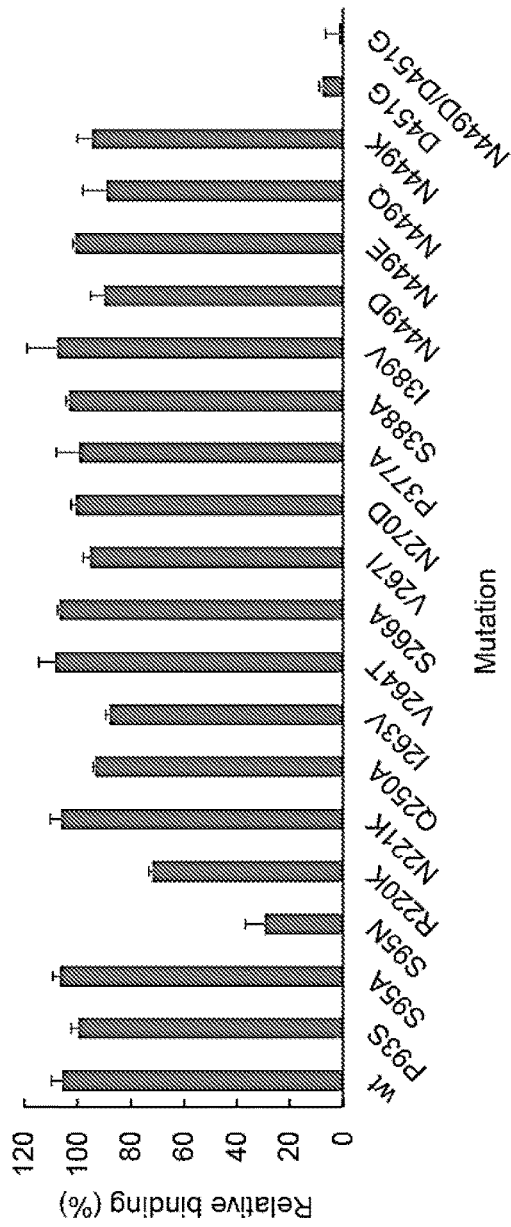
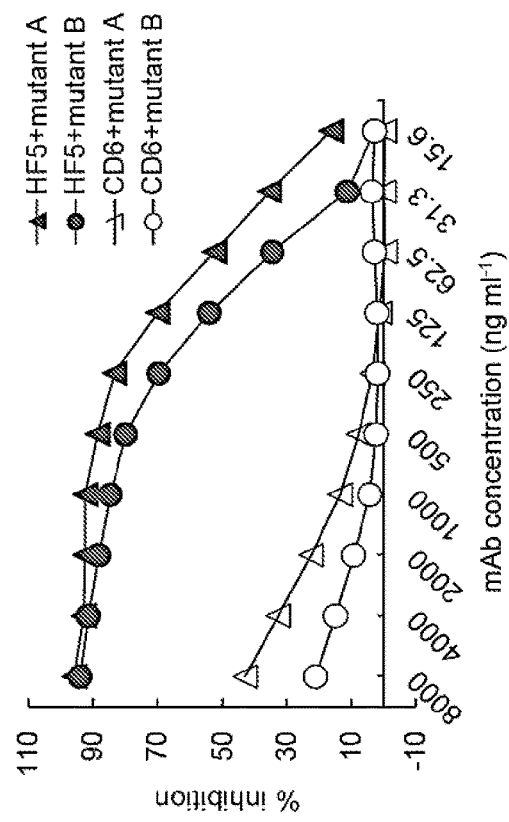
FIG. 5A
FIG. 5B

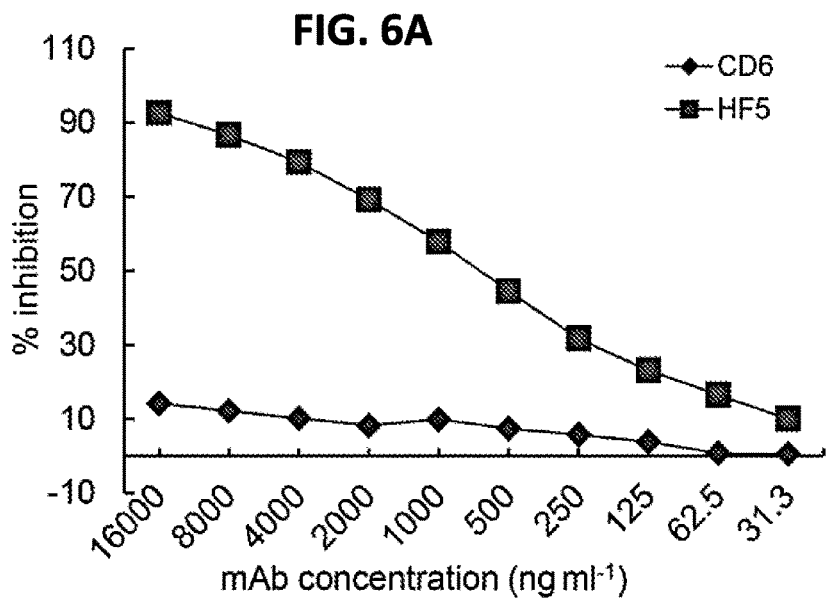
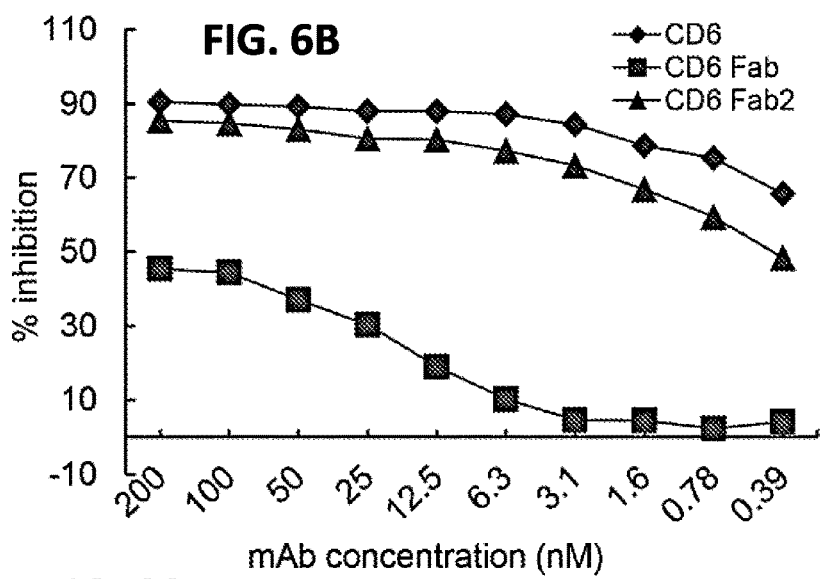
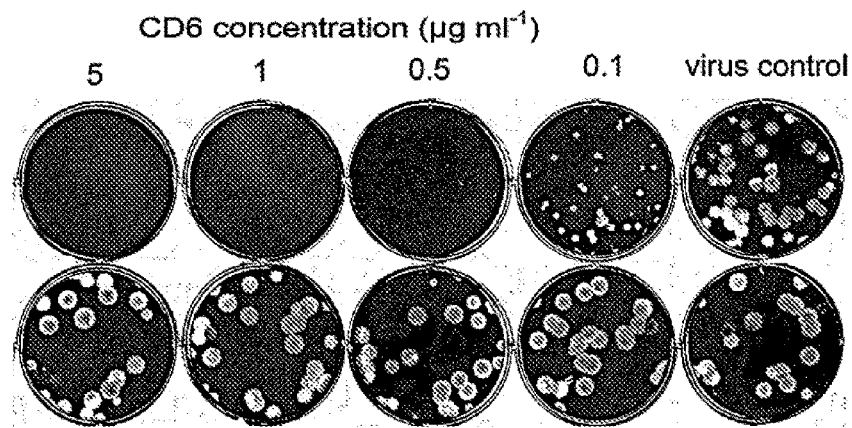

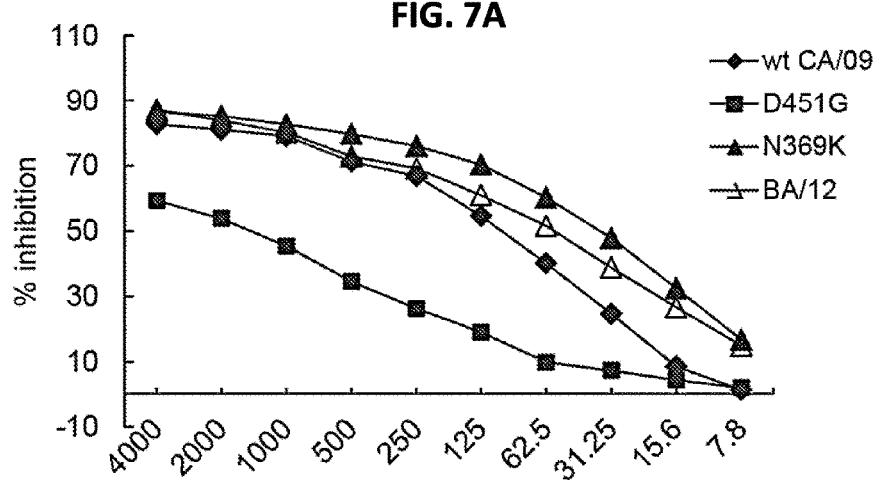
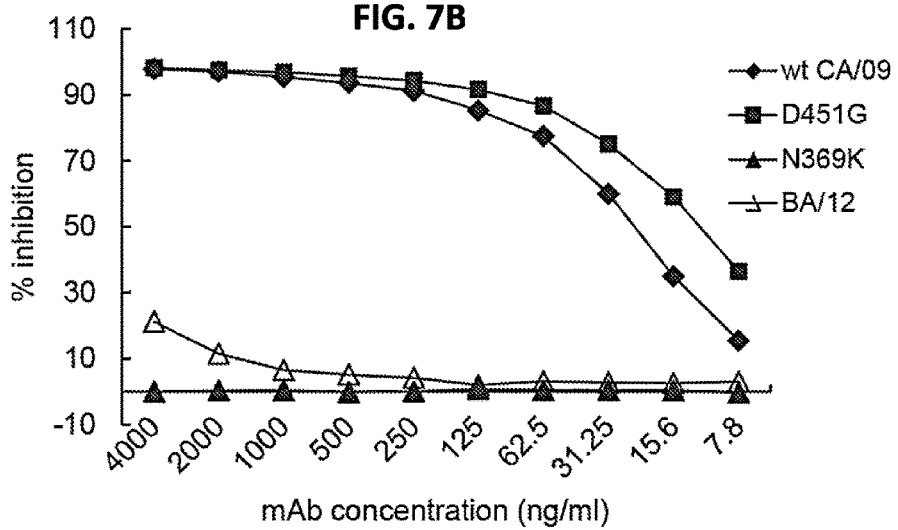

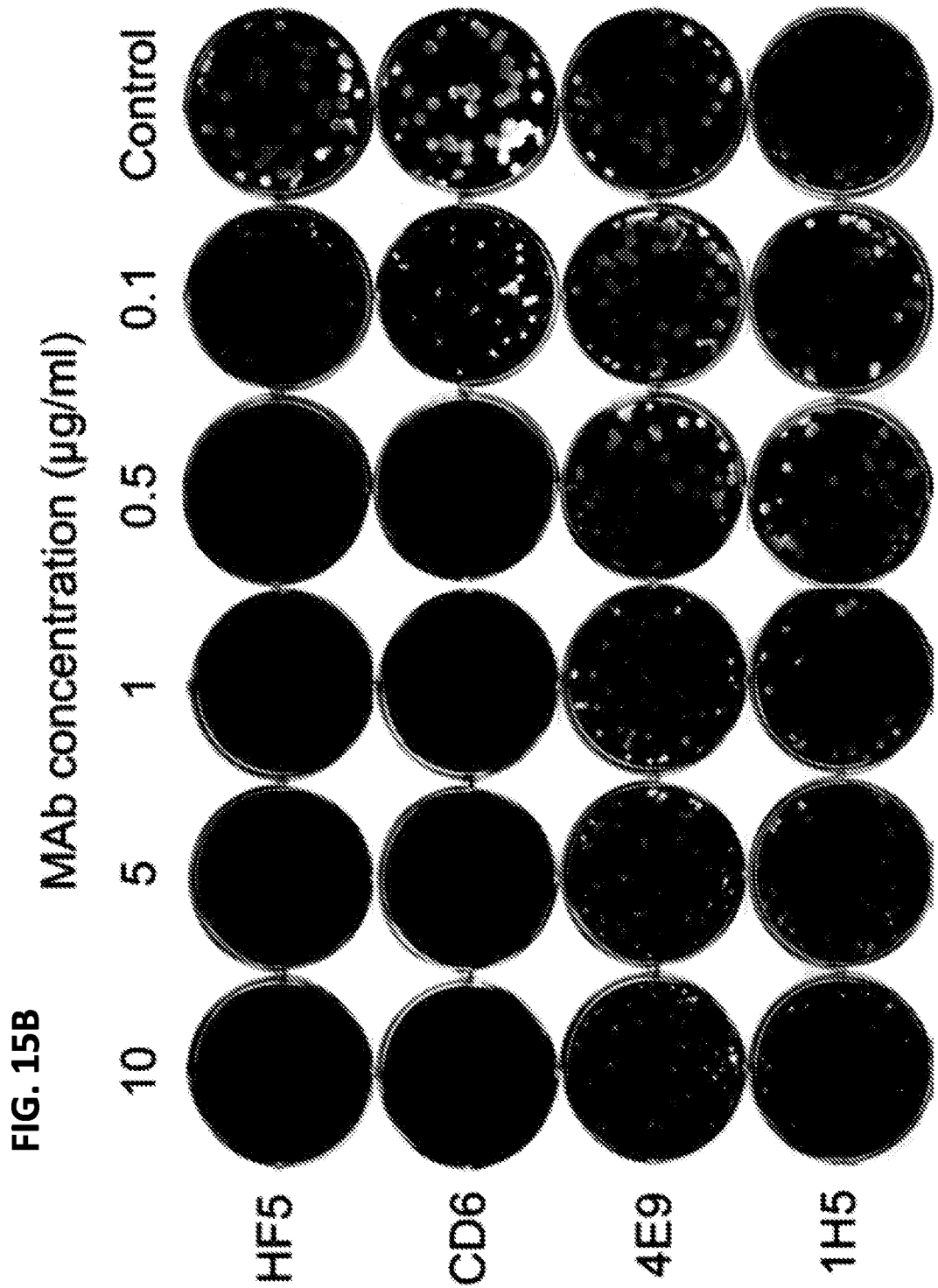

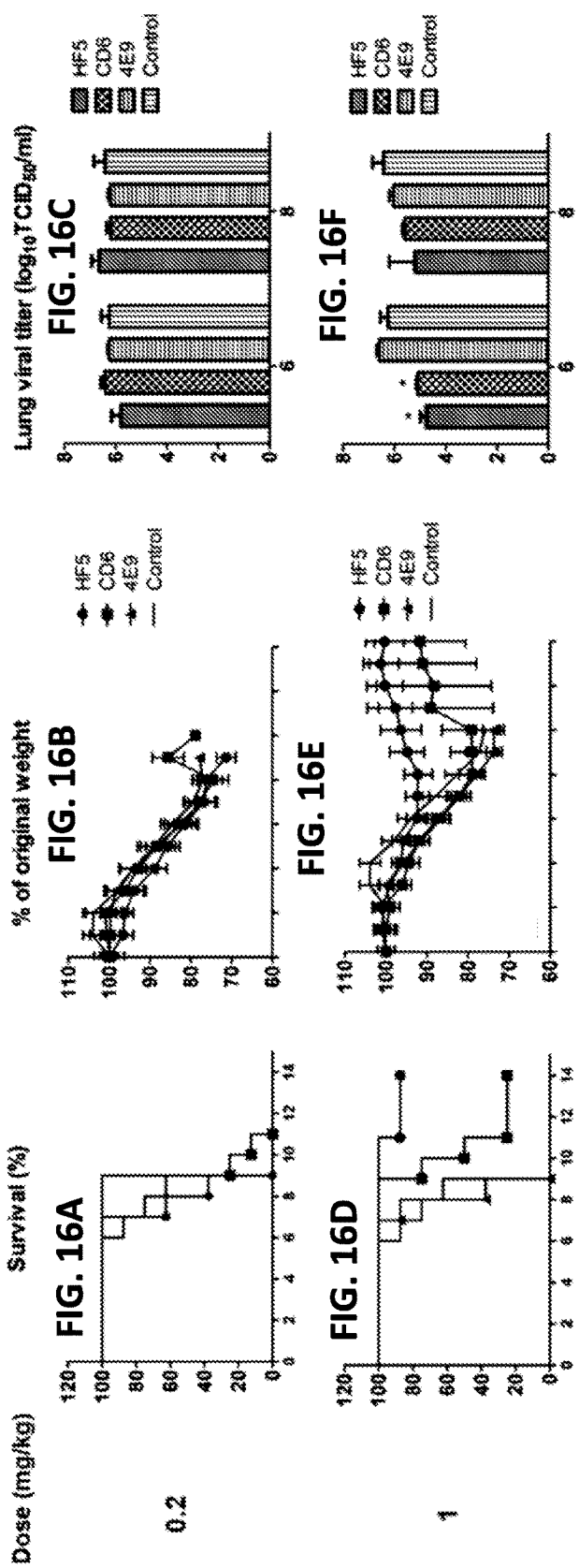

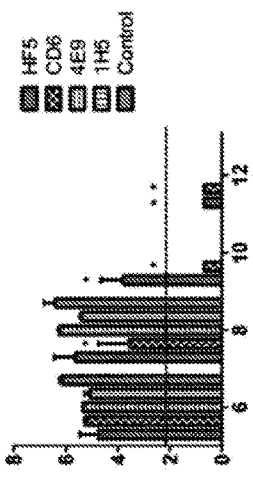
FIG. 16G
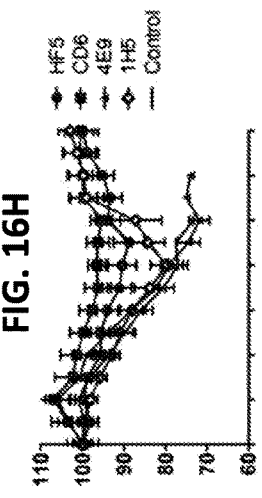
FIG. 16H
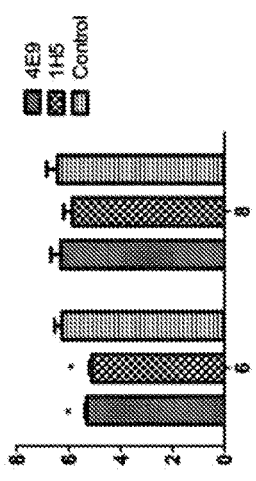
FIG. 16I
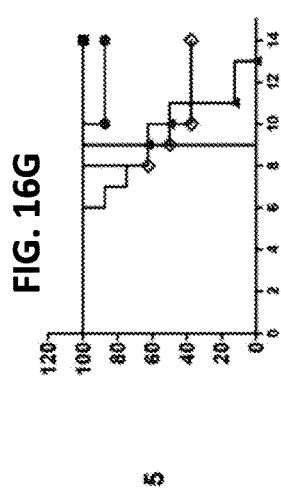
FIG. 16J
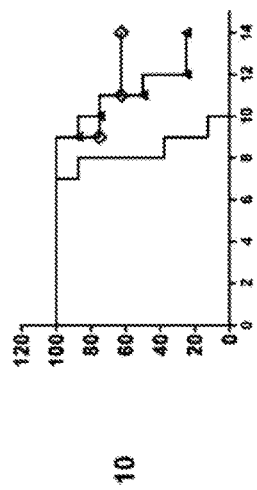
FIG. 16K
FIG. 16L

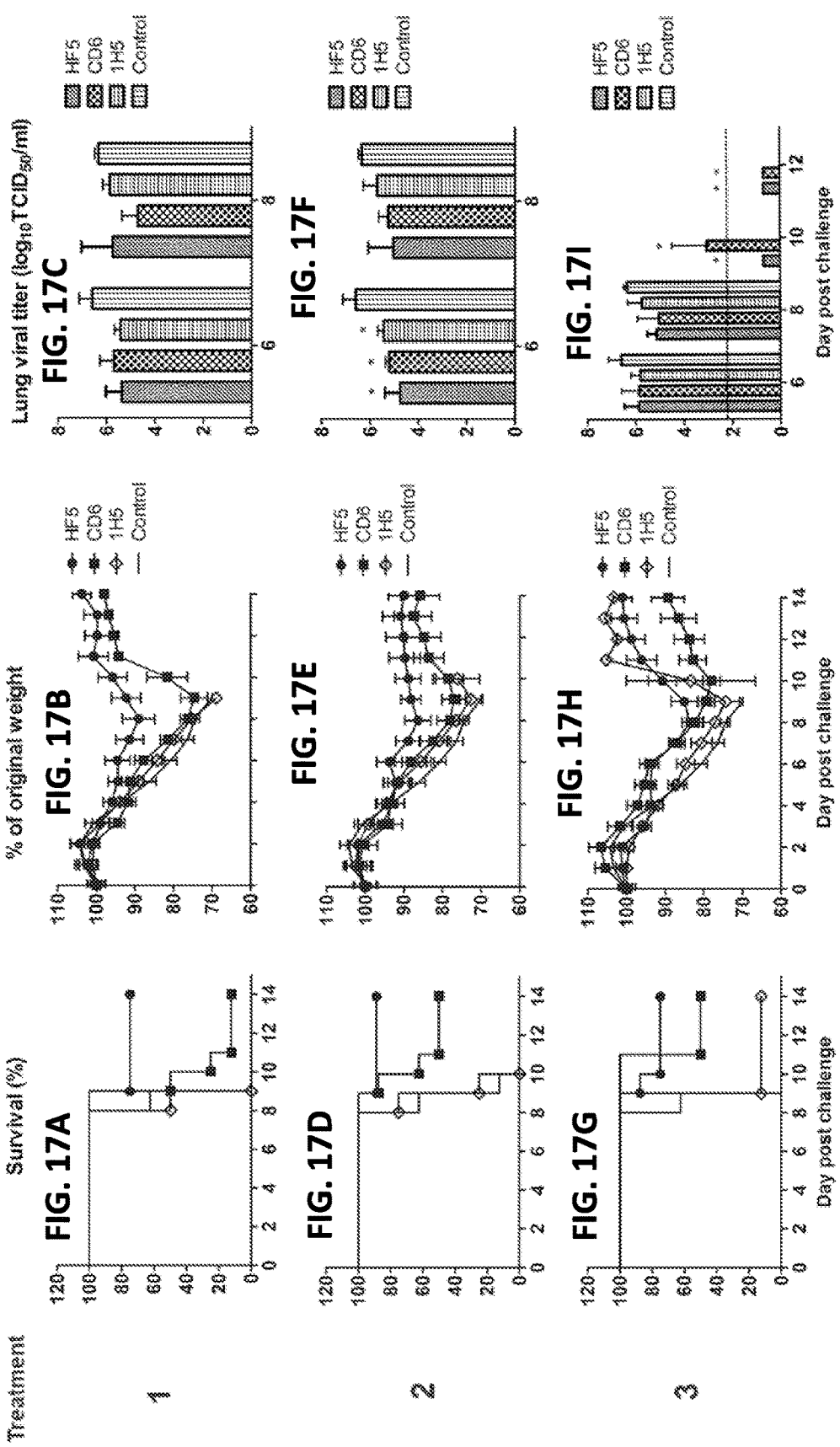

SEQUENCE LISTING

<160> NUMBER OF SEQ ID NOS: 4

<210> SEQ ID NO 1
<211> LENGTH: 454
<212> TYPE: PRT
<213> ORGANISM: Mus musculus

<400> SEQUENCE: 1

```
Gln Val Lys Leu Gln Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Phe Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met His Asn Leu Lys Thr Asp Asp Thr Ala Met Tyr
                85                  90                  95

Tyr Cys Val Arg Pro Ser Ile Tyr Tyr Ala Ser Gly Tyr Leu Asp
            100                 105                 110

Val Trp Gly Ala Gly Thr Thr Val Thr Val Ser Ser Ala Lys Thr Thr
        115                 120                 125

Ala Pro Ser Val Tyr Pro Leu Ala Pro Val Cys Gly Asp Thr Thr Gly
    130                 135                 140

Ser Ser Val Thr Leu Gly Cys Leu Val Lys Gly Tyr Phe Pro Glu Pro
145                 150                 155                 160

Val Thr Leu Thr Trp Asn Ser Gly Ser Leu Ser Ser Gly Val His Thr
                165                 170                 175

Phe Pro Ala Val Leu Gln Ser Asp Leu Tyr Thr Leu Ser Ser Ser Val
            180                 185                 190

Thr Val Thr Ser Ser Thr Trp Pro Ser Gln Ser Ile Thr Cys Asn Val
        195                 200                 205

Ala His Pro Ala Ser Ser Thr Lys Val Asp Lys Lys Ile Glu Pro Arg
    210                 215                 220

Gly Pro Thr Ile Lys Pro Cys Pro Pro Cys Lys Cys Pro Ala Pro Asn
225                 230                 235                 240

Leu Leu Gly Gly Pro Ser Val Phe Ile Phe Pro Pro Lys Ile Lys Asp
                245                 250                 255

Val Leu Met Ile Ser Leu Ser Pro Ile Val Thr Cys Val Val Val Asp
            260                 265                 270

Val Ser Glu Asp Asp Pro Asp Val Gln Ile Ser Trp Phe Val Asn Asn
        275                 280                 285

Val Glu Val His Thr Ala Gln Thr Gln Thr His Arg Glu Asp Tyr Asn
    290                 295                 300
```

```
Ser Thr Leu Arg Val Val Ser Ala Leu Pro Ile Gln His Gln Asp Trp
305                 310                 315                 320

Met Ser Gly Lys Glu Phe Lys Cys Lys Val Asn Asn Lys Asp Leu Thr
            325                 330                 335

Ala Pro Ile Glu Arg Thr Ile Ser Lys Pro Lys Gly Ser Val Arg Ala
            340                 345                 350

Pro Gln Val Tyr Val Leu Pro Pro Glu Glu Met Thr Lys Lys
        355                 360                 365

Gln Val Thr Leu Thr Cys Met Val Thr Asp Phe Met Pro Glu Asp Ile
    370                 375                 380

Tyr Val Glu Trp Thr Asn Asn Gly Lys Thr Glu Leu Asn Tyr Lys Asn
385                 390                 395                 400

Thr Glu Pro Val Leu Asp Ser Asp Gly Ser Tyr Phe Met Tyr Ser Lys
                405                 410                 415

Leu Arg Val Glu Lys Lys Asn Trp Val Glu Arg Asn Ser Tyr Ser Cys
            420                 425                 430

Ser Val Val His Glu Gly Leu His Asn His His Thr Thr Lys Ser Leu
            435                 440                 445

Ala His Ser Pro Gly Lys
    450

<210> SEQ ID NO 2
<211> LENGTH: 213
<212> TYPE: PRT
<213> ORGANISM: Mus musculus

<400> SEQUENCE: 2

Gln Ile Val Leu Ser Gln Ser Pro Ala Ile Leu Ser Ala Ser Pro Gly
1               5                   10                  15

Glu Lys Val Thr Met Thr Cys Arg Thr Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Phe Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Asn Ser Asn Pro Pro Thr
                85                  90                  95

Phe Gly Gly Gly Thr Lys Leu Glu Ile Lys Arg Ala Asp Ala Ala Pro
            100                 105                 110

Thr Val Ser Ile Phe Pro Pro Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210
```

<210> SEQ ID NO 3
<211> LENGTH: 1365
<212> TYPE: DNA
<213> ORGANISM: Mus musculus

<400> SEQUENCE: 3

```
caggttaagc tgcaggagtc tggtggagga ttggtgcagc ctaaagggtc attgaaactc      60
tcatgtgcag cctctggatt cactttcaat acctacgcca tgaactgggt ccgccaggct     120
ccaggaaagg gtttggaatg ggttgctcgc ataagaagta aaagtaataa ttatgcaaca     180
tttatgccg attcagtgaa agacaggttc accatctcca gagatgattc acaaagcatg     240
ctctatctgc aaatgcacaa cttgaaaact gacgacacag ccatgtatta ctgtgtgaga     300
ccctctattt attactacgc tagtggatac ctcgatgtct ggggcgcagg gaccacggtc     360
accgtctcct cagccaaaac aacagcccca tcggtctatc cactggcccc tgtgtgtgga     420
gatacaactg gctcctcggt gactctagga tgcctggtca agggttattt ccctgagcca     480
gtgaccttga cctggaactc tggatccctg tccagtggtg tgcacacctt cccagctgtc     540
ctgcagtctg acctctacac cctcagcagc tcagtgactg taacctcgag cacctggccc     600
agccagtcca tcacctgcaa tgtggcccac ccggcaagca gcaccaaggt ggacaagaaa     660
attgagccca gagggcccac aatcaagccc tgtcctccat gcaaatgccc agcacctaac     720
ctcttgggtg gaccatccgt cttcatcttc cctccaaaga tcaaggatgt actcatgatc     780
tccctgagcc ccatagtcac atgtgtggtg gtggatgtga gcgaggatga cccagatgtc     840
cagatcagct ggtttgtgaa caacgtggaa gtacacacag ctcagacaca aacccataga     900
gaggattaca acagtactct ccgggtggtc agtgccctcc ccatccagca ccaggactgg     960
atgagtggca aggagttcaa atgcaaggtc aacaacaaag acctcacagc gcccatcgag    1020
agaaccatct caaacccaa agggtcagta gagctccac aggtatatgt cttgcctcca    1080
ccagaagaag agatgactaa gaaacaggtc actctgacct gcatggtcac agacttcatg    1140
cctgaagaca tttacgtgga gtggaccaac aacgggaaaa cagagctaaa ctacaagaac    1200
actgaaccag tcctggactc tgatggttct tacttcatgt acagcaagct gagagtggaa    1260
aagaagaact gggtggaaag aaatagctac tcctgttcag tggtccacga gggtctgcac    1320
aatcaccaca cgactaagag cctcgcccac tctcctggta aatga                    1365
```

<210> SEQ ID NO 4
<211> LENGTH: 642
<212> TYPE: DNA
<213> ORGANISM: Mus musculus

<400> SEQUENCE: 4

```
caaattgttc tctcccagtc tccagcaatc ctgtctgcat ctccagggga aaggtcaca      60
atgacttgca ggaccagctc aagtgtaagt tacatgcact ggtaccagca gaagccagga     120
tcctccccca aaccctggat ttatgccaca tccaacctgg cttctggagt ccctttttcgc     180
ttcagtggca gtgggtctgg gacctcttac tctctcacaa tcagcagagt ggaggctgaa     240
gatgctgcca cttattactg ccagcagtgg aatagtaacc cacccacgtt cggaggggggg     300
accaagctgg aaataaaacg ggctgatgct gcaccaactg tatccatctt cccaccatcc     360
agtgagcagt taacatctgg aggtgcctca gtcgtgtgct tcttgaacaa cttctacccc     420
aaagacatca atgtcaagtg gaagattgat ggcagtgaac gacaaaatgg cgtcctgaac     480
```

| | | | | |
|---|---|---|---|---|
| agttggactg | atcaggacag | caaagacagc | acctacagca | tgagcagcac cctcacgttg | 540 |
| accaaggacg | agtatgaacg | acataacagc | tatacctgtg | aggccactca caagacatca | 600 |
| acttcaccca | ttgtcaagag | cttcaacagg | aatgagtgtt | ag | 642 |

POTENT ANTI-INFLUENZA A NEURAMINIDASE SUBTYPE N1 ANTIBODY

CROSS REFERENCE TO RELATED APPLICATION

This is a § 371 U.S. national stage of International Application No. PCT/US2015/063799, filed Dec. 3, 2015, which was published in English under PCT Article 21(2), which claims the benefit of U.S. Provisional Application No. 62/088,388, filed Dec. 5, 2014, which is incorporated herein by reference.

FIELD OF THE DISCLOSURE

This relates to the field of antivirals, specifically to antibodies that specifically bind neuramindase (NA) of an N1 subtype influenza virus.

BACKGROUND

In 2009 a novel swine-origin H1N1 virus emerged in humans, resulting in the first influenza pandemic of the 21$^{st}$ century. This A(H1N1)pdm09 (pH1N1) virus has continued to circulate and was the predominant strain in the USA during the most recent 2013/14 influenza season (CDC. Update: influenza activity-United States, Sep. 29, 2013-Feb. 8, 2014. *MMWR* 63, 148-54 (2014)). Although the overall disease incidence was lower in the 2013/14 winter than during the 2009 outbreak, adults 18-64 years old were at higher risk of severe disease and death when compared to the traditionally highest risk 65+ year age group. This corresponded to a low rate of vaccination in young adults (CDC. FluVaxView. *Centers for Disease Control and Prevention*, available on the internet <cdc.gov/flu/fluvaxview/1314season_htm>. (2014)). Fortunately, most pH1N1 viruses are sensitive to the clinically available NA inhibitors oseltamivir and zanamivir, and therefore patients can be offered treatments early after infection (Moscona, A. *N Engl J Med* 353, 1363-73 (2005)). Oseltamivir is often the treatment of choice because it is available as an oral formulation and therefore easier to administer than inhalation of zanamivir. However, NA inhibitor-resistant influenza viruses can be selected quickly in treated patients (Memoli, M. J. et al. *J Infect Dis* 203, 348-57 (2011)), or can sometimes emerge without an apparent link to treatment (Sheu, T. G. et al. *Antimicrob Agents Chemother* 52, 3284-92 (2008)). Indeed, during the 2013/14 influenza season, oseltamivir-resistant pH1N1 viruses were reported in China, Japan and the USA (WHO. World Health Organization, see the internet at <.who.int/influenza/vaccines/virus/recommendations/2014_15_north/en/> (2014)). The increased pH1N1 influenza activity and the emergence of oseltamivir-resistant pH1N1 viruses add urgency to the need for additional influenza antivirals. It would be advantageous for the new therapeutics to inhibit influenza virus through mechanisms distinct from oseltamivir and zanamivir, to help assure that NA inhibitor-resistant viruses remain sensitive to the new agents.

SUMMARY OF THE DISCLOSURE

Monoclonal antibodies and antigen binding fragments thereof are disclosed herein that specifically bind an epitope bridging neighboring NA monomers of an N1 subtype influenza virus.

Disclosed herein are isolated monoclonal antibodies that include a heavy chain variable domain and a light chain variable domain, wherein the heavy chain variable domain comprises a heavy chain complementarity determining region (HCDR)1, an HCDR2 and an HCDR3, wherein the HCDR1 comprises the amino acid sequence set forth as amino acids 26 to 33 of SEQ ID NO: 1, the HCDR2 comprises the amino acid sequence set forth as amino acids 51 to 60 of SEQ ID NO: 1, and the HCDR3 comprises the amino acid sequence set forth as amino acids 99 to 113 of SEQ ID NO: 1, and wherein the light chain variable domain comprises an LCDR1, an LCDR2 and an LCDR3, and wherein LCDR1 comprises the amino acid sequence set forth as amino acids 27 to 31 of SEQ ID NO: 2, the LCDR2 comprises the amino acid sequence set forth as amino acids 49 to 51 of SEQ ID NO:2, and the LCDR3 comprises the amino acid sequence set forth as amino acids 88 to 96 of SEQ ID NO: 2, wherein the monoclonal antibody specifically binds NA of an N1 subtype influenza virus. In addition, disclosed are the antigen binding fragments of these antibodies. Nucleic acids encoding these antibodies, expression vectors including these nucleic acids, and host cells including these nucleic acids and expression vectors are also disclosed.

In some embodiments, methods are provided for preventing or treating influenza in a subject. These methods include administering to the subject a therapeutically effective amount of a disclosed antibody or antigen binding fragment, or a nucleic acid encoding the antibody or the antigen binding fragment.

In additional embodiments, methods are provided for detecting an influenza virus infection in a subject. The methods include contacting a biological sample from the subject with a disclosed monoclonal antibody or the antigen binding fragment, and detecting antibody bound to the sample. The presence of antibody bound to the sample indicates that the subject has an influenza virus infection.

In other embodiments, methods are provided for identifying a protein as a vaccine candidate. The methods include contacting the protein with a disclosed monoclonal antibody or the antigen binding fragment, under conditions sufficient to form an immune complex, and detecting the presence of an immune complex. The presence of the immune complex indicates that the protein is a vaccine candidate for an influenza virus infection.

In further embodiments, methods are provided for determining the quantity of NA in a sample. The methods include contacting a sample with a disclosed monoclonal antibody or the antigen binding fragment under conditions sufficient to form an immune complex, and quantifying the amount of the immune complex, thereby determining the quantity of NA in the sample.

The foregoing and other features and advantages of the invention will become more apparent from the following detailed description of several embodiments which proceeds with reference to the accompanying figures.

BRIEF DESCRIPTION OF THE FIGURES

FIGS. 1A-1C. mAb CD6 inhibits pH1N1 virus NA activity. Inhibition of N1 enzyme activity by (1A) CD6 and (1B) HF5 measured in ELLA. The assay used fetuin as substrate and H6 reassortant viruses with the NA of CA/09 (pH1N1), BR/07 (seasonal H1N1) and VN/04 (H5N1) as the antigen/ enzyme. (1C) Reduction of influenza virus plaque size by CD6 and HF5. MDCK cells were inoculated with CA/09, BR/07 or ΔVN/04 viruses and incubated for 3 days with an agar overlay containing no mAb (virus control), or 1 μg ml$^{-1}$ of each mAb. Cells were stained with crystal violet to visualize the plaques. The data shown are from a single experiment. These results are representative of three independent assays. Full names of the listed influenza viruses are provided in the Examples section below.

FIGS. 3A-3B. Crystal structure of CD6 Fab in complex with CA/09 NA. (3A) Overall structure of the antibody-antigen complex. Four Fabs bind to the NA tetramer, and each Fab bridges neighboring NA monomers. (3B) Amino acid sequences of the CD6 Fab variable regions. SEQ ID NO: 1 (CD6 heavy chain) and SEQ ID NO: 2 (CD6 light chain) are shown. Residues that are in contact with NA in the complex structure are underlined. The CDR regions shown by a line above the sequence were defined using IMGT/V-QUEST (Brochet, X., Lefranc, M. P. & Giudicelli, V. *Nucleic Acids Res* 36, W503-8 (2008)).

FIGS. 5A-5B. Amino acids in CA/09 NA critical for CD6 binding. (5A) Binding of antibody CD6 to CA/09 NA mutants transiently expressed on 293T cells. ELISA signals generated with CD6 (1 μg ml$^{-1}$) were normalized to those of mouse serum against CA/09 and were expressed as relative binding. Binding to wt CA/09 NA is shown in the first bar labeled wt. Each bar represents the average+SD of two independent assays performed in duplicate. (5B) Inhibition of NA activity of two representative escape variants (mutant A and mutant B) selected in the presence of mAb CD6. The inhibition was measured with ELLA. The data shown are from one of three independent assays that gave similar results.

FIGS. 6A-6C. CD6 inhibits NA activity by blocking the access of substrate to the enzyme active site. (6A) Inhibition of CA/09 NA cleavage of a small substrate MU-NANA (MW: 489 D) by mAbs CD6 and HF5. (6B) Inhibition of CA/09 NA cleavage of a large substrate fetuin (MW: 49 kD) by CD6 whole IgG, Fab2 and Fab. Data in (6A) and (6B) are representative of three independent assays. The ability of the CD6 Fab, Fab2 and whole IgG to bind NA is shown in FIG. 11. (6C) CD6 inhibits CA/09 plaque formation when supplemented in the overlay agar (after virus infection of cells) (upper panel), but does not inhibit plaque formation when supplemented in the virus inoculum (cells were infected with CA/09 virus pre-mixed with CD6 and after thorough washing, the infected cells were covered with agar without antibody) (bottom panel).

FIGS. 7A-7B. NA of genetic group 6A is sensitive to inhibition by CD6. (7A) Inhibition of the NA activity of variant and circulating viruses by mAb CD6. The sensitivity of the NA of the following viruses was tested in ELLA: wt CA/09, CA/09 with single amino acid mutation D451G or N369K in NA; BA/12 (genetic group 6A). BA/12 contains D451G mutation as well as additional mutations at residues 106, 241, 248, 369 and 386 in NA. (7B) Inhibition of the enzyme activity of the NAs described in (7A) by mAb HF5. The data shown are from a single assay; the results of three independent assays were similar.

FIGS. 15A-15D. Different functional properties of MAbs HF5, CD6, 4E9 and 1H5 in vitro. (15A) Inhibition of CA/09 NA activity by each MAb measured in ELLA using $H6N1_{CA/09}$ and wt CA/09 viruses. (B) CA/09 virus plaques formed in the presence of various concentrations of MAbs HF5, CD6, 4E9 and 1H5 (0.1-10 µg/ml) or the control MAb 3A2 (10 µg/ml) in the overlay agar. (15C) Diameters of CA/09 virus plaques as shown in (15B). Plaques from each treatment were randomly chosen, and the diameters measured and compared to those of the control. Shown are mean diameters (n=20); SD is shown with an error bar. Diameters that are significantly different from the control (p<0.05) are indicated by a line and asterisk (*). (15D) Growth kinetics of CA/09 in MDCK cells in the presence of MAbs HF5, CD6, 4E9, 1H5 or 3A2 (1, 5 or 10 µg/ml). Cells growing in 12-well plates were infected with CA/09 at MOI=0.001, and viral titers in supernatant at indicated time points were measured in plaque assay. Shown are the average titers of duplicate wells; SD is shown with an error bar. *, p<0.05. The asterisks above the CD6 line or below the HF5 line indicates a significant difference between viral titers generated in the presence of the tested MAbs (CD6 or HF5) and the control MAb 3A2, asterisks between the CD6 and HF5 lines indicate significant differences between viral titers generated in the presence of MAbs CD6 and HF5, asterisks below the 4E9 line in the right panel indicate significant differences between 4E9 and 1H5 groups and the control group (3A2).

FIGS. 17A-17I. Therapeutic efficacy of MAbs HF5, CD6 and 1H5 against lethal pH1N1 virus challenge in mice. DBA/2 mice (n=14 or 20 per group) were infected i.n. with 10 $MLD_{50}$ of CA/09, followed by injection i.p. with a single dose of each MAb on day 1 p.c., two doses on days 1 and 5 p.c., or three doses (5 mg/kg per dose) on days 1, 3 and 5 p.c (shown as treatments 1, 2, 3 on the figure, respectively). MAb 3A2, which is specific to the seasonal H1N1 BR/07 virus, was used as a negative control. Survival (panels 17A, 17D and 17G) and weight loss (panels 17B, 17E and 17H) (n=8 per group) were monitored for up to 14 days. Lungs were collected on different days and viral titers (panels 17C, 17F and 17I) were determined by titrating in MDCK cells. Titers are expressed as $\log_{10}$ $TCID_{50}$/ml; SD is shown with an error bar. The dotted line denotes the detection limit 2.2 $\log_{10}$ $TCID_{50}$/ml. A titer of 0.7 $\log_{10}$ $TCID_{50}$/ml was assigned to samples below the detection limit. Viral titers of the control groups at day 8 p.c. were used for analysis of titers measured on days 10 and 12 p.c. because none of the mice in control groups survived at these time points. Significant differences between titers measured in each group and MAb 3A2-treated control groups are shown as *, p<0.05.

SEQUENCE LISTING

Figure 2A:
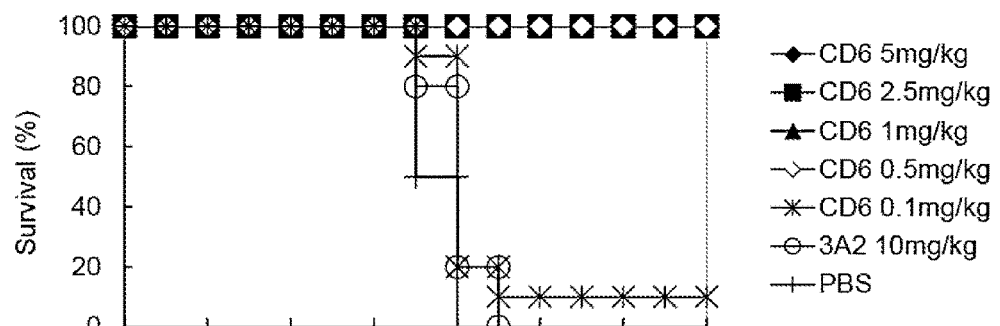
FIGS. 2A-2C. mAb CD6 protects DBA/2 mice against lethal pH1N1 virus challenge. Survival of groups of DBA/2 mice (n=10) treated i.p. with mAb CD6 (2A) prophylactically at 12 h before virus challenge, (2B) therapeutically with a single 5 mg kg$^{-1}$ dose on different days after virus challenge or (2C) therapeutically with either a single dose or sequential doses after virus challenge. mAb 3A2 that is specific to the seasonal H1N1 BR/07 virus was used as a negative control. In all experiments mice were infected intranasally with 10 LD$_{50}$ of CA/09-X179A.
Figure 2B:
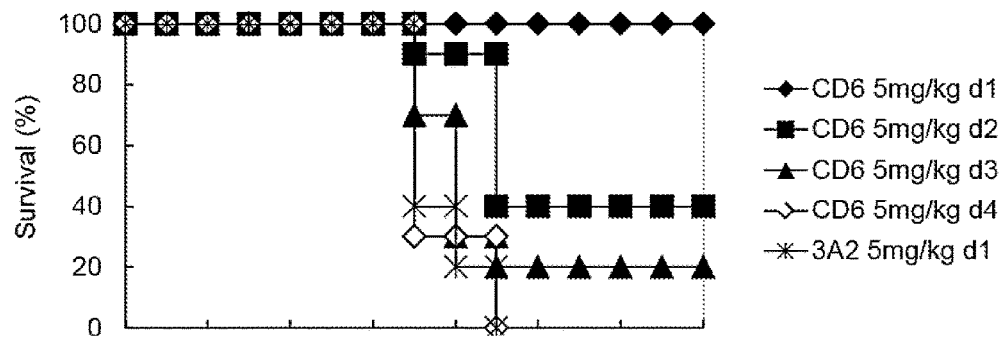
Figure 2C:
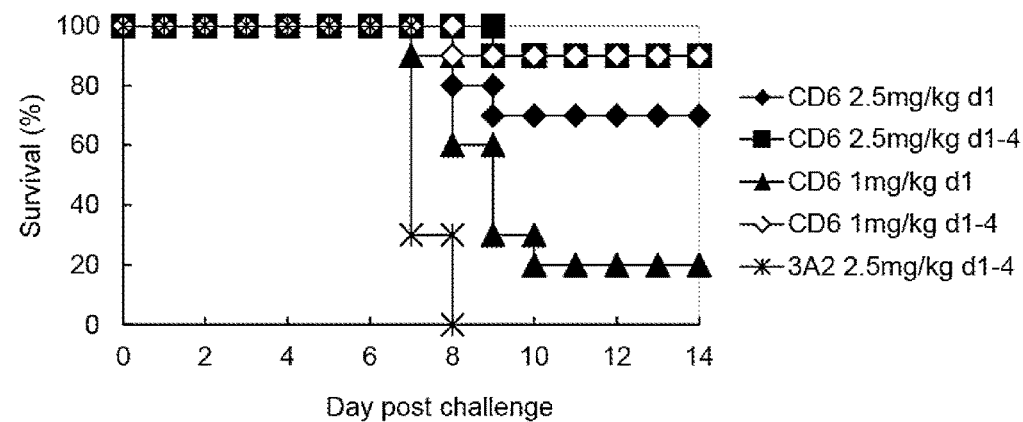

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file Sequence_Listing.txt, May 31, 2017, 8.93 KB, which is incorporated by reference herein. In the accompanying sequence listing:

SEQ ID NO: 1 is the amino acid sequence of the $V_H$ of CD6.

SEQ ID NO: 2 is the amino acid sequence of the $V_L$ of CD6.

SEQ ID NO: 3 is an exemplary nucleic acid sequence encoding the $V_H$ of CD6.

SEQ ID NO: 4 is an exemplary nucleic acid sequence encoding the $V_L$ of CD6.

DETAILED DESCRIPTION OF SEVERAL EMBODIMENTS

Medicinal compounds that are under development to treat an influenza virus infection include agents that target influenza's replication machinery (e.g., favipiravir), destroy the host receptors (e.g. Fludase) (Hayden, F. *Clin Infect Dis* 48 Suppl 1, S3-13 (2009)) or mask host receptors (Connaris, H. et al. *Proc Natl Acad Sci USA* (2014)). Intravenous immunoglobulin (Hung, I. F. et al., *Chest* 144, 464-73 (2013); Kreil, T. R. et al. *Transfusion* 52, 803-9 (2012); Gordon, C. L. et al. *Clin Infect Dis* 52, 422-6 (2011)) and influenza-specific monoclonal antibodies (mAbs) that bind to the conserved, stem region of the hemagglutinin (HA) (Corti, D. et al. *Science* 333, 850-6 (2011); Ekiert, D. C. et al., *Science* 324, 246-51 (2009); Sui, J. et al. *Nat Struct Mol Biol* 16, 265-73 (2009)). The disclosed antibodies reduce virus spread and growth, and protect against a viral infection when administered prophylactically. In addition, the antibodies do not select pH1N1 virus escape mutants.

NA-inhibiting antibodies can have similar effectiveness against influenza as chemical NA inhibitors, such as oseltamivir and zanamivir. Without being bound by theory, since the mechanisms underlying enzyme inhibition are different (oseltamivir and zanamivir bind within the NA active pocket and interrupt the enzyme reaction, while antibodies usually bind to epitopes surrounding the active pocket and inhibit NA activity by restricting access of the natural, large glycoconjugate substrates to the active site), the efficacy of NA-specific antibodies is unlikely to be impacted by changes in sequence that result in oseltamivir or zanamivir resistance. Consequently, NA-specific mAbs, especially those that bind to conserved epitopes, are ideal therapeutic candidates against seasonal and pandemic influenza. Disclosed herein highly potent monoclonal antibodies that specifically bind NA of N1 subtype influenza viruses, such as, but not limited to, A(H1N1)pdm09.

Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). Unless otherwise explained, all technical and scientific terms used herein have the same meaning as commonly understood by one of ordinary skill in the art to which this disclosure belongs.

Adjacent: Molecules that abut one another. Adjacent monomers abut each other in a higher order structure, such as a tetramer.

Amplification: A technique that increases the number of copies of a nucleic acid molecule (such as an RNA or DNA). An example of amplification is the polymerase chain reaction, in which a biological sample is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. The product of amplification can be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in PCT Publication No. WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Animal: Living multi-cellular vertebrate organisms, a category that includes, for example, mammals and birds. The term mammal includes both human and non-human mammals. Similarly, the term "subject" includes both human and veterinary subjects.

Antibody: An immunoglobulin, antigen-binding fragment, or derivative thereof, that specifically binds and recognizes an analyte (antigen) such as neuraminidase (NA), an antigenic fragment thereof, or a dimer or multimer of the antigen. The term "antibody" is used herein in the broadest sense and encompasses various antibody structures, including but not limited to monoclonal antibodies, polyclonal antibodies, multispecific antibodies (e.g., bispecific antibodies), and antigen binding fragments thereof, so long as they exhibit the desired antigen-binding activity. Non-limiting examples of antibodies include, for example, intact immunoglobulins and variants and fragments thereof known in the art that retain binding affinity for the antigen.

A "monoclonal antibody" is an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. The modifier "monoclonal" indicates the character of the antibody as being obtained from a substantially homogeneous population of antibodies, and is not to be construed as requiring production of the antibody by any particular method. In some examples, a monoclonal antibody is an antibody produced by a single clone of B-lymphocytes or by a cell into which nucleic acid encoding the light and heavy variable regions of the antibody of a single antibody (or an antigen binding fragment thereof) have been transfected, or a progeny thereof. In some examples monoclonal antibodies are isolated from a subject. Monoclonal antibodies can have conservative amino acid substitutions which have substantially no effect on antigen binding or other immunoglobulin functions. Exemplary methods of production of monoclonal antibodies are known, for example, see Harlow & Lane, *Antibodies, A Laboratory Manual*, $2^{nd}$ ed. Cold Spring Harbor Publications, New York (2013).)

Typically, an immunoglobulin has heavy (H) chains and light (L) chains interconnected by disulfide bonds Immunoglobulin genes include the kappa, lambda, alpha, gamma, delta, epsilon and mu constant region genes, as well as the myriad immunoglobulin variable domain genes. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region (or constant domain) and a variable region (or variable domain; see, e.g., Kindt et al. Kuby Immunology, 6.sup.th ed., W.H. Freeman and Co., page 91 (2007).) In several embodiments, the heavy and the light chain variable regions combine to specifically bind the antigen. In additional embodiments, only the heavy chain variable region is required. For example, naturally occurring camelid antibodies consisting of a heavy chain only are functional and stable in the absence of light chain (see, e.g., Hamers-Casterman et al., *Nature*, 363:446-448, 1993; Sheriff et al., *Nat. Struct. Biol.*, 3:733-736, 1996). References to "$V_H$" or "VH" refer to the variable region of an antibody heavy chain, including that of an antigen binding fragment, such as Fv, scFv, dsFv or Fab. References to "$V_L$" or "VL" refer to the variable domain of an antibody light chain, including that of an Fv, scFv, dsFv or Fab.

Light and heavy chain variable regions contain a "framework" region interrupted by three hypervariable regions, also called "complementarity-determining regions" or "CDRs" (see, e.g., Kabat et al., *Sequences of Proteins of Immunological Interest*, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. ("Sequences of Proteins of Immunological Interest," 5th Ed. Public Health Service, National Institutes of Health, Bethesda, Md., 1991; "Kabat" numbering scheme), Al-Lazikani et al., (JMB 273, 927-948, 1997; "Chothia" numbering scheme), and Lefranc et al. ("IMGT unique numbering for immunoglobulin and T cell receptor variable domains and Ig superfamily V-like domains," Dev. Comp. Immunol., 27:55-77, 2003; "IMGT" numbering scheme). The CDRs of each chain are typically referred to as CDR1, CDR2, and CDR3 (from the N-terminus to C-terminus), and are also typically identified by the chain in which the particular CDR is located. Thus, a $V_H$ CDR3 is the CDR3 from the variable domain of the heavy chain of the antibody in which it is found, whereas a $V_L$ CDR1 is the CDR1 from the variable domain of the light chain of the antibody in which it is found. Light chain CDRs are sometimes referred to as LCDR1, LCDR2, and LCDR3. Heavy chain CDRs are sometimes referred to as HCDR1, HCDR2, and HCDR3.

An "antigen binding fragment" is a portion of a full length antibody that retains the ability to specifically recognize the cognate antigen, as well as various combinations of such portions. Non-limiting examples of antigen binding fragments include Fv, Fab, Fab', Fab'-SH, F(ab')$_2$; diabodies; linear antibodies; single-chain antibody molecules (e.g. scFv); and multispecific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, $2^{nd}$ Ed., Springer Press, 2010).

A single-chain antibody (scFv) is a genetically engineered molecule containing the $V_H$ and $V_L$ domains of one or more antibody(ies) linked by a suitable polypeptide linker as a genetically fused single chain molecule (see, for example, Bird et al., *Science*, 242:423-426, 1988; Huston et al., *Proc. Natl. Acad. Sci.*, 85:5879-5883, 1988; Ahmad et al., *Clin. Dev. Immunol.*, 2012, doi:10.1155/2012/980250; Marbry, *IDrugs*, 13:543-549, 2010). The intramolecular orientation of the $V_H$-domain and the $V_L$-domain in a scFv, is typically not decisive for scFvs. Thus, scFvs with both possible arrangements ($V_H$-domain-linker domain-$V_L$-domain; $V_L$-domain-linker domain-$V_H$-domain) may be used.

In a disulfide-stabilized variable fragment (dsFv) the heavy and light chain variable chains have been mutated to introduce a disulfide bond to stabilize the association of the chains. Diabodies also are included, which are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., *Proc. Natl. Acad. Sci.*, 90:6444-6448, 1993; Poljak et al., *Structure*, 2:1121-1123, 1994).

Antibodies also include genetically engineered forms such as chimeric antibodies (such as humanized murine antibodies) and heteroconjugate antibodies (such as bispecific antibodies). See also, *Pierce Catalog and Handbook*, 1994-1995 (Pierce Chemical Co., Rockford, Ill.); Kuby, J., Immunology, $3^{rd}$ Ed., W.H. Freeman & Co., New York, 1997.

Non-naturally occurring antibodies can be constructed using solid phase peptide synthesis, can be produced recombinantly, or can be obtained, for example, by screening combinatorial libraries consisting of variable heavy chains and variable light chains as described by Huse et al., Science 246:1275-1281 (1989), which is incorporated herein by reference. These and other methods of making, for example, chimeric, humanized, CDR-grafted, single chain, and bifunctional antibodies, are well known to those skilled in the art (Winter and Harris, Immunol. Today 14:243-246 (1993); Ward et al., Nature 341:544-546 (1989); Harlow and Lane, supra, 1988; Hilyard et al., Protein Engineering: A practical approach (IRL Press 1992); Borrabeck, Antibody Engineering, 2d ed. (Oxford University Press 1995); each of which is incorporated herein by reference).

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. Antibody competition assays are known in the art.

A "humanized" antibody or antigen binding fragment includes a human framework region and one or more CDRs from a non-human (such as a mouse, rat, or synthetic) antibody or antigen binding fragment. The non-human antibody or antigen binding fragment providing the CDRs is termed a "donor," and the human antibody or antigen binding fragment providing the framework is termed an "acceptor." In one embodiment, all the CDRs are from the donor immunoglobulin in a humanized immunoglobulin. Constant regions need not be present, but if they are, they can be substantially identical to human immunoglobulin constant regions, such as at least about 85-90%, such as about 95% or more identical. Hence, all parts of a humanized antibody or antigen binding fragment, except possibly the CDRs, are substantially identical to corresponding parts of natural human antibody sequences.

A "chimeric antibody" is an antibody which includes sequences derived from two different antibodies, which typically are of different species. In some examples, a chimeric antibody includes one or more CDRs and/or framework regions from one human antibody and CDRs and/or framework regions from another human antibody.

A "fully human antibody" or "human antibody" is an antibody which includes sequences from (or derived from) the human genome, and does not include sequence from another species. In some embodiments, a human antibody includes CDRs, framework regions, and (if present) an Fc region from (or derived from) the human genome. Human antibodies can be identified and isolated using technologies for creating antibodies based on sequences derived from the human genome, for example by phage display or using transgenic animals (see, e.g., Barbas et al. *Phage display: A Laboratory Manuel.* 1$^{st}$ Ed. New York: Cold Spring Harbor Laboratory Press, 2004. Print.; Lonberg, Nat. Biotech., 23: 1117-1125, 2005; Lonenberg, Curr. Opin. Immunol., 20:450-459, 2008).

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

Antigen: A compound, composition, or substance that can stimulate the production of antibodies or a T cell response in an animal, including compositions that are injected or absorbed into an animal. An antigen reacts with the products of specific humoral and/or cellular immunity, including those induced by heterologous antigens, such as the disclosed antigens. "Epitope" or "antigenic determinant" refers to the region of an antigen, or an antigen dimer or multimer, to which B and/or T cells respond. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation. Methods of determining spatial conformation of epitopes include, for example, x-ray crystallography and nuclear magnetic resonance.

Examples of antigens include, but are not limited to, peptides, lipids, polysaccharides, and nucleic acids containing antigenic determinants, such as those recognized by an immune cell. In some examples, antigens include peptides derived from a pathogen of interest. Exemplary pathogens include bacteria, fungi, viruses and parasites. In specific examples, an antigen is derived from influenza, such as NA or antigenic fragment thereof.

A "target epitope" is a specific epitope that is specifically bound by an antibody of interest, or an antigen binding fragment thereof. In some examples, a target epitope includes the amino acid residues that contact the antibody of interest, such that the target epitope can be selected by the amino acid residues determined to be in contact with the antibody of interest.

Binding affinity: Affinity of an antibody or antigen binding fragment thereof for an antigen. An antibody specifically binds its target epitope. In one embodiment, affinity is calculated by a modification of the Scatchard method described by Frankel et al., *Mol. Immunol.*, 16:101-106, 1979. In another embodiment, binding affinity is measured by an antigen/antibody dissociation rate. In yet another embodiment, a high binding affinity is measured by a competition radioimmunoassay. In several examples, a high binding affinity is at least about $1 \times 10^{-8}$ M. In other embodiments, a high binding affinity is at least about $1.5 \times 10^{-8}$, at least about $2.0 \times 10^{-8}$, at least about $2.5 \times 10^{-8}$, at least about $3.0 \times 10^{-8}$, at least about $3.5 \times 10^{-8}$, at least about $4.0 \times 10^{-8}$, at least about $4.5 \times 10^{-8}$, or at least about $5.0 \times 10^{-8}$ M.

Biological sample: A sample obtained from a subject. Biological samples include all clinical samples useful for detection of disease or infection (for example, NA) in subjects, including, but not limited to, cells, tissues, and bodily fluids, such as blood, derivatives and fractions of blood (such as serum), cerebrospinal fluid; nasopharyngeal secretions, sputum, as well as biopsied or surgically removed tissue, for example tissues that are unfixed, frozen, or fixed in formalin or paraffin. In some examples, a biological sample is a nasal wash, a lung aspirate, a throat swab, sputum or saliva. In a particular example, a biological sample is obtained from a subject having or suspected of having an influenza virus infection.

Conjugate: A complex of two molecules linked together, for example, linked together by a covalent bond. In one embodiment, an antibody is linked to an effector molecule; for example, an antibody that specifically binds to NA covalently linked to an effector molecule. The linkage can be by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because conjugates can be prepared from two molecules with separate functionalities, such as an antibody and an effector molecule, they are also sometimes referred to as "chimeric molecules."

Contacting: Placement in direct physical association; includes both in solid and liquid form, which can take place either in vivo or in vitro. Contacting includes contact between one molecule and another molecule, for example the amino acid on the surface of one polypeptide, such as an antigen, that contacts another polypeptide, such as an antibody. Thus, contact includes direct or indirect association between atoms that comprise the amino acids from antibody and antigens. Contacting can also include contacting a cell for example by placing an antibody in direct physical association with a cell.

Control: A reference standard. In some embodiments, the control is a negative control, such as sample obtained from a healthy patient not infected with influenza virus or an antibody that does not bind to the targeted antigen. In other embodiments, the control is a positive control, such as a tissue sample obtained from a patient diagnosed with an influenza virus infection, such as an N1 subtype influenza virus infection or a tissue sample from an infected animal that does not receive antibody treatment. In still other embodiments, the control is a historical control or standard reference value or range of values (such as a previously tested control sample, such as a group of patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, or at least about 500%.

Conservative variants: "Conservative" amino acid substitutions are those substitutions that do not substantially alter the biological function of a protein, such as substitutions that do not substantially decrease the binding affinity of an antibody for an antigen (for example, the binding affinity of an antibody for NA). For example, a antibody that specifically binds NA can include at most about 1, at most about 2, at most about 5, at most about 10, or at most about 15 conservative substitutions and specifically bind the NA polypeptide. The term conservative variation also includes the use of a substituted amino acid in place of an unsubstituted parent amino acid, provided that antibody retains binding affinity for NA.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Degenerate variant: In the context of the present disclosure, a "degenerate variant" refers to a polynucleotide encoding a protein (for example, an antibody that specifically binds NA) that includes a sequence that is degenerate as a result of the genetic code. There are twenty natural amino acids, most of which are specified by more than one codon. Therefore, all degenerate nucleotide sequences are included as long as the amino acid sequence of the antibody (or antigen binding fragment) that binds NA encoded by the nucleotide sequence is unchanged.

Detectable marker: A detectable molecule (also known as a label) that is conjugated directly or indirectly to a second molecule, such as an antibody, to facilitate detection of the second molecule. For example, the detectable marker can be capable of detection by ELISA, spectrophotometry, flow cytometry, microscopy or diagnostic imaging techniques (such as CT scans, MRIs, ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionuclides (such as $^{35}S$ or $^{131}I$), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance. Methods for using detectable markers and guidance in the choice of detectable markers appropriate for various purposes are discussed for example in Sambrook et al. (Molecular Cloning: A Laboratory Manual, $4^{th}$ ed, Cold Spring Harbor, N.Y., 2012) and Ausubel et al. (In Current Protocols in Molecular Biology, John Wiley & Sons, New York, through supplement 104, 2013).

Detecting: To identify the existence, presence, or fact of something. General methods of detecting are known to the skilled artisan and may be supplemented with the protocols and reagents disclosed herein. For example, included herein are methods of detecting an N1-containing influenza virus in a biological sample.

Effector molecule: The portion of a chimeric molecule that is intended to have a desired effect on a cell to which the chimeric molecule is targeted. Effector molecule is also known as an effector moiety (EM), therapeutic agent, or diagnostic agent, or similar terms.

Enzyme Linked Immunosorbant Assay (ELISA): An enzyme-linked assay that is a test used to measure binding of an antibody to antigen. There are multiple ways to perform this test; the antigen in the form of whole virus can be immobilized on the surface of wells and the ability of a primary antibody to bind to the antigen measured using a labeled antibody that has specificity for the first antibody.

Alternatively, the antigen can be expressed from cells transfected with recombinant plasmids and the ability of the primary antibody to bind to the antigen determined by binding of a second labeled antibody. Another example of ELISA uses antibody immobilized on the surface of wells to capture the antigen. The amount of antigen captured is determined using a second antigen-specific antibody that is labeled.

Enzyme Linked Lectin Assay (ELLA): A test to measure the ability of an antibody to inhibit neuraminidase activity. In this assay, a NA substrate, fetuin, is immobilized to the surface of wells; neuraminidase is added to the wells in the presence of different concentrations of antibody. Peanut agglutinin (PNA) conjugated to a label such as horse radish peroxidase is then added to the wells. PNA is a lectin that has specificity for a sugar (galactose) that becomes exposed after removal of sialic acid and therefore its ability to bind to molecules in the well indicates how much neuraminidase activity is present. If antibodies inhibit this activity, the signal is in proportion to the amount of antibody present. A standard can be included in the assay to monitor performance of the assay or to provide a reference for data generated in assays performed at different times.

Epitope: An antigenic determinant that is specifically bound by an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

Expressed: Translation of a nucleic acid into a protein. Proteins may be expressed and remain intracellular, become a component of the cell surface membrane, or be secreted into the extracellular matrix or medium.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences. A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Expression vector: A vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

Fc polypeptide: The polypeptide comprising the constant region of an antibody excluding the first constant region immunoglobulin domain. Fc region generally refers to the last two constant region immunoglobulin domains of IgA, IgD, and IgG, and the last three constant region immunoglobulin domains of IgE and IgM. An Fc region may also include part or all of the flexible hinge N-terminal to these domains. For IgA and IgM, an Fc region may or may not comprise the tailpiece, and may or may not be bound by the J chain. For IgG, the Fc region comprises immunoglobulin domains Cgamma2 and Cgamma3 (Cγ2 and Cγ3) and the lower part of the hinge between Cgamma1 (Cγ1) and Cγ2. Although the boundaries of the Fc region may vary, the human IgG heavy chain Fc region is usually defined to comprise residues C226 or P230 to its carboxyl-terminus, wherein the numbering is according to the EU index as in Kabat. For IgA, the Fc region comprises immunoglobulin domains Calpha2 and Calpha3 (Cα2 and Cα3) and the lower part of the hinge between Calpha1 (Cα1) and Cα2. Encompassed within the definition of the Fc region are functionally equivalent analogs and variants of the Fc region. A functionally equivalent analog of the Fc region may be a variant Fc region, comprising one or more amino acid modifications relative to the wild-type or naturally existing Fc region. Variant Fc regions will possess at least 50% homology with a naturally existing Fc region, such as about 80%, and about 90%, or at least about 95% homology. Functionally equivalent analogs of the Fc region may comprise one or more amino acid residues added to or deleted from the N- or C-termini of the protein, such as no more than 30 or no more than 10 additions and/or deletions. Functionally equivalent analogs of the Fc region include Fc regions operably linked to a fusion partner. Functionally equivalent analogs of the Fc region must comprise the majority of all of the Ig domains that compose Fc region as defined above; for example IgG and IgA Fc regions as defined herein must comprise the majority of the sequence encoding $CH_2$ and the majority of the sequence encoding $CH_3$. Thus, the $CH_2$ domain on its own, or the $CH_3$ domain on its own, are not considered Fc region. The Fc region may refer to this region in isolation, or this region in the context of an Fc fusion polypeptide (such as an immunoadhesin).

Hemagglutinin (HA): An influenza virus surface glycoprotein that is a homotrimeric integral membrane glycoprotein. HA mediates binding of the virus particle to a host cell and subsequent entry of the virus into the host cell. The nucleotide and amino acid sequences of numerous influenza HA proteins are known in the art and are publically available, such as through the NCBI Influenza Virus Resource database (Bao et al., *J Virol* 82:596-601, 2008). HA (along with NA) is one of the two major influenza virus antigenic determinants. The three identical monomers that constitute HA are constructed into a central α helix coil; three spherical heads contain the sialic acid binding sites. In nature, HA monomers are synthesized as precursors that are then glycosylated and cleaved into two smaller polypeptides: the HA1 and HA2 subunits. Each HA monomer consists of a long, helical chain anchored in the membrane by HA2 and topped by a large HA1 globular head which contains the sialic acid receptor binding sites. The HA2 protein chain facilitates membrane fusion; the C-terminal end of the protein is embedded in the viral membrane. The stalk of HA is comprised of portions of HA1 and HA2.

Host cells: Cells in which a vector can be propagated and its DNA expressed, for example a disclosed antibody can be expressed in a host cell. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Immunologically reactive conditions: Includes reference to conditions which allow an antibody raised against a particular epitope to specifically bind to that epitope to a detectably greater degree than, and/or to the substantial exclusion of, binding to substantially all other epitopes Immunologically reactive conditions are dependent upon the format of the antibody binding reaction and typically are those utilized in immunoassay protocols or those conditions encountered in vivo. See Harlow & Lane, supra, for a description of immunoassay formats and conditions. The immunologically reactive conditions employed in the methods are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (e.g., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

IgG: A polypeptide belonging to the class or isotype of antibodies that are substantially encoded by a recognized immunoglobulin gamma gene. In humans, this class comprises $IgG_1$, $IgG_2$, $IgG_3$, and $IgG_4$. In mice, this class comprises $IgG_1$, $IgG_2a$, $IgG_2b$, $IgG_3$.

Immune complex: The binding of antibody or antigen binding fragment to an antigen forms an immune complex. The formation of an immune complex can be detected through conventional methods known to the skilled artisan, for instance immunohistochemistry, immunoprecipitation, flow cytometry, immunofluorescence microscopy, ELISA, immunoblotting (for example, Western blot), magnetic resonance imaging, CT scans, X-ray diffraction and affinity chromatography Immunological binding properties of selected antibodies may be quantified using methods well known in the art.

Influenza virus: A segmented negative-strand RNA virus that belongs to the Orthomyxoviridae family. There are three types of Influenza viruses, A, B and C. Influenza A viruses infect a wide variety of birds and mammals, including humans, horses, marine mammals, pigs, ferrets, and chickens. In animals, most influenza A viruses cause mild localized infections of the respiratory and intestinal tract. However, highly pathogenic influenza A strains, such as H5N1, cause systemic infections in poultry in which mortality may reach 100%. H1N1 influenza was the most common cause of human influenza in 2009, and this strain was referred to as "swine flu," 2009 H1N1 pandemic (pdm) flu, or A(H1N1) pdm09 influenza virus. H1N1 influenza A viruses were also responsible for the Spanish flu pandemic in 1918, the Fort Dix outbreak in 1976, and the Russian flu epidemic in 1977-1978.

Influenza A viruses are categorized into subtypes based on the type of two proteins, hemagglutinin (HA) and neuraminidase (NA) that are on the surface of the viral envelope. Different influenza viruses encode for different HA and NA proteins. There are 18 different HA subtypes and 11 different NA subtypes, H1 through H18 and N1 through N11 respectively.

Influenza A viruses that have caused disease in humans include the following subtypes: H1N1, H2N2, and H3N2. Other subtypes of viruses that have infected humans but are not transmitted from person to person are: H5N1 (bird flu), H6N1, H7N7, H1N2, H9N2, H7N2, H7N3, H10N7 and H10N8. There are different lineages of HA and NA within each subtype that are distinguished by amino acid sequence. For example, H1N1 viruses that circulated before 2009 and swine flu H1N1 viruses that have circulated amongst humans since 2009, represent different HA and NA lineages. Within each lineage, virus variants of different "clades" circulate in the population each winter. The H1N1 related viruses currently circulating have HA and NA antigens that are antigenically similar to the A(H1N1)pdm09 virus and are called A(H1N1)pdm09-like viruses.

Antibodies that bind HA can block virus attachment to receptors or virus entry. Antibodies to NA, particularly those that inhibit its enzyme activity, reduce virus replication because newly formed virus particles cannot be released from the infected cell. Antibodies to HA and NA are associated with resistance to influenza disease.

Inhibiting or treating a disease/infection: Inhibiting the full development of a disease or condition, for example, in a subject who is at risk for a disease such as an influenza infection. "Treatment" refers to a therapeutic intervention that ameliorates a sign or symptom of an infection or pathological condition (such as the flu) after it has begun to develop. The term "ameliorating," with reference to a disease/infection or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the viral load, an improvement in the overall health or well-being of the subject, or by other parameters well known in the art that are specific to the particular disease. A "prophylactic" treatment is a treatment administered to a subject who has not yet been infected for the purpose of decreasing the risk of developing disease.

Isolated: An "isolated" biological component (such as a cell, for example a B cell, a nucleic acid, peptide, protein or antibody) has been substantially separated, produced apart from, or purified away from other biological components in the cell of the organism in which the component naturally occurs, such as, other chromosomal and extrachromosomal DNA and RNA, and proteins. Nucleic acids, peptides and proteins which have been "isolated" thus include nucleic acids and proteins purified by standard purification methods. The term also embraces nucleic acids, peptides, and proteins prepared by recombinant expression in a host cell as well as chemically synthesized nucleic acids.

$K_d$: The dissociation constant for a given interaction, such as a polypeptide ligand interaction or an antibody antigen interaction. For example, for the bimolecular interaction of an antibody (such as CD6) and an antigen (such as NA) it is the concentration of the individual components of the bimolecular interaction divided by the concentration of the complex.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In some examples, a disclosed antibody as labeled.

Neuraminidase (NA): An influenza virus membrane glycoprotein. NA is involved in the destruction of the cellular receptor for the viral HA by cleaving terminal sialic acid residues from carbohydrate moieties on the surfaces of infected cells. NA also cleaves sialic acid residues from viral proteins, preventing aggregation of viruses. NA (along with HA) is one of the two major influenza virus antigenic determinants. NA forms a tetramer comprised of four identical subunits (monomers) in vivo. As described under the term "influenza", antibodies that inhibit NA activity prevent virus spread, thereby limiting the infectious process and reducing morbidity and mortality.

Influenza neuraminidase exists as a mushroom-shape projection on the surface of the influenza virus. It has a head consisting of four co-planar and roughly spherical subunits, and a hydrophobic region that is embedded within the interior of the virus' membrane. The conformation of NAs from H1N1, H3N2 as well as other virus subtypes have been examined by x-ray crystallography. An exemplary GENBANK® accession number for the structure of the NA of A(H1N1)pdm09 virus A/California/07/2009 is 3NSS (Li, Q. et al. *Nat Struct Mol Biol* 17, 1266-8 (2010), incorporated herein by reference.

An antibody that specifically binds an N1 subtype influenza virus does not detectably bind an influenza virus of another subtype, such as N2, N3, N4, etc. An antibody that binds NA can specifically bind to a single variant or all variants within a lineages. The monoclonal antibodies disclosed herein bind to N1 subtype influenza viruses, such as A(H1N1)pdm viruses, but does not detectably bind to influenza viruses of subtypes N2-N11.

Neutralizing antibody: An antibody which reduces the infectious titer of an infectious agent by binding to a specific antigen on the infectious agent. In some examples the infectious agent is a virus. In some examples, an antibody that is specific for NA reduces the infectious titer of influenza virus.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. This includes nucleic acid vectors comprising an amplified or assembled nucleic acid which can be used to transform a suitable host cell. A host cell that comprises the recombinant nucleic acid is referred to as a "recombinant host cell." The gene is then expressed in the recombinant host cell to produce, e.g., a "recombinant polypeptide." A recombinant nucleic acid may serve a non-coding function (e.g., promoter, origin of replication, ribosome-binding site, etc.) as well.

A first sequence is an "antisense" with respect to a second sequence if a polynucleotide whose sequence is the first sequence specifically hybridizes with a polynucleotide whose sequence is the second sequence.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, e.g., by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds 1995 supplement)).

One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (ncbi.nlm.nih.gov). The BLASTN program (for nucleotide sequences) uses as defaults a word length (W) of 11, alignments (B) of 50, expectation (E) of 10, M=5, N=−4, and a comparison of both strands. An oligonucleotide is a linear polynucleotide sequence of up to about 100 nucleotide bases in length.

A polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA. An NA polynucleotide is a nucleic acid encoding a NA polypeptide; and an NA antibody polynucleotide is a nucleic acid encoding an antibody that specifically binds NA.

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

Outbreak: As used herein, an influenza virus "outbreak" refers to a collection of virus isolates from within a single country in a given year.

Pharmaceutical agent: A chemical compound or composition capable of inducing a desired therapeutic or prophylactic effect when properly administered to a subject or a cell. In some examples a pharmaceutical agent includes one or more of the disclosed antibodies. A pharmaceutical agent can be an antiviral agent.

Pharmaceutically acceptable carriers: The pharmaceutically acceptable carriers of use are conventional. *Remington's Pharmaceutical Sciences*, by E. W. Martin, Mack Publishing Co., Easton, Pa., 19th Edition, 1995, describes compositions and formulations suitable for pharmaceutical delivery of the disclosed antibodies.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: Any chain of amino acids, regardless of length or post-translational modification (e.g., glycosylation or phosphorylation). In one embodiment, the polypeptide is a NA polypeptide. In one embodiment, the polypeptide is a disclosed antibody or a fragment thereof. A "residue" refers to an amino acid or amino acid mimetic incorporated in a polypeptide by an amide bond or amide bond mimetic. A polypeptide has an amino terminal (N-terminal) end and a carboxy terminal end.

Polypeptides can be modified by a variety of chemical techniques to produce derivatives having essentially the same activity and conformation as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains can be converted to $C_1$-$C_{16}$ alkoxy or to a $C_1$-$C_{16}$ ester using well-recognized techniques. Phenyl and phenolic rings of the peptide side chains can be substituted with one or more halogen atoms, such as F, Cl, Br or I, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups.

Purified: The term purified does not require absolute purity; rather, it is intended as a relative term. Thus, for example, a purified peptide preparation is one in which the peptide or protein (such as an antibody) is more enriched than the peptide or protein is in its natural environment within a cell. For example, other molecules, e.g. polypeptide, nucleic acid molecules that have been identified and separated and/or recovered from a component of its natural environment. In some examples, purified antibodies have been separated from one or more components of their natural environment. In one embodiment, a preparation is purified such that the protein or peptide represents at least 50% of the total peptide or protein content of the preparation.

The antibodies that specifically bind NA as disclosed herein can be purified by any of the means known in the art. See for example *Guide to Protein Purification*, ed. Deutscher, *Meth. Enzymol.* 185, Academic Press, San Diego, 1990; and Scopes, *Protein Purification: Principles and Practice*, Springer Verlag, New York, 1982. Substantial purification denotes purification from other proteins, antibodies, or cellular components. A substantially purified protein is at least 60%, 70%, 80%, 90%, 95% or 98% pure. Thus, in one specific, non-limiting example, a substantially purified protein is 90% free of other proteins or cellular components.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques. A recombinant protein is a protein that is expressed from a cell transfected with recombinant nucleic acid.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, Gene 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989).

Homologs and variants of a $V_L$ or a $V_H$ of an antibody that specifically binds a polypeptide are typically characterized by possession of at least about 75%, for example at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Specifically bind: When referring to an antibody, refers to a binding reaction which determines the presence of a target protein, peptide, or polysaccharide in the presence of a heterogeneous population of proteins and other biologics. Thus, under designated conditions, an antibody binds preferentially to a particular target protein, peptide or polysaccharide (such as an antigen of a pathogen, for example NA) and does not bind in a significant amount to other proteins or polysaccharides present in the sample or subject. Specific binding can be determined by methods known in the art. With reference to an antibody antigen complex, specific binding of the antigen and antibody has a $K_d$ of less than about $10^{-6}$ Molar, $10^{-7}$ Molar, $10^{-8}$ Molar, $10^{-9}$, or even less than about $10^{-10}$ Molar.

The antibodies disclosed herein specifically bind to a defined target, NA of N1 subtype influenza viruses, such as, but not limited to, A(H1N1)pdm09 influenza viruses and related N1 subtype influenza viruses. Thus, an antibody that specifically binds to NA of an N1 subtype influenza virus is an antibody that binds substantially to NA of N1 subtype influenza viruses, including dimers and multimers thereof, including cells or tissue expressing NA, substrate to which NA is attached, or an N1 subtype influenza virus in a biological specimen. It is, of course, recognized that a certain degree of non-specific interaction may occur between an antibody or conjugate including an antibody and a non-target. Typically, specific binding results in a much stronger association between the antibody and protein or cells bearing the antigen than between the antibody and protein or cells lacking the antigen. Specific binding typically results in greater than 2-fold, such as greater than 5-fold, greater than 10-fold, or greater than 100-fold increase in amount of bound antibody (per unit time) to a protein including the epitope or cell or tissue expressing the target epitope as compared to a protein or cell or tissue lacking this epitope. Specific binding to an epitope under such conditions requires an antibody that is selected for its specificity for a particular epitope. A variety of immunoassay formats are appropriate for selecting antibodies or other ligands specifically immunoreactive with a particular epitope. For example, solid-phase ELISA immunoassays are routinely used to select monoclonal antibodies specifically immunoreactive with a protein. See Harlow & Lane, *Antibodies, A Laboratory Manual*, 2nd ed., Cold Spring Harbor Publications, New York (2013), for a description of immunoassay formats and conditions that can be used to determine specific immunoreactivity.

Therapeutically effective amount: A quantity of a specific substance, such as a disclosed antibody, sufficient to achieve a desired effect in a subject being treated. For instance, this can be the amount necessary to inhibit influenza virus replication or treat the flu. In several embodiments, a therapeutically effective amount is the amount necessary to reduce a sign or symptom of the flu, and/or to decrease viral titer in a subject. When administered to a subject, a dosage will generally be used that will achieve a desired clinical effect. For example, a reduction in symptoms, such as fever, coughing, sore throat or fatigue.

Under conditions sufficient for: A phrase that is used to describe any environment that permits a desired activity. In one example the desired activity is formation of an immune complex. In particular examples the desired activity is treatment of an influenza virus infection.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Virus: Microscopic infectious organism that reproduces inside living cells. A virus consists essentially of a core of nucleic acid surrounded by a protein coat, and has the ability to replicate only inside a living cell. "Viral replication" is the production of additional virus by the occurrence of at least one viral life cycle. A virus may subvert the host cells' normal functions, causing the cell to behave in a manner determined by the virus. For example, a viral infection may result in a cell producing a cytokine, or responding to a cytokine, when the uninfected cell does not normally do so.

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Monoclonal Antibodies that Specifically Bind NA

Figure 4A:
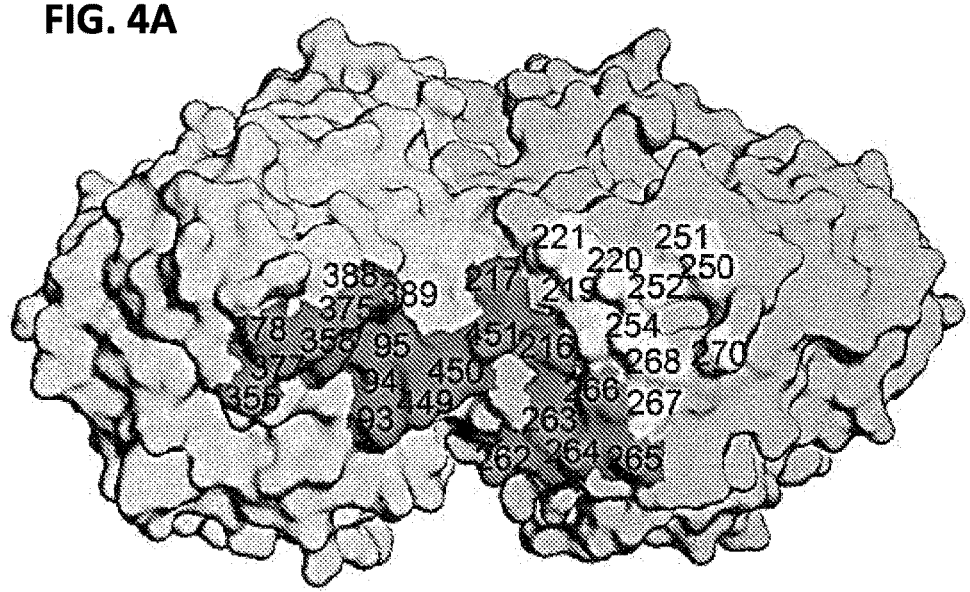
FIGS. 4A-4C. Antibody-antigen recognition by CD6. (4A) Footprint of CD6 on NA. Two NA monomers are shown. NA residues interacting with the H chain are colored in dark grey and the L chain in light grey. The interacting residues of NA are labeled. (4B) Footprint of NA on CD6 (color theme is the same as in (4A)). The interacting residues of CD6 are labeled. (4C) Position of the CD6 CDRs on CA/09 NA. Residues interacting with the H chain are colored in dark grey and the L chain in light grey. CDR loops are shown as tubes. Ser95, Asn449 and Asp451 comprise a focal point of interactions with the H chain of CD6, forming hydrogen bonds to Thr31 and Tyr104 on the HCDR1 and HCDR3 respectively (shown as grey sticks).

Isolated monoclonal antibodies and antigen binding fragments thereof that specifically bind NA of an N1 subtype influenza virus are disclosed herein. Epitope mapping and structural studies allowed for detailed analysis of the binding of antibody CD6 to NA of an N1 subtype influenza virus at a previously uncharacterized epitope that spans two adjacent monomers of NA in a tetramer (see FIG. 3A). FIG. 4A is an image of a dimer showing two adjacent monomers that abut each other in a tetramer. The present disclosure encompasses monoclonal antibodies and antigen binding fragments thereof that specifically bind this epitope.

In some embodiments, the monoclonal antibody specifically binds two adjacent monomers in an NA tetramer, wherein the antibody contacts amino acids 449 and 451 of a first of the adjacent monomers in an NA tetramer. In additional embodiments, the monoclonal antibody specifically binds two adjacent monomers in an NA tetramer, wherein the antibody contacts amino acids 93, 94, 95, 355, 358, 375, 377, 378, 388, 389, 449, 450, 451 on a first of the adjacent monomers in an NA tetramer and amino acids 216, 217, 219, 220, 221, 250, 251, 252, 254, 262, 263, 264, 265, 266, 267, 268, 270 on the second of the adjacent monomers on an NA tetramer of an N1 subtype influenza virus. The contacts are all non-covalent bonds and include hydrophobic interactions, hydrogen bonds and indirect interactions through water molecules. The position of amino acids in NA referred to herein is according the NA amino acid sequence set forth as GENBANK® Accession No. AGM53851, as available on Dec. 1, 2014, which is incorporated herein by reference, unless context indicates otherwise. The numbering of amino acids follows the sequence of this N1 sequence.

In several embodiments, the antibodies and antigen binding fragments bind NA of an N1 subtype influenza virus with a binding affinity of $1 \times 10^{-8}$ M, at least about $1.5 \times 10^{-8}$ M, at least about $2 \times 10^{-8}$ M, at least about $3 \times 10^{-8}$ M, at least about $3 \times 10^{-8}$ M, at least about $5 \times 10^{-8}$ M, at least about $6 \times 10^{-8}$ M, at least about $7 \times 10^{-8}$ M, at least about $8 \times 10^{-8}$ M, at least about $9 \times 10^{-8}$ M, or at least about $1 \times 10^{-7}$ M. In some embodiments the monoclonal antibodies and antigen binding fragments specifically bind NA of an N1 subtype influenza virus.

An exemplary heavy chain variable domain is shown below, with exemplary CDRs unlined and contact residues shown in bold:

```
                                                    (SEQ ID NO: 1)
QVKLQESGGGLVQPKGSLKLSCAASGFTFNTYAMNWVRQAPGKGLEWVAR

IRSKSNNYATFYADSVKDRFTISRDDSQSMLYLQMHNLKTDDTAMYYCVR

PSIYYYASGYLDVWGAGTTVTVSSAKTTAPSVYPLAPVCGDTTGSSVTLG

CLVKGYFPEPVTLTWNSGSLSSGVHTFPAVLQSDLYTLSSSVTVTSSTWP

SQSITCNVAHPASSTKVDKKIEPRGPTIKPCPPCKCPAPNLLGGPSVFIF

PPKIKDVLMISLSPIVTCVVVDVSEDDPDVQISWFVNNVEVHTAQTQTHR

EDYNSTLRVVSALPIQHQDWMSGKEFKCKVNNKDLTAPIERTISKPKGSV

RAPQVYVLPPPEEEMTKKQVTLTCMVTDFMPEDIYVEWTNNGKTELNYKN

TEPVLDSDGSYFMYSKLRVEKKNWVERNSYSCSVVHEGLHNHHTTKSLAH

SPGK.
```

In some embodiments, an isolated monoclonal antibody or antigen binding fragment is disclosed, wherein the heavy chain variable domain comprises a heavy chain complementarity determining region (HCDR)1, an HCDR2 and an HCDR3, wherein and wherein the light chain variable domain comprises an LCDR1, an LCDR2 and an LCDR3. In particular examples, the heavy chain variable comprises the HCDR1, HCDR2 and HCDR3 of SEQ ID NO: 1.

In further embodiments, an isolated monoclonal antibody is disclosed that includes a heavy chain variable domain and a light chain variable domain, wherein the heavy chain variable domain comprises a heavy chain complementarity determining region (HCDR)1, an HCDR2 and an HCDR3, wherein the HCDR1 comprises the amino acid sequence set forth as amino acids 26 to 33 of SEQ ID NO: 1, the HCDR2 comprises the amino acid sequence set forth as amino acids 51 to 60 of SEQ ID NO: 1, and/or the HCDR3 comprises the amino acid sequence set forth as amino acids 99 to 113 of SEQ ID NO: 1. In additional embodiments, the heavy chain variable domain comprises a heavy chain complementarity determining region (HCDR)1, an HCDR2 and an HCDR3, wherein the HCDR1 comprises the amino acid sequence set forth as amino acids 26 to 33 of SEQ ID NO: 1, the HCDR2 comprises the amino acid sequence set forth as amino acids 51 to 60 of SEQ ID NO: 1, and the HCDR3 comprises the amino acid sequence set forth as amino acids 99 to 113 of SEQ ID NO: 1. The monoclonal antibody specifically binds NA of an N1 subtype influenza virus, such as A(H1N1) pdm09.

An exemplary light chain variable domain is shown below, with exemplary CDRs underlined and contact residues shown in bold:

```
                                              (SEQ ID NO: 2)
QIVLSQSPAILSASPGEKVTMTCRTSSSVSYMHWYQQKPGSSPKPWIYAT

SNLASGVPFRFSGSGSGTSYSLTISRVEAEDAATYYCQQWNSNPPTFGGG

TKLEIKRADAAPTVSIFPPSSEQLTSGGASVVCFLNNFYPKDINVKWKID

GSERQNGVLNSWTDQDSKDSTYSMSSTLTLTKDEYERHNSYTCEATHKTS

TSPIVKSFNRNEC.
```

In some embodiments, a monoclonal antibody is disclosed wherein the light chain variable domain comprises the LCDR1, an LCDR2 and an LCDR3 of SEQ ID NO: 2. In further embodiments, the light chain variable domain comprises an LCDR1, an LCDR2 and an LCDR3, wherein LCDR1 comprises the amino acid sequence set forth as amino acids 27 to 31 of SEQ ID NO: 2, the LCDR2 comprises the amino acid sequence set forth as amino acids 49 to 51 of SEQ ID NO:2, and/or the LCDR3 comprises the amino acid sequence set forth as amino acids 88 to 96 of SEQ ID NO: 2. In additional embodiments, the light chain variable domain comprises an LCDR1, an LCDR2 and an LCDR3, wherein LCDR1 comprises the amino acid sequence set forth as amino acids 27 to 31 of SEQ ID NO: 2, the LCDR2 comprises the amino acid sequence set forth as amino acids 49 to 51 of SEQ ID NO:2, and the LCDR3 comprises the amino acid sequence set forth as amino acids 88 to 96 of SEQ ID NO: 2. The monoclonal antibody specifically binds NA of an N1 subtype influenza virus, such as A(H1N1)pdm09.

In some embodiments, the monoclonal antibody includes a heavy chain variable domain comprising an amino acid sequence at least 90%, 91%, 92%, 93%, 94%, 95%, 96%, 97%, 98% or 99% identical to one of the amino acid sequence set forth as SEQ ID NO: 1. In additional embodiments, the he monoclonal antibody includes a light chain variable domain comprising an amino acid sequence at least 90%, 91%, 92%, 93%, 94%, 95%, 96%, 97%, 98% or 99% identical to one of the amino acid sequence set forth as SEQ ID NO: 2. The monoclonal antibody specifically binds NA of an N1 subtype influenza virus, such as A(H1N1)pdm09.

One of skill will realize that conservative variants of the antibodies can be produced. Such conservative variants employed in antibody fragments will retain critical amino acid residues necessary for correct folding and stabilizing between the $V_H$ and the $V_L$ regions, and will retain the charge characteristics of the residues Amino acid substitutions (such as at most one, at most two, at most three, at most four, or at most five amino acid substitutions) can be made in the $V_H$ and the $V_L$ regions to increase yield. Conservative amino acid substitution tables providing functionally similar amino acids are well known to one of ordinary skill in the art. Thus, one of skill in the art can readily review the sequences shown above, identify a conservative substitution, and produce the conservative variant using well-known molecular techniques. In additional embodiments, the heavy chain variable domain includes at most 10, at most 9, at most 8, at most 7, at most 6, at most 5, at most 4, at most 3, at most two or at most one conservative amino acid substitutions in an amino acid sequence set forth as SEQ ID NO: 1. In additional embodiments, the light chain variable domain includes at most 10, at most 9, at most 8, at most 7, at most 6, at most 5, at most 4, at most 3, at most two or at most one conservative amino acid substitutions in an amino acid sequence set forth as SEQ ID NO: 2. In additional embodiments, the heavy chain variable domain includes the amino acid sequence set forth as SEQ ID NO: 1. In other embodiments, the light chain variable domain includes the amino acid sequence set forth as SEQ ID NO: 2. In a specific non-limiting example, the heavy chain variable domain includes the amino acid sequence set forth as SEQ ID NO: 1 and the light chain variable domain includes the amino acid sequence set forth as SEQ ID NO: 2. The monoclonal antibody specifically binds NA of an N1 subtype influenza virus, such as A(H1N1)pdm09.

Naturally-occurring antibodies are immunoglobulin molecules comprised of four polypeptide chains, two heavy (H) chains and two light (L) chains inter-connected by disulfide bonds. Each heavy chain is comprised of a heavy chain variable region (VH) and a heavy chain constant region. The heavy chain constant region is comprised of three domains, CH1, CH2 and CH3. Each light chain is comprised of a light chain variable region (VL) and a light chain constant region. The light chain constant region is comprised of one domain, CL. The VH and VL regions can be further subdivided into regions of hypervariability, called complementarity determining regions (CDR), interspersed with regions that are more conserved, called framework regions (FWR). Each VH and VL is composed of three CDRs and four FWRs, arranged from amino-terminus to carboxy-terminus in the following order: FWR1, CDR1, FWR2, CDR2, FWR3, CDR3, FWR4.

CDRs and FWRs may be defined according to Kabat (Sequences of Proteins of Immunological Interest (National Institutes of Health, Bethesda, Md., 1987 and 1991) Amino acid numbering of antibodies or antigen binding fragments is also according to that of Kabat. Each CDR can include amino acid residues from a complementarity determining region as defined by Kabat (i.e. about residues 24-34 (CDR-L1), 50-56 (CDR-L2) and 89-97 (CDR-L3) in the light chain variable domain (and 31-35 (CDR-H1), 50-65 (CDR-H2) and 95-102 (CDR-H3) in the heavy chain variable domain (SEQ ID NO:1). However, in some antibodies the CDRs include those residues from a hypervariable loop (i.e. about residues 26-32 (CDR-L1), 50-52 (CDR-L2) and 91-96 (CDR-L3) in the light chain variable domain (SEQ ID NO:2) and 26-32 (CDR-H1), 53-55 (CDR-H2) and 96-101 (CDR-H3) in the heavy chain variable domain (SEQ ID NO: 1); Chothia and Lesk J. Mol. Biol. 196:901-917 (1987)). In some instances, a complementarity determining region can include amino acids from both a CDR region defined according to Kabat and a hypervariable loop.

In a wild type antibody, each variable domain typically has four FWRs identified as FWR1, FWR2, FWR3 and FWR4. If the CDRs are defined according to Kabat, the light chain FWR residues are positioned at about residues 1-23 (LCFR1), 35-49 (LCFR2), 57-88 (LCFR3), and 98-107 (LCFR4) of SEQ ID NO:2) and the heavy chain FWR residues are positioned about at residues 1-30 (HCFR1), 36-49 (HCFR2), 66-94 (HCFR3), and 103-113 (HCFR4) of SEQ ID NO:1. If the CDRs comprise amino acid residues from hypervariable loops, the light chain FWR residues are positioned about at residues 1-25 (LCFR1), 33-49 (LCFR2), 53-90 (LCFR3), and 97-107 (LCFR4) in the light chain (SEQ ID NO:2) and the heavy chain FWR residues are positioned about at residues 1-25 (HCFR1), 33-52 (HCFR2), 56-95 (HCFR3), and 102-113 (HCFR4) in the heavy chain (SEQ ID NO:1). In some instances, when the CDR comprises amino acids from both a CDR as defined by Kabat and those of a hypervariable loop, the FWR residues are adjusted accordingly.

Thus, in some embodiments, the monoclonal antibody includes one or more CDRs from the variable domains shown SEQ ID NOs: 1 and 2, as defined by the Kabat, Chothia or IMGT numbering system. Thus, in other embodiments, the monoclonal antibody includes all of the CDRs from the variable domains shown SEQ ID NOs: 1 and 2, as defined by the Kabat, Chothia or IMGT numbering system. The monoclonal antibody specifically binds NA of an N1 subtype influenza virus, such as A(H1N1)pdm09. The monoclonal antibody can be humanized or chimeric.

In additional embodiments, the heavy chain of the monoclonal antibody includes the CDRs from the heavy chain variable domain set forth as SEQ ID NO: 1 (as defined by the Kabat, Chothia or IMGT numbering system) and includes one or more of a serine (S) at amino acid 25, a glycine (G) at amino acid 26, a phenylalanine (F) at amino acid 27, a threonine (T) at amino acid 28, a phenylalanine (F) at amino acid 29, an asparagine (N) at amino acid 30, a threonine (T) at amino acid 31, a tyrosine (Y) at amino acid 32, a serine (S) at amino acid 55, an aspartic acid (D) at amino acid 76, a serine (S) at amino acid 77, a serine (S) at amino acid 79, an arginine (R) at amino acid 100, an isoleucine (I) at amino acid 103, a tyrosine (Y) at amino acid 104, a tyrosine (Y) at amino acid 105, and a tyrosine (Y) at amino acid 106. All of these amino acids can be included in the heavy chain variable domain. In other embodiments, the heavy chain of the monoclonal antibody includes the CDRs from the heavy chain variable domain set forth as SEQ ID NO: 1 (as defined by the Kabat, Chothia or IMGT numbering system), and a serine (S) at amino acid 25, an aspartic acid (D) at amino acid 76, a serine (S) at amino acid 77, and a serine (S) at amino acid 79. In further embodiments, the heavy chain variable domain comprises a heavy chain complementarity determining region (HCDR)1, an HCDR2 and an HCDR3, wherein the HCDR1 comprises the amino acid sequence set forth as amino acids 26 to 33 of SEQ ID NO: 1, the HCDR2 comprises the amino acid sequence set forth as amino acids 51 to 60 of SEQ ID NO: 1, and/or the HCDR3 comprises the amino acid sequence set forth as amino acids 99 to 113 of SEQ ID NO: 1, and wherein the heavy chain variable domain also includes one or more of a serine (S) at amino acid 25, an aspartic acid (D) at amino acid 76, a serine (S) at amino acid 77, and a serine (S) at amino acid 79. All of these amino acids can be included in the heavy chain variable domain. In yet other embodiments, the heavy chain variable domain comprises a heavy chain complementarity determining region (HCDR)1, an HCDR2 and an HCDR3, wherein the HCDR1 comprises the amino acid sequence set forth as amino acids 26 to 33 of SEQ ID NO: 1, the HCDR2 comprises the amino acid sequence set forth as amino acids 51 to 60 of SEQ ID NO: 1, and/or the HCDR3 comprises the amino acid sequence set forth as amino acids 99 to 113 of SEQ ID NO: 1, and the heavy chain variable domain includes a serine (S) at amino acid 25, an aspartic acid (D) at amino acid 76, a serine (S) at amino acid 77, and a serine (S) at amino acid 79. All of these amino acids can be included in the heavy chain variable domain. The monoclonal antibody specifically binds NA of an N1 subtype influenza virus, such as A(H1N1)pdm09.

In some embodiments, the light chain of the monoclonal antibody or antigen binding fragment includes the CDRs from the light chain variable domain set forth as SEQ ID NO: 2 (as defined by the Kabat, Chothia or IMGT numbering system) and includes one or more of a tyrosine (Y) at amino acid 48, an alanine (A) at amino acid 49, a serine (S) at amino acid 51, an asparagine (N) at amino acid 52, a leucine (L) at amino acid 53, a serine (S) at amino acid 55, a valine (V) at amino acid 57, a phenylalanine (F) at amino acid 59, and a serine (S) at amino acid 62. All of these amino acids can be included in the light chain variable domain. In additional embodiments, the light chain of the monoclonal antibody or antigen binding fragment includes the CDRs from the light chain variable domain set forth as SEQ ID NO: 2 (as defined by the Kabat, Chothia or IMGT numbering system) and includes a tyrosine (Y) at amino acid 48, an asparagine (N) at amino acid 52, a leucine (L) at amino acid 53, a serine (S) at amino acid 55, a valine (V) at amino acid 57, an phenylalanine (F) at amino acid 59, and a serine (S) at amino acid 62. All of these amino acids can be included in the light chain variable domain. In other embodiments, the light chain variable domain comprises an LCDR1, an LCDR2 and an LCDR3, wherein LCDR1 comprises the amino acid sequence set forth as amino acids 27 to 31 of SEQ ID NO: 2, the LCDR2 comprises the amino acid sequence set forth as amino acids 49 to 51 of SEQ ID NO:2, and the LCDR3 comprises the amino acid sequence set forth as amino acids 88 to 96 of SEQ ID NO: 2, and includes one or more of a tyrosine (Y) at amino acid 48, an asparagine (N) at amino acid 52, a leucine (L) at amino acid 53, a serine (S) at amino acid 55, a valine (V) at amino acid 57, a phenylalanine (F) at amino acid 59, and a serine (S) at amino acid 62. All of these amino acids can be included in the light chain variable domain. In further embodiments, the light chain variable domain comprises an LCDR1, an LCDR2 and an LCDR3, wherein LCDR1 comprises the amino acid sequence set forth as amino acids 27 to 31 of SEQ ID NO: 2, the LCDR2 comprises the amino acid sequence set forth as amino acids 49 to 51 of SEQ ID NO:2, and the LCDR3 comprises the amino acid sequence set forth as amino acids 88 to 96 of SEQ ID NO: 2, and includes a tyrosine (Y) at amino acid 48, an asparagine (N) at amino acid 52, a leucine (L) at amino acid 53, a serine (S) at amino acid 55, a valine (V) at amino acid 57, a phenylalanine (F) at amino acid 59, and a serine (S) at amino acid 62. All of these amino acids can be included in the light chain variable domain. The monoclonal antibody specifically binds NA of an N1 subtype influenza virus, such as A(H1N1)pdm09.

The mAb can be of any isotype. The mAb can be, for example, an IgM or an IgG antibody, such as IgG$_1$ or an IgG$_2$. The class of an antibody can be switched with another. In one aspect, a nucleic acid molecule encoding V$_L$ or V$_H$ is isolated using methods well-known in the art, such that it does not include any nucleic acid sequences encoding the constant region of the light or heavy chain, respectively. The nucleic acid molecule encoding V$_L$ or V$_H$ is then operatively linked to a nucleic acid sequence encoding a C$_L$ or C$_H$ from a different class of immunoglobulin molecule. This can be achieved using a vector or nucleic acid molecule that comprises a C$_L$ or C$_H$ chain, as known in the art. For example, class switching can be used to convert one IgG subclass to another, such as from IgG$_1$ to IgG$_2$. The monoclonal antibody (or an antigen binding fragment thereof) can be humanized or chimeric.

Antibody fragments are encompassed by the present disclosure, such as Fab, F(ab')$_2$, and Fv which include a heavy chain and light chain variable region and are capable of binding NA. These antibody fragments retain the ability to selectively bind with the antigen. The fragments can be included in a bispecific antibody. These antigen binding fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, a genetically engineered fragment containing the variable region of the light chain and the variable region of the heavy chain expressed as two chains;

(5) Single chain antibody (such as scFv), defined as a genetically engineered molecule containing the variable region of the light chain, the variable region of the heavy chain, linked by a suitable polypeptide linker as a genetically fused single chain molecule; and (6) A dimer of a single chain antibody (scFV$_2$), defined as a dimer of an scFV. This has also been termed a "miniantibody."

In specific non-limiting examples, the antibody fragment is a (Fab)$_2$, a scFV$_2$, or a scFv.

In some embodiments, the antibody fragment has a molecular weight of greater than about 50 kilodaltons (kD), greater than about 60 kD, greater than about 70 kD, greater than about 80 kD, greater than about 90 kD, or greater than about 100 kD. The antibody fragment can have a molecular weight of greater than about 50 kD and less than about 150 kD. Thus, in some embodiments, the antibody fragment is not a Fab, which has a molecular weight of 50 kD, or a Fv, which has a molecular weight of about 25 kD. However, the antibody fragment can be a Fab or an Fv. In some embodiments, an antibody fragment is coupled to another molecule, such that the conjugate has a molecular weight of greater than about 50 kD, greater than about 60 kD, greater than about 70 kD, greater than about 80 kD, greater than about 90 kD, or greater than about 100 kD.

Methods of making these fragments are known in the art (see for example, Harlow and Lane, *Antibodies: A Laboratory Manual*, Cold Spring Harbor Laboratory, New York, 1988). In one group of embodiments, the antibodies have V$_H$, or a combination of these CDRs, as discussed above.

Fv antibodies are typically about 25 kDa and contain a complete antigen-binding site with three CDRs per each heavy chain and each light chain. To produce these antibodies, the V$_H$ and the V$_L$ can be expressed from two individual nucleic acid constructs in a host cell. If the V$_H$ and the V$_L$ are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker. Thus, in some examples, the Fv can be a disulfide stabilized Fv (dsFv), wherein the heavy chain variable region and the light chain variable region are chemically linked by disulfide bonds.

In an additional example, the Fv fragments comprise V$_H$ and V$_L$ chains connected by a peptide linker. These single-chain antigen binding proteins (scFv) are prepared by constructing a structural gene comprising DNA sequences encoding the V$_H$ and V$_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing scFvs are known in the art (see Whitlow et al., *Methods: a Companion to Methods in Enzymology*, Vol. 2, page 97, 1991; Bird et al., *Science* 242:423, 1988; U.S. Pat. No. 4,946,778; Pack et al., *Bio/Technology* 11:1271, 1993; and Sandhu, supra). Dimers of a single chain antibody (scFV$_2$), are also contemplated.

Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. No. 4,036,945 and U.S. Pat. No. 4,331,647, and references contained therein; Nisonhoff et al., *Arch. Biochem. Biophys.* 89:230, 1960; Porter, Biochem. J. 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

The antibodies or antibody fragments disclosed herein can be derivatized or linked to another molecule (such as another peptide or protein). In general, the antibody or portion thereof is derivatized such that the binding to NA is not affected adversely by the derivatization or labeling. For example, the antibody can be functionally linked, for example, by chemical coupling, genetic fusion, noncovalent association or otherwise to one or more other molecular entities, such as another antibody (for example, a bispecific antibody or a diabody), a detection agent, a pharmaceutical agent, and/or a protein or peptide that can mediate association of the antibody or antibody portion with another molecule (such as a streptavidin core region or a polyhistidine tag). In some embodiments, the derivatized antibody or antibody fragment has a molecular weight that is greater than about 50 kD, greater than about 60 kD, greater than about 70 kD, greater than about 80 kD, greater than about 90 kD, or greater than about 100 kD.

One type of derivatized antibody is produced by cross-linking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are available from Pierce Chemical Company (Rockford, Ill.).

An antibody or antibody fragment that specifically binds NA of an N1 subtype influenza virus, such as A(H1N1) pdm09, can be labeled with a detectable moiety. Useful detection agents include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, green fluorescent protein (GFP), or yellow fluorescent protein. An antibody can also be labeled with enzymes that are useful for detection, such as horseradish peroxidase, β-galactosidase, luciferase, alkaline phosphatase, glucose oxidase and the like. When an antibody or antibody fragment is labeled with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody or antibody fragment may also be labeled with biotin, and detected through indirect measurement of avidin or streptavidin binding. It should be noted that the avidin itself can be labeled with an enzyme or a fluorescent label.

An antibody or antibody fragment may be labeled with a magnetic agent, such as gadolinium. Antibodies or antibody fragments can also be labeled with lanthanides (such as europium and dysprosium), and manganese. Paramagnetic particles such as superparamagnetic iron oxide are also of use as labels. An antibody or antibody fragment can also be labeled with a predetermined polypeptide epitopes recognized by a secondary reporter (such as leucine zipper pair sequences, binding sites for secondary antibodies, metal binding domains, epitope tags). In some embodiments, labels are attached by spacer arms of various lengths to reduce potential steric hindrance.

An antibody or antibody fragment can also be labeled with a radiolabeled amino acid. Examples of radiolabels include, but are not limited to, the following radioisotopes or radionucleotides: $^{3}H$, $^{14}C$, $^{15}N$, $^{35}S$, $^{90}Y$, $^{99}Tc$, $^{111}In$, $^{125}I$, $^{131}I$. The radiolabel may be used for both diagnostic and therapeutic purposes.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

The antibodies or antibody fragments disclosed herein can be derivatized or linked to another molecule (such as another peptide or protein). In general, the antibody or portion thereof is derivatized such that the binding to NA is not affected adversely by the derivatization or labeling. For example, the antibody can be functionally linked (by chemical coupling, genetic fusion, noncovalent association or otherwise) to one or more other molecular entities, such as another antibody (for example, a bispecific antibody or a diabody), a detection agent, a pharmaceutical agent, and/or a protein or peptide that can mediate associate of the antibody or antibody portion with another molecule (such as a streptavidin core region or a polyhistidine tag).

One type of derivatized antibody or antibody fragment is produced by cross-linking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are available from Pierce Chemical Company (Rockford, Ill.).

An antibody or antibody fragment can also be derivatized with a chemical group such as polyethylene glycol (PEG), a methyl or ethyl group, or a carbohydrate group. These groups may be useful to improve the biological characteristics of the antibody, such as to increase serum half-life or to increase tissue binding. They can also be used to increase the size of the antibody fragment.

Polynucleotides and Expression

Nucleotide sequences are provided that encode an antibody or antigen binding fragment thereof, that specifically binds NA of an N1 subtype influenza virus. Expression vectors are also provided for their efficient expression in cells (for example, mammalian cells).

Recombinant expression of an antibody generally requires construction of an expression vector containing a polynucleotide that encodes the antibody or antibody fragment. Replicable vectors are provided including a nucleotide sequence encoding an antibody molecule, a heavy or light chain of an antibody, a heavy or light chain variable domain of an antibody or a portion thereof, or a heavy or light chain CDR, operably linked to a promoter. Such vectors may include the nucleotide sequence encoding the constant region of an antibody molecule (see, e.g., U.S. Pat. Nos. 5,981,216; 5,591,639; 5,658,759 and 5,122,464) and the variable domain of the antibody may be cloned into such a vector for expression of the entire heavy, the entire light chain, or both the entire heavy and light chains.

Nucleic acid molecules (also referred to as polynucleotides) encoding the polypeptides provided herein (including, but not limited to antibodies) can readily be produced by one of skill in the art. For example, these nucleic acids can be produced using the amino acid sequences provided herein (such as the CDR sequences, heavy chain and light chain sequences), sequences available in the art (such as framework sequences), and the genetic code.

An exemplary $V_H$ nucleic acid sequences is set forth as SEQ ID NO: 3 and includes degenerate variants thereof; an exemplary $V_L$ nucleic acid sequences is set forth as SEQ ID NO: 4, and includes degenerate variants thereof, see below:

```
CAGGTTAAGCTGCAGGAGTCTGGTGGAGGATTGGTGCAGCCTAAAGGGT

CATTGAAACTCTCATGTGCAGCCTCTGGATTCACTTTCAATACCTACGC
```

CATGAACTGGGTCCGCCAGGCTCCAGGAAAGGGTTTGGAATGGGTTGCT

CGCATAAGAAGTAAAAGTAATAATTATGCAACATTTTATGCCGATTCAG

TGAAAGACAGGTTCACCATCTCCAGAGATGATTCACAAAGCATGCTCTA

TCTGCAAATGCACAACTTGAAAACTGACGACACAGCCATGTATTACTGT

GTGAGACCCTCTATTTATTACTACGCTAGTGGATACCTCGATGTCTGGG

GCGCAGGGACCACGGTCACCGTCTCCTCAGCCAAAACAACAGCCCCATC

GGTCTATCCACTGGCCCCTGTGTGTGGAGATACAACTGGCTCCTCGGTG

ACTCTAGGATGCCTGGTCAAGGGTTATTTCCCTGAGCCAGTGACCTTGA

CCTGGAACTCTGGATCCCTGTCCAGTGGTGTGCACACCTTCCCAGCTGT

CCTGCAGTCTGACCTCTACACCCTCAGCAGCTCAGTGACTGTAACCTCG

AGCACCTGGCCCAGCCAGTCCATCACCTGCAATGTGGCCCACCCGGCAA

GCAGCACCAAGGTGGACAAGAAAATTGAGCCCAGAGGGCCCACAATCAA

GCCCTGTCCTCCATGCAAATGCCCAGCACCTAACCTCTTGGGTGGACCA

TCCGTCTTCATCTTCCCTCCAAAGATCAAGGATGTACTCATGATCTCCC

TGAGCCCCATAGTCACATGTGTGGTGGTGGATGTGAGCGAGGATGACCC

AGATGTCCAGATCAGCTGGTTTGTGAACAACGTGGAAGTACACACAGCT

CAGACACAAACCCATAGAGAGGATTACAACAGTACTCTCCGGGTGGTCA

GTGCCCTCCCCATCCAGCACCAGGACTGGATGAGTGGCAAGGAGTTCAA

ATGCAAGGTCAACAACAAAGACCTCACAGCGCCCATCGAGAGAACCATC

TCAAAACCCAAAGGGTCAGTAAGAGCTCCACAGGTATATGTCTTGCCTC

CACCAGAAGAAGAGATGACTAAGAAACAGGTCACTCTGACCTGCATGGT

CACAGACTTCATGCCTGAAGACATTTACGTGGAGTGGACCAACAACGGG

AAAACAGAGCTAAACTACAAGAACACTGAACCAGTCCTGGACTCTGATG

GTTCTTACTTCATGTACAGCAAGCTGAGAGTGGAAAAGAAGAACTGGGT

GGAAAGAAATAGCTACTCCTGTTCAGTGGTCCACGAGGGTCTGCACAAT

CACCACACGACTAAGAGCCTCGCCCACTCTCCTGGTAAATGA
(SEQ ID NO: 3, CD6 heavy chain nucleic acid sequence)

CAAATTGTTCTCTCCCAGTCTCCAGCAATCCTGTCTGCATCTCCAGGGG

AGAAGGTCACAATGACTTGCAGGACCAGCTCAAGTGTAAGTTACATGCA

CTGGTACCAGCAGAAGCCAGGATCCTCCCCCAAACCCTGGATTTATGCC

ACATCCAACCTGGCTTCTGGAGTCCCTTTTCGCTTCAGTGGCAGTGGGT

CTGGGACCTCTTACTCTCTCACAATCAGCAGAGTGGAGGCTGAAGATGC

TGCCACTTATTACTGCCAGCAGTGGAATAGTAACCCACCCACGTTCGGA

GGGGGGACCAAGCTGGAAATAAAACGGGCTGATGCTGCACCAACTGTAT

CCATCTTCCCACCATCCAGTGAGCAGTTAACATCTGGAGGTGCCTCAGT

CGTGTGCTTCTTGAACAACTTCTACCCCAAAGACATCAATGTCAAGTGG

AAGATTGATGGCAGTGAACGACAAAATGGCGTCCTGAACAGTTGGACTG

ATCAGGACAGCAAAGACAGCACCTACAGCATGAGCAGCACCCTCACGTT

GACCAAGGACGAGTATGAACGACATAACAGCTATACCTGTGAGGCCACT

CACAAGACATCAACTTCACCCATTGTCAAGAGCTTCAACAGGAATGAGT

GTTAG
(SEQ ID NO: 4, CD6 light chain nucleic acid sequence).

One of skill in the art can readily use the genetic code to construct a variety of functionally equivalent nucleic acids, such as nucleic acids which differ in sequence but which encode the same antibody sequence, or encode a conjugate or fusion protein including the $V_L$ and/or $V_H$ nucleic acid sequence.

Nucleic acid sequences encoding the antibodies that specifically bind NA can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence or by polymerization with a DNA polymerase using the single strand as a template. One of skill would recognize that while chemical synthesis of DNA is generally limited to sequences of about 100 bases, longer sequences may be obtained by the ligation of shorter sequences.

Exemplary nucleic acids can be prepared by cloning techniques. Examples of appropriate cloning and sequencing techniques, and instructions sufficient to direct persons of skill through many cloning exercises are found in Sambrook et al., supra, Berger and Kimmel (eds.), supra, and Ausubel, supra. Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (Carlsbad, Calif.), and Applied Biosystems (Foster City, Calif.), as well as many other commercial sources known to one of skill.

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

A nucleic acid molecule encoding any of the antibodies, $V_H$ and/or $V_L$, or antibody fragment disclosed herein can be expressed in a recombinantly engineered cell such as bacteria, plant, yeast, insect and mammalian cells. These antibodies can be expressed as individual $V_H$ and/or $V_L$ chain, or can be expressed as a fusion protein. An immunoadhesin can also be expressed. Thus, in some examples, nucleic acids encoding a $V_H$ and $V_L$, and immunoadhesin are provided. The nucleic acid sequences can optionally encode a leader sequence.

To create a single chain antibody, (scFv) the $V_H$- and $V_L$-encoding DNA fragments are operatively linked to another fragment encoding a flexible linker, e.g., encoding the amino acid sequence $(Gly_4\text{-}Ser)_3$, such that the $V_H$ and $V_L$ sequences can be expressed as a contiguous single-chain protein, with the $V_L$ and $V_H$ domains joined by the flexible linker (see, e.g., Bird et al., Science 242:423-426, 1988; Huston et al., Proc. Natl. Acad. Sci. USA 85:5879-5883, 1988; McCafferty et al., Nature 348:552-554, 1990). Optionally, a cleavage site can be included in a linker, such as a furin cleavage site.

The nucleic acid encoding the $V_H$ and/or the $V_L$ optionally can encode an Fc domain. The Fc domain can be an IgA, IgM or IgG Fc domain. The Fc domain can be an optimized Fc domain, as described in U.S. Published Patent Application No. 20100/093979, incorporated herein by reference. In one example, the Fc is an $IgG_1$ Fc.

The single chain antibody may be monovalent, if only a single $V_H$ and $V_L$ are used, bivalent, if two $V_H$ and $V_L$ are used, or polyvalent, if more than two $V_H$ and $V_L$ are used. Bispecific or polyvalent antibodies may be generated that bind specifically to NA and another antigen. The encoded $V_H$ and $V_L$ optionally can include a furin cleavage site between the $V_H$ and $V_L$ domains.

It is expected that those of skill in the art are knowledgeable in the numerous expression systems available for expression of proteins including *E. coli*, other bacterial hosts, yeast, and various higher eukaryotic cells such as the COS, CHO, HeLa and myeloma cell lines. Once the expression vector is transferred to a host cell by conventional techniques, the transfected cells are then cultured by conventional techniques, such as to produce an antibody. Thus, host cells are provided containing a polynucleotide encoding an antibody or fragments thereof, or a heavy or light chain thereof, or portion thereof, or a single-chain antibody of the invention, operably linked to a heterologous promoter. In certain embodiments for the expression of double-chained antibodies, vectors encoding both the heavy and light chains may be co-expressed in the host cell for expression of the entire immunoglobulin molecule, as detailed below.

Mammalian cell lines available as hosts for expression of recombinant antibodies are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells, and a number of other cell lines. Different host cells have characteristic and specific mechanisms for the post-translational processing and modification of proteins and gene products. Appropriate cell lines or host systems can be chosen to ensure the correct modification and processing of the antibody or portion thereof expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, Hela, COS, MDCK, 293, 3T3, W138, BT483, Hs578T, HTB2, BT20 and T47D, NSO (a murine myeloma cell line that does not endogenously produce any functional immunoglobulin chains), SP2/0, CRL7030 and HsS78Bst cells. In one embodiment, human cell lines are of use. In one embodiment, the human cell line PER.C6 (Crucell, Netherlands) can be used. Additional cell lines which may be used as hosts for expression of recombinant antibodies include, but are not limited to, insect cells (e.g. Sf21/Sf9, *Trichoplusia ni* Bti-Tn5b1-4) or yeast cells (e.g. *S. cerevisiae, Pichia*, U.S. Pat. No. 7,326,681), plant cells (US Published Patent Application No. 20080066200); and chicken cells (PCT Publication No. WO2008142124).

The host cell can be a gram positive bacteria including, but not limited to, *Bacillus, Streptococcus, Streptomyces, Staphylococcus, Enterococcus, Lactobacillus, Lactococcus, Clostridium, Geobacillus*, and *Oceanobacillus*. Methods for expressing protein in gram positive bacteria, such as *Lactobacillus* are well known in the art, see for example, U.S. Published Patent Application No. 20100/080774. Expression vectors for *lactobacillus* are described, for example in U.S. Pat. No. 6,100,388, and U.S. Pat. No. 5,728,571. Leader sequences can be included for expression in *Lactobacillus*. Gram negative bacteria include, but not limited to, *E. coli, Pseudomonas, Salmonella, Campylobacter, Helicobacter, Flavobacterium, Fusobacterium, Ilyobacter, Neisseria*, and *Ureaplasma*.

One or more DNA sequences encoding the antibody or fragment thereof can be expressed in vitro by DNA transfer into a suitable host cell. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

The expression of nucleic acids encoding the isolated proteins described herein can be achieved by operably linking the DNA to a promoter (which is either constitutive or inducible), followed by incorporation into an expression cassette. The promoter can be any promoter of interest, including a cytomegalovirus promoter and a human T cell lymphotrophic virus promoter (HTLV)-1. Optionally, an enhancer, such as a cytomegalovirus enhancer, is included in the construct. The cassettes can be suitable for replication and integration in either prokaryotes or eukaryotes. Typical expression cassettes contain specific sequences useful for regulation of the expression of the DNA encoding the protein. For example, the expression cassettes can include appropriate promoters, enhancers, transcription and translation terminators, initiation sequences, a start codon (i.e., ATG) in front of a protein-encoding gene, splicing signal for introns, sequences for the maintenance of the correct reading frame of that gene to permit proper translation of mRNA, and stop codons. The vector can encode a selectable marker, such as a marker encoding drug resistance (for example, ampicillin or tetracycline resistance).

To obtain high level expression of a cloned gene, it is desirable to construct expression cassettes which contain, at the minimum, a strong promoter to direct transcription, a ribosome binding site for translational initiation (internal ribosomal binding sequences), and a transcription/translation terminator. For *E. coli*, this includes a promoter such as the T7, trp, lac, or lambda promoters, a ribosome binding site, and preferably a transcription termination signal. For eukaryotic cells, the control sequences can include a promoter and/or an enhancer derived from, for example, an immunoglobulin gene, HTLV, SV40 or cytomegalovirus, and a polyadenylation sequence, and can further include splice donor and/or acceptor sequences (for example, CMV and/or HTLV splice acceptor and donor sequences). The cassettes can be transferred into the chosen host cell by well-known methods such as transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding the antibody, labeled antibody, or functional fragment thereof, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982). One of skill in the art can readily use an expression systems such as plasmids and vectors of use in producing proteins in cells including higher eukaryotic cells such as the COS, CHO, HeLa and myeloma cell lines.

Modifications can be made to a nucleic acid encoding a polypeptide described herein without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps. In addition to recombinant methods, the antibodies, antigen binding fragments, and effector moieties such as labels of the present disclosure can also be constructed in whole or in part using standard peptide synthesis well known in the art.

Once expressed, the recombinant antigen binding fragments, antibodies, and/or effector molecules can be purified according to standard procedures of the art, including ammonium sulfate precipitation, affinity columns, column chromatography, and the like (see, generally, R. Scopes, PROTEIN PURIFICATION, Springer-Verlag, N.Y., 1982). The antibodies, antigen binding fragments and effector molecules (such as labels) need not be 100% pure. Once purified, partially or to homogeneity as desired, if to be used therapeutically, the polypeptides should be substantially free of endotoxin.

Methods for expression of antibodies and/or refolding to an appropriate active form, including single chain antibodies, from bacteria such as *E. coli* have been described and are well-known and are applicable to the antibodies disclosed herein. See, Buchner et al., *Anal. Biochem.* 205:263-270, 1992; Pluckthun, *Biotechnology* 9:545, 1991; Huse et al., *Science* 246:1275, 1989 and Ward et al., *Nature* 341:544, 1989.

Often, functional heterologous proteins from *E. coli* or other bacteria are isolated from inclusion bodies and require solubilization using strong denaturants, and subsequent refolding. During the solubilization step, as is well known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena et al., *Biochemistry* 9: 5015-5021, 1970, and especially as described by Buchner et al., supra.

Renaturation is typically accomplished by dilution (for example, 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. An exemplary yield is obtained when these two proteins are mixed in a molar ratio such that a 5-fold molar excess of one protein over the other is not exceeded. Excess oxidized glutathione or other oxidizing low molecular weight compounds can be added to the refolding solution after the redox-shuffling is completed.

In addition to recombinant methods, the antibodies, labeled antibodies and functional fragments thereof that are disclosed herein can also be constructed in whole or in part using standard peptide synthesis. Solid phase synthesis of the polypeptides of less than about 50 amino acids in length can be accomplished by attaching the C-terminal amino acid of the sequence to an insoluble support followed by sequential addition of the remaining amino acids in the sequence. Techniques for solid phase synthesis are described by Barany & Merrifield, *The Peptides: Analysis, Synthesis, Biology. Vol. 2: Special Methods in Peptide Synthesis, Part A*. pp. 3-284; Merrifield et al., *J. Am. Chem. Soc.* 85:2149-2156, 1963, and Stewart et al., *Solid Phase Peptide Synthesis*, 2nd ed., Pierce Chem. Co., Rockford, Ill., 1984. Proteins of greater length may be synthesized by condensation of the amino and carboxyl termini of shorter fragments. Methods of forming peptide bonds by activation of a carboxyl terminal end (such as by the use of the coupling reagent N, N'-dicylohexylcarbodimide) are well known in the art. Once an antibody molecule has been produced, it may be purified by any method known in the art for purification of an immunoglobulin molecule, for example, by chromatography (e.g., ion exchange, affinity, particularly by affinity for the specific antigens Protein A or Protein G, and sizing column chromatography), centrifugation, differential solubility, or by any other standard technique for the purification of proteins. Further, the antibodies or fragments thereof may be fused to heterologous polypeptide sequences (referred to herein as "tags") described above or otherwise known in the art to facilitate purification.

Compositions and Therapeutic Methods

Methods are disclosed herein for the prevention or treatment of an influenza infection. Prevention and treatment can include inhibition of infection with N1 subtype influenza viruses, such as, but not limited to circulating A(H1N1) pdm09 viruses, related viruses, any naturally emerging or engineered influenza viruses that contain the NA of an N1 subtype influenza virus, and the HA of a different subtype, including H2, H3, H5, H6, H7 or H10 subtypes. The methods can include administering to a subject a therapeutically effective amount of a monoclonal antibody, or an antigen binding fragment thereof, as disclosed above, or a nucleic acid encoding the antibody or antigen binding fragment. In some embodiments, the methods include contacting a cell with an effective amount of a monoclonal antibody, or antigen binding fragment thereof, that specifically binds NA of an N1 subtype influenza virus.

The disclosed antibodies, antigen binding fragments and nucleic acids can be used as emergency prophylaxis to protect individuals in the proximity of a developing influenza outbreak, or when encountering an increased risk of exposure. Thus, the methods can include selecting a subject at risk of exposure to influenza, such as a subject that is at particular risk, such as the elderly, a pediatric subject, an immunocompromised individual, a pregnant woman, a person with heart disease or a health care worker.

In other embodiments, methods are disclosed for ameliorating one or more symptoms associated with an influenza virus infection. Generally, the method includes administering an antibody or an antigen-binding fragment thereof that specifically binds NA. The method can include selecting a subject with an influenza virus infection, such as an N1 subtype influenza virus infection.

For treatment, the influenza virus infection does not need to be completely eliminated for the composition to be effective. The symptoms of the viral infection can be reduced, such as fever, cough, upper respiratory symptoms, and/or lower respiratory symptoms. In some embodiments, there is a shortened duration of symptoms. Thus, in some embodiments, the duration of symptoms is reduced by at least 10%, at least 20%, at least 50%, at least 60%, at least 70%, at least 80%, at least 90%, at least 95%, at least 98%, or 100%, as compared to the duration of symptoms in the absence of the composition. In some embodiments, a composition can decrease the infection in a population by a desired amount, for example by at least 10%, at least 20%, at least 50%, at least 60%, at least 70%, at least 80%, at least 90%, at least 95%, at least 98%, or 100%, as compared to the rate of infection in the absence of the composition. In addition, a composition can decrease viral titer by at least 10%, at least 20%, at least 50%, at least 60%, at least 70%, at least 80%, at least 90%, at least 95%, at least 98%, or 100% in a subject.

In one embodiment, administration of the antibody, antigen binding fragment (or nucleic acid encoding the antibody or antigen binding fragment) results in a reduction in the establishment of a virus infection and/or reducing subsequent disease progression in a subject. A reduction in the establishment of an infection, and/or a reduction in subsequent disease progression can encompass a statistically significant reduction in viral activity and/or replication. In some embodiments, methods are disclosed for treating a subject with an existing influenza virus infection. In other embodiments, methods are disclosed for preventing an influenza virus infection. These methods include administering to the subject a therapeutically effective amount of an antibody, or a nucleic acid encoding the antibody, thereby preventing or treating the viral infection. The method can prevent, delay or reduce symptoms of an influenza virus infection, such as fever, vomiting, body ache, sore throat, coughing, nasal congestion, headache, and fatigue.

A therapeutically effective amount of an N1 subtype NA-specific antibody or antigen binding fragment (or the nucleic acid encoding the antibody or antigen binding fragment), or nucleic acid, will depend upon the severity of the disease and/or infection and the general state of the patient's health. A therapeutically effective amount of the antibody can provide either subjective relief of a symptom(s) or an objectively identifiable improvement as noted by the clinician or other qualified observer. These compositions can be administered in conjunction with another therapeutic agent, either simultaneously or sequentially. For any application, the antibody, antigen binding fragment, or nucleic acid encoding the antibody or antigen binding fragment can be combined with additional anti-viral therapy.

In some embodiments, the subject is also administered an effective amount of an additional agent, such as anti-viral agent. The methods can include administration of one on more additional agents known in the art. The method can include administering a neuraminidase inhibitor (such as oseltamivir, or zanamivir). The method can include administering to the subject a therapeutically effective amount of an M2 inhibitor, such as amantadine and/or rimantadine. The method can include administering to the subject a therapeutically effective amount of peramivir. The subject can be hydrated and administered balancing electrolytes. The subject can be administered intravenous immuunoglobulins.

For prevention or treatment, the subject can also be administered a therapeutically effective amount of one or more additional antibodies or antigen binding fragments that specifically bind an influenza protein. The influenza protein can be an H1N1, H1N2, H2N2, H3N2, H5N1, H6N1, H7N2, H7N3, H7N7, H7N9, H9N2, H10N7 or H10N8 influenza A virus protein or may be an influenza B virus protein. In specific embodiments, the influenza protein can be an H1N1, H2N2, H3N2, H5N1 or H7N9 influenza virus protein. The influenza virus protein can be a NA or a HA. The influenza virus protein can be NA of an N1, N2, N3, N4, N5, N6, N7, N8, N9, N10 or N11 subtype influenza virus, or the HA of any influenza A subtype, H1-H18. The subject can be administered a therapeutically effective amount of more than one antibody, such as 1, 2, 3, 4, 5, 6, 7, 8, 9, or 10 antibodies with specificity for different influenza virus proteins. The subject can be administered a therapeutically effective amount of one or more antibodies that bind NA of a different (not N1) subtype influenza virus.

Thus, in some examples, the subject can be administered a therapeutically effective amount of one or more additional antibodies or antigen binding fragments that specifically binds either NA or HA of a specific influenza A virus, such as H1N1, H1N2, H2N2, H3N2, H5N1, H6N1, H7N2, H7N3, H7N7, H7N9, H9N2, H10N7 or H10N8. In additional non-limiting examples, the subject can be administered a therapeutically effective amount of one or more additional antibodies or antigen binding fragments that specifically binds NA of an H1N1, H2N2, H3N2, H5N1 or H7N9 influenza virus. In further non-limiting examples, the subject can be administered a therapeutically effective amount of one or more additional antibodies or antigen binding fragments that specifically binds HA of an H1N1, H2N2, H3N2, H5N1 or H7N9 influenza virus. In other non-limiting examples, the subject can also be administered a therapeutically effective amount of an antibody or antigen binding fragment that specifically binds HA (or NA) of H1N1, or a therapeutically effective amount of an antibody or antigen binding fragment that specifically binds HA (or NA) of H2N2, or a therapeutically effective amount of an antibody or antigen binding fragment that specifically binds HA (or NA) of H3N2, or a therapeutically effective amount of an antibody or antigen binding fragment that specifically binds HA (or NA) of H5N1, or a therapeutically effective amount of an antibody or antigen binding fragment that specifically binds HA (or NA) of H7N9 influenza virus.

In additional embodiments, the subject also can be administered an antibody or antibody binding fragment that specifically binds an epitope of NA of an N1 subtype influenza virus, wherein the epitope is not the epitope bound by CD6. In additional embodiments, the subject also can be administered an antibody or antibody binding fragment that specifically binds an epitope of NA of an H5N1 influenza virus.

In further embodiments, the subject also can be administered an antibody or antibody binding fragment that specifically binds an epitope of NA of an H7N9 influenza virus. In further embodiments, the subject also can be administered an antibody or antibody binding fragment that specifically binds an epitope of NA of N2, N3, N4, N5, N6, N7, N8, N9, N10, or an N11 subtype influenza virus.

In some embodiments the one or more additional antibodies or antigen binding fragments specifically bind HA, such as an HA from H1N1, H5N1, or H7N9. In additional embodiments, the subject also can be administered an antibody or antibody binding fragment that specifically binds an epitope of HA of H1N1 influenza virus. In further embodiments the subject also can be administered an antibody or antibody binding fragment that specifically binds an epitope of HA of an H5N1 influenza virus. In further non-limiting examples, the subject also can be administered an antibody or antibody binding fragment that specifically binds an epitope of HA of an H7N9 influenza virus. In further embodiments, the subject also can be administered an antibody or antibody binding fragment that specifically binds an epitope of HA of H1, H2, H3, H4, H5, H6, H7, H8, H9, H10, H11, H12, H13, H14, H15, H16, H17 or an H18 subtype influenza virus.

These embodiments and examples are not mutually exclusive. Thus, the subject can be administered 1, 2, 3, 4, 5, 6, 7, 8, 9 or 10 additional antibodies or antigen binding fragments that specifically bind an influenza virus protein. The antibodies can be administered in one or more pharmaceutical compositions. The antibodies can be administered in a single pharmaceutical composition. Thus, pharmaceutical compositions are provided herein that include the disclosed antibodies and/or antigen binding fragments and additional antibodies that specifically bind an influenza virus protein.

Single or multiple administrations of the compositions including the antibody, antigen binding fragment, or nucleic acid encoding the antibody or antigen binding fragment, that are disclosed herein, are administered depending on the dosage and frequency as required and tolerated by the patient. In any event, the composition should provide a sufficient quantity of at least one of the antibodies disclosed herein to effectively treat the patient. The dosage can be administered once but may be applied periodically until either a therapeutic result is achieved or until side effects warrant discontinuation of therapy. In one example, a dose of the antibody is infused for thirty minutes every other day. In this example, about one to about ten doses can be administered, such as three or six doses can be administered every other day. In a further example, a continuous infusion is administered for about five to about ten days. The subject can be treated at regular intervals, such as daily, until a desired therapeutic result is achieved. Generally, the dose is sufficient to treat or ameliorate symptoms or signs of disease without producing unacceptable toxicity to the patient.

Compositions are provided that include one or more of the antibody or antigen binding fragment that specifically bind NA and nucleic acids encoding these antibodies (and antigen binding fragments) that are disclosed herein in a carrier. As disclosed above, the compositions can include antibodies or antigen binding fragments that specifically bind an influenza virus protein.

In some embodiments, the composition includes a therapeutically effective amount of one or more additional antibodies or antigen binding fragments that specifically bind an influenza protein. The influenza protein can be an H1N1, H1N2, H2N2, H3N2, H5N1, H6N1, H7N2, H7N3, H7N7, H9N2, H10N7 or H10N8 influenza virus protein. In specific embodiments, the influenza protein can be an H1N1, H5N1 or H7N9 influenza A virus protein or an influenza B virus protein. The influenza virus protein can be a NA or a HA. Thus, in some embodiments, the subject is administered one or more of: an antibody or antigen binding fragment that specifically binds NA of an N2 subtype influenza virus, an antibody or antigen binding fragment that specifically binds NA of an N3 subtype influenza virus, an antibody or antigen binding fragment that specifically binds NA of an N4 subtype influenza virus, an antibody or antigen binding fragment that specifically binds NA of an N5 subtype influenza virus, an antibody or antigen binding fragment that specifically binds NA of an N6 subtype influenza virus, an antibody or antigen binding fragment that specifically binds NA of an N7 subtype influenza virus, an antibody or antigen binding fragment that specifically binds NA of an N8 subtype influenza virus, an antibody or antigen binding fragment that specifically binds NA of an N9 subtype influenza virus, an antibody or antigen binding fragment that specifically binds NA of an N10 subtype influenza virus, and an antibody or antigen binding fragment that specifically binds NA of an N11 subtype influenza virus. In specific non-limiting examples, the subject is administered an antibody that specifically binds of an N1 subtype influenza virus and/or a monoclonal antibody that specifically binds NA of an N9 subtype influenza virus.

Thus, compositions are provided that include an effective amount of one or more additional antibodies or antigen binding fragments that specifically binds either NA or HA of a specific influenza A virus, such as H1N1, H1N2, H2N2, H3N2, H5N1, H6N1, H7N2, H7N3, H7N7, H7N9, H9N2, H10N7, or H10N8. In additional non-limiting examples, the composition includes a therapeutically effective amount of one or more additional antibodies or antigen binding fragments that specifically binds NA of an H1N1, H5N1 or H7N9 influenza virus. In further non-limiting examples, the composition includes a therapeutically effective amount of one or more additional antibodies or antigen binding fragments that specifically binds HA of an H1N1, H5N1 or H7N9 influenza virus. In other non-limiting examples, the composition includes a therapeutically effective amount of an antibody or antigen binding fragment that specifically binds HA (or NA) of H1N1, an effective amount of an antibody or antigen binding fragment that specifically binds HA (or NA) of H2N2, an effective amount of an antibody or antigen binding fragment that specifically binds HA (or NA) of H3N2, an effective amount of an antibody or antigen binding fragment that specifically binds HA (or NA) of H5N1, or an effective amount of an antibody or antigen binding fragment that specifically binds HA (or NA) of H7N9 influenza virus.

In additional embodiments, the composition includes a therapeutically effective antibody or antibody binding fragment that specifically binds an epitope of NA of H1N1 influenza virus, wherein the epitope is not the epitope bound by CD6. In additional embodiments, the composition includes a therapeutically effective amount of an antibody or antibody binding fragment that specifically binds an epitope of NA of an H5N1 influenza virus. In further embodiments, the composition includes a therapeutically effective amount of an antibody or antibody binding fragment that specifically binds an epitope of NA of an H7N9 influenza virus.

In some embodiments the one or more additional antibodies or antigen binding fragments specifically bind HA, such as an HA from H1N1, H2N2, H3N2, H5N1, or H7N9.

In additional embodiments, the composition includes a therapeutically effective amount of an antibody or antibody binding fragment that specifically binds an epitope of HA of H1N1 influenza virus. In further embodiments the composition includes a therapeutically effective amount of an antibody or antibody binding fragment that specifically binds an epitope of HA of an H5N1 influenza virus. In further embodiments the composition includes a therapeutically effective amount of an antibody or antibody binding fragment that specifically binds an epitope of HA of an H2N2 influenza virus. In further embodiments the composition includes a therapeutically effective amount of an antibody or antibody binding fragment that specifically binds an epitope of HA of an H3N2 influenza virus. In further non-limiting examples, the composition includes a therapeutically effective amount of an antibody or antibody binding fragment that specifically binds an epitope of HA of an H7N9 influenza virus.

The compositions can be prepared in unit dosage forms for administration to a subject. The amount and timing of administration are at the discretion of the treating physician to achieve the desired purposes. The antibody and/or nucleic acid can be formulated for systemic or local administration. In one example, the antibody and/or nucleic acid is formulated for parenteral administration, such as intravenous administration. In some embodiments, administration is intramuscular. Compositions also can be formulated for intranasal administration as a liquid or an aerosol. In some embodiments, the antibody can be administered to the respiratory tract by using a nebulizer.

Active ingredients can also be entrapped in microcapsules prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980). Specifically, liposomes containing the immunogens or antibodies can be prepared by such methods as described in Epstein et al., Proc. Natl. Acad. Sci. USA, 82:3688 (1985); Hwang et al., Proc. Natl. Acad. Sci. USA, 77:4030 (1980); and U.S. Pat. Nos. 4,485,045 and 4,544,545. Liposomes with enhanced circulation time are disclosed in U.S. Pat. No. 5,013,556. The everse-phase evaporation method can be used with a lipid composition comprising phosphatidylcholine, cholesterol and PEG-derivatized phosphatidylethanolamine (PEG-PE). Liposomes are extruded through filters of defined pore size to yield liposomes with the desired diameter. Polypeptides such as antibodies or antibody fragments can be conjugated to the liposomes as described, for example, in Martin et al., J. Biol. Chem., 257:286-288 (1982) via a disulfide interchange reaction.

The compositions for administration can include a solution of the antibody that specifically binds NA, or an antigen binding fragment thereof, dissolved in a pharmaceutically acceptable carrier, such as an aqueous carrier. A variety of aqueous carriers can be used, for example, buffered saline and the like. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibodies or antigen binding fragments in these formulations can vary widely, and will be selected primarily based on fluid volumes, viscosities, body weight and the like in accordance with the particular mode of administration selected and the subject's needs. In some embodiments, administration is intravenous.

Controlled-release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995). Particulate systems include microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992).

Polymers can be used for ion-controlled release of the antibody compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. No. 5,055,303; U.S. Pat. No. 5,188,837; U.S. Pat. No. 4,235,871; U.S. Pat. No. 4,501,728; U.S. Pat. No. 4,837,028; U.S. Pat. No. 4,957,735; U.S. Pat. No. 5,019,369; U.S. Pat. No. 5,055,303; U.S. Pat. No. 5,514,670; U.S. Pat. No. 5,413,797; U.S. Pat. No. 5,268,164; U.S. Pat. No. 5,004,697; U.S. Pat. No. 4,902,505; U.S. Pat. No. 5,506,206; U.S. Pat. No. 5,271,961; U.S. Pat. No. 5,254,342 and U.S. Pat. No. 5,534,496).

A typical pharmaceutical composition for intravenous administration includes about 0.1 to 10 mg/kg of antibody (or antigen binding fragment) per day, or 0.5 to 15 mg/kg of antibody per day. Dosages from 0.1 up to about 100 mg/kg per subject per day may be used, particularly if the agent is administered to a secluded site and not into the circulatory or lymph system, such as into a body cavity or into a lumen of an organ. Exemplary doses include 1 to 10 mg/kg, such as 2 to 8 mg/kg, such as 3 to 6 mg/kg. Actual methods for preparing administrable compositions will be known or apparent to those skilled in the art and are described in more detail in such publications as *Remington's Pharmaceutical Science*, 19th ed., Mack Publishing Company, Easton, Pa. (1995).

Antibodies and antigen binding fragments may be provided in lyophilized form and rehydrated with sterile water before administration, although they are also provided in sterile solutions of known concentration. The antibody solution is then added to an infusion bag containing 0.9% sodium chloride, USP, and typically administered at a dosage of from 0.1 to 10 mg/kg or 0.5 to 15 mg/kg of body weight. Exemplary doses include 1 to 10 mg/kg, such as 2 to 8 mg/kg, such as 3 to 6 mg/kg. Considerable experience is available in the art in the administration of antibody drugs, which have been marketed in the U.S. since the approval of RITUXAN® in 1997. Antibodies and antigen binding fragments can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

A therapeutically effective amount of a nucleic acid encoding the antibody or an antigen binding fragment thereof can be administered to a subject in need thereof. One approach to administration of nucleic acids is direct immunization with plasmid DNA, such as with a mammalian expression plasmid. The nucleotide sequence encoding the antibody or fragment thereof can be placed under the control of a promoter to increase expression of the molecule. Immunization by nucleic acid constructs is well known in the art and taught, for example, in U.S. Pat. No. 5,643,578, and U.S. Pat. No. 5,593,972 and U.S. Pat. No. 5,817,637. U.S. Pat. No. 5,880,103 describes several methods of delivery of nucleic acids to an organism. The methods include liposomal delivery of the nucleic acids.

In another approach to using nucleic acids, an antibody or antigen binding fragment thereof can also be expressed by attenuated viral hosts or vectors or bacterial vectors, which can be administered to a subject. Recombinant vaccinia virus, adeno-associated virus (AAV), herpes virus, retrovirus, cytomegalovirus, poxvirus or other viral vectors can be used to express the antibody. For example, vaccinia vectors are described in U.S. Pat. No. 4,722,848. BCG (*Bacillus Calmette Guerin*) provides another vector for expression of the disclosed antibodies (see Stover, *Nature* 351:456-460, 1991).

In one embodiment, a nucleic acid encoding the antibody or an antigen binding fragment thereof is introduced directly into cells. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter.

Typically, the DNA is injected into muscle, although it can also be injected directly into other sites. Dosages for injection are usually around 0.5 mg/kg to about 50 mg/kg, and typically are about 0.005 mg/kg to about 5 mg/kg (see, e.g., U.S. Pat. No. 5,589,466).

In some examples, a subject is administered the DNA encoding the antibody or antibody binding fragments thereof to provide in vivo antibody production, for example using the cellular machinery of the subject. The subject can be administered DNA encoding other antibodies that specifically bind an influenza virus protein, see for example, the combinations of antibodies disclosed above Immunization by nucleic acid constructs is well known in the art and taught, for example, in U.S. Pat. No. 5,643,578, and U.S. Pat. No. 5,593,972 and U.S. Pat. No. 5,817,637. U.S. Pat. No. 5,880,103 describes several methods of delivery of nucleic acids encoding to an organism. The methods include liposomal delivery of the nucleic acids. Such methods can be applied to the production of an antibody, or antibody binding fragments thereof, by one of ordinary skill in the art.

One approach to administration of nucleic acids is direct administration with plasmid DNA, such as with a mammalian expression plasmid. The nucleotide sequence encoding the disclosed antibody, or antibody binding fragments thereof, and optionally other antibodies that specifically bind an influenza virus polypeptide, can be placed under the control of a promoter to increase expression.

In another approach to using nucleic acids, a disclosed antibody, or antibody binding fragments thereof can also be expressed by attenuated viral hosts or vectors or bacterial vectors. Recombinant vaccinia virus, adeno-associated virus (AAV), herpes virus, retrovirus, cytomegalovirus or other viral vectors can be used to express the antibody. For example, vaccinia vectors and methods useful protocols are described in U.S. Pat. No. 4,722,848. BCG (*Bacillus Calmette Guerin*) provides another vector for expression of the disclosed antibodies (see Stover, *Nature* 351:456-460, 1991).

In one embodiment, a nucleic acid encoding a disclosed antibody, or antibody binding fragments thereof, is introduced directly into cells. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter.

Typically, the DNA is injected into muscle, although it can also be injected directly into other sites. Dosages for injection are usually around 0.5 µg/kg to about 50 mg/kg, and typically are about 0.005 mg/kg to about 5 mg/kg (see, e.g., U.S. Pat. No. 5,589,466).

Detection Methods and Kits

A method is provided herein for the detection of the expression of NA, in vitro or in vivo. In one example, expression of NA is detected in a biological sample, and can be used to detect an infection with an N1 subtype influenza virus, such as, but not limited to, H1N1. Biological samples include sections of tissues, for example, frozen sections taken for histological purposes, tissue from biopsies, autopsies and pathology specimens. Biological samples also include body fluids, such as blood, serum, plasma, sputum, tears, saliva, spinal fluid, nasopharyngeal secretions or urine, or stool. The sample can be a nasal wash, a throat swab or a lung aspirate. In other embodiments, the sample is an environmental sample.

In one embodiment, methods are provided for detecting the presence of an influenza virus. The presence of the influenza virus is detected in a sample suspected of containing the virus, wherein the method includes contacting the sample with an antibody disclosed herein, or an antigen binding fragment thereof, and determining binding of the antibody or antigen binding fragment to the virus in the sample. In these methods, binding of the antibody or antigen binding fragment to virus in the sample is indicative of the presence of the virus in the sample. In one embodiment, the sample is a biological sample. The binding of the antibody or antigen binding fragment can be quantitated.

There are three genera of influenza virus (A, B, and C), all of which infect humans. Influenza A viruses are classified based on the viral surface proteins NA and hemagglutinin (HA). Eighteen HA subtypes (or serotypes) and eleven NA subtypes of influenza A virus have been identified. Specific influenza strain isolates can be identified by a standard nomenclature specifying virus type, geographical location where first isolated, sequential number of isolation, year of isolation, and HA and NA subtype. The serotypes that are known to have been associated with deaths are H1N1, H1N2, H2N2, H3N2, H5N1, H5N6, H7N7, H7N9, and H10N8.

In some embodiments, methods are disclosed herein for identifying an influenza virus as an N1 subtype virus, and/or distinguishing NA lineages within the N1 subtype, such as historical seasonal H1N1, current seasonal H1N1 and H5N1 lineages, and/or distinguishing an N1 subtype virus from other subtypes of influenza viruses, such as other influenza A viruses, such as an N2, N3, N4, N5 subtype influenza virus, N6 subtype influenza virus, N7 subtype influenza virus, N8 subtype influenza virus, N9 subtype influenza virus, N10 subtype influenza virus and/or an N11 subtype influenza virus. In a specific non-limiting example, the methods identify the virus as an N1 subtype influenza virus and/or distinguish the N1 subtype influenza virus from an N2 subtype influenza virus and/or an N7 subtype influenza virus. Thus, in some embodiments, the method distinguishes a particular influenza from other influenza viruses, such that it identifies and influenza virus as being an N1 subtype influenza virus.

The method includes contacting the sample with an antibody disclosed herein that specifically binds NA of an N1 subtype influenza virus, and determining binding of the antibody to the virus in the sample. In some embodiments, binding of the antibody to virus in the sample is indicative of the presence of an N1 subtype influenza virus in the sample. In one embodiment, the sample is a biological sample. In other embodiments, the sample is an environmental sample.

The methods can also include contacting the sample with an antibody or antigen binding fragment thereof that specifically binds HA of an H1, H2, H3, H4, H5, H6, H7, H8, H9, H10, H11, H12, H13, H14, H15, H16, H17 or H18 subtype influenza virus, and determining binding of the antibody to the virus in the sample. In some embodiments, binding of the antibody to virus in the sample is indicative of the presence of a particular subtype of influenza virus. In specific non-limiting examples, the monoclonal antibody or antigen binding fragment specifically binds H1, H2, H3 or H5, H6, H7 or H10.

In some embodiments, methods are disclosed herein for identifying an influenza virus as an H1N1 virus, and/or distinguishing an H1N1 virus from other influenza viruses, such as other influenza A viruses, such as an H1N2 virus, an H2N2 virus, an H3N2 virus, an H5N1 virus, an H6N1 virus, an H7N2 virus, an H7N3, an H7N7 virus, an H7N9 virus, an H9N2 virus, an H10N7 virus, and/or an H10N8 virus. Thus, in some embodiments, the method distinguishes a particular influenza from other influenza virus, such that it identifies and influenza virus as being an H1N1 influenza virus.

In several embodiments, a method is provided for detecting an N1 subtype influenza virus infection in a subject. The disclosure provides a method for detecting an N1 subtype influenza virus in a biological sample, wherein the method includes contacting a biological sample with the antibody or antigen binding fragment that specifically binds NA of an N1 subtype influenza virus, specifically the antibodies and antigen binding fragments disclosed herein, under conditions conducive to the formation of an immune complex, and detecting the immune complex, to detect the presence of a NA polypeptide in the biological sample. In additional embodiments, detection of the NA polypeptide in the sample detects or confirms a diagnosis of an N1 subtype influenza virus infection. In some embodiments, an antibody fragment, such as an Fv fragment, a Fab, or any of the antigen binding fragments disclosed above, can be utilized in the disclosed methods. The amount of N1 subtype influenza virus can be quantitated by methods known in the art.

The detection of NA of an N1 subtype influenza virus can be achieved, for example, by contacting a sample to be tested, optionally along with a control sample, with the antibody (or antigen binding fragment) under conditions that allow for formation of a complex between the antibody or antigen binding fragment and the virus. Complex formation is then detected (e.g., using an ELISA). The detection of the immune complex indicates that an N1 subtype influenza virus, such as A(H1N1)pdm09-virus, is present in the sample, and/or that the subject has an N1 subtype influenza virus infection. When using a control sample along with the test sample, complex is detected in both samples and any statistically significant difference in the formation of complexes between the samples is indicative of the presence of the N1 subtype influenza virus in the test sample. In some embodiments, the control is a standard value. In other embodiments, the control is the binding of the monoclonal antibody or antigen binding fragment to a control sample comprising a known quantity of neuraminidase. The control can also be the binding of the monoclonal antibody or antigen binding fragment to a control sample from a subject known not to have an influenza virus infection.

The methods can also include contacting the sample with an antibody or antigen binding fragment thereof that specifically binds HA of an H1, H2, H3, H4, H5, H6, H7, H8, H9, H10, H11, H12, H13, H14, H15, H16, H17 or H18 subtype influenza virus, and determining binding of the antibody to the virus in the sample. In some embodiments, binding of the antibody to virus in the sample is indicative of the presence of a particular subtype of influenza virus. In specific non-limiting examples, the monoclonal antibody or antigen binding fragment specifically binds H1, H2, H3 or H5. The method includes contacting a biological sample with the antibody or antigen binding fragment that specifically binds HA under conditions conducive to the formation of an immune complex, and detecting the immune complex, to detect the presence of a HA polypeptide in the biological sample. In some embodiments, the antibody or antigen binding fragment is labeled. In specific non-limiting examples the monoclonal antibody specifically binds HA of an H1 subtype influenza virus. Thus, the method can detect the presence of an H1N1 influenza virus and/or distinguish the presence of the H1N1 influenza virus from other influenza viruses. In other specific non-limiting examples the monoclonal antibody specifically binds HA of an H5 subtype influenza virus. Thus, the method can detect the presence of an H5N1 influenza virus and/or distinguish the presence of the H5N1 influenza virus from other influenza viruses.

In some embodiments, the disclosed antibodies can be used as standards in enzyme linked lectin assays (ELLA). An ELLA measures the ability of antibodies or pharmaceutical agents to inhibit NA activity. In the assay, a NA substrate, fetuin, is immobilized to the surface of wells of a protein-binding plate. NA is added to the substrate in the presence of different concentrations of antibody and incubated for a time period that allows the enzyme to cleave sialic acid from fetuin in control wells that do not contain antibody or NA inhibitors. Peanut agglutinin (PNA) conjugated to a label, such as, but not limited to, horse radish peroxidase is then added to the wells. The binding of PNA to molecules in the well that become exposed by the removal of sialic acid indicates how much neuraminidase activity is present. If antibodies inhibit this activity, the signal is in proportion to the amount of antibody present. In one example, the assay is used to measure the potency of NA-specific antibodies, derivatives of antibodies or other NA inhibitors, with the disclosed antibodies included in the ELLA as a reference standard.

In some embodiments, the disclosed antibodies are used to test vaccines. For example to test if a vaccine composition can induce NA inhibiting antibodies, such as, but not limited to, inhibition of NA of H1N1 influenza viruses. Thus provided herein is a method for testing a vaccine, wherein the method includes contacting a sample containing the vaccine, such as an NA polypeptide, or a recombinant attenuated virus, with the antibody (or antigen binding fragment) under conditions conducive to the formation of an immune complex, and detecting the immune complex. The detection of the immune complex confirm the vaccine will be effective. In one example, the detection of the immune complex in the sample indicates that the vaccine component, such as such as an NA antigen assumes a conformation capable of inducing neutralizing antibodies.

In some embodiments, an antibody (or antigen binding fragment) is directly labeled with a detectable label. In another embodiment, the antibody (or antigen binding fragment) that binds NA (the first antibody) is unlabeled and a second antibody or other molecule that can bind the antibody that binds NA is utilized. As is well known to one of skill in the art, a second antibody is chosen that is able to specifically bind the specific species and class of the first antibody. For example, if the first antibody is a human IgG, then the secondary antibody may be an anti-human-IgG. Other molecules that can bind to antibodies include, without limitation, Protein A and Protein G, both of which are available commercially.

Suitable labels for the antibody or secondary antibody are described above, and include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{125}I$, $^{131}I$, $^{35}S$ or $^{3}H$.

The immunoassays and method disclosed herein can be used for a number of purposes. Kits for detecting NA of an N1 subtype influenza virus will typically comprise an antibody (or antigen binding fragment) that specifically binds NA of an N1 subtype influenza virus, for example, any of the antibodies or antigen binding fragments disclosed herein. In some embodiments, an antibody fragment, such as an Fv fragment or a Fab is included in the kit. In a further embodiment, the antibody is labeled (for example, with a fluorescent, radioactive, or an enzymatic label).

In one embodiment, a kit includes instructional materials disclosing means of use. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment, the diagnostic kit comprises an immunoassay. Although the details of the immunoassays may vary with the particular format employed, the method of detecting the NA of an N1 subtype influenza virus in a biological sample generally includes the steps of contacting the biological sample with an antibody or antigen binding fragment which specifically bind, under immunologically reactive conditions, to NA of the N1 subtype influenza virus. The antibody is allowed to specifically bind under immunologically reactive conditions to form an immune complex, and the presence of the immune complex (bound antibody) is detected directly or indirectly. Methods for detection and quantification of NA are disclosed above.

The following examples are provided to illustrate certain particular features and/or embodiments. These examples should not be construed to limit the disclosure to the particular features or embodiments described.

EXAMPLES

H1N1 and H5N1 viruses are significant threats to public health, but antigenic epitopes of subtype N1 are not well characterized. The antigenic sites of the NA of a seasonal H1N1 virus, A/Brisbane/59/2007 (BR/07), were mapped and a site was identified that is conserved in the NA of seasonal H1N1, pH1N1 and H5N1 viruses. Prophylactic treatment with monoclonal antibodies (mAbs) specific for this antigenic site protected mice against lethal challenge with the homologous and heterologous N1-containing viruses, including pH1N1. However, these antibodies were less effective in inhibiting pH1N1 virus than the homologous virus (Wan, H. et al., *J Virol* 87, 9290-300 (2013)). mAbs against the NA of pH1N1 virus A/California/07/2009 (CA/09) were generated. The characterization of one of these mAbs, CD6, which is effective in inhibiting pH1N1 virus in both in vitro and in vivo studies, is disclosed below, with a focus on the crystallographic analysis of the CA/09 NA in complex with CD6 Fab. A unique epitope bridging neighboring NA monomers, with a large number of contacts between antibody and antigen is disclosed. This epitope is conserved amongst circulating pH1N1 viruses, and is a target for the development of novel therapeutics against influenza.

Example 1

Materials and Methods

Viruses.
Viruses used in this study include: pH1N1 viruses wildtype (wt) CA/09, CA/09-X179A, a high growth reassortant of CA/09 that has NA sequence identical to that of the wt parent virus, and a drug-resistant H1N1 virus A/Bethesda/

NIH107-D31/2009; seasonal H1N1 virus BR/07; an attenuated H5N1 VN/04 virus (ΔVN/04) that contains the HA and NA genes of VN/04 (polybasic residues in the cleavage motif of HA deleted) and the internal genes of A/Puerto Rico/8/1934; reassortant H6N1 viruses H6N1$_{CA/09}$, H6N1$_{BR/07}$, H6N1$_{VN/04}$ and H6N1$_{BA/12}$, viruses that contain the HA gene of H6N2 virus A/Turkey/Massachusetts/3740/1965 and the NA gene of CA/09, BR/07, VN/04 or BA/12; $H6N1_{CA/09}$ viruses, which contain N369K or D451G single mutation in the NA. Viruses were grown in 10-day-old embryonated chicken eggs and, if necessary, were inactivated with β-propiolactone (Sigma-Aldrich, St. Louis, Mo., USA) and purified by sucrose gradient centrifugation.

Generation of Mouse Hybridomas Secreting NA-Specific mAbs.

Hybridomas were generated as previously described (Wan, H. et al. *J Virol* 87, 9290-300 (2013)). Briefly, female BALB/c mice (6-week-old, The Jackson Laboratory, Bar Harbor, Me., USA) were immunized and boosted with CA/09. Splenocytes from an immunized mouse were fused with Sp2/0 cells. Hybridomas were screened in cell-based ELISA with NA expressed on 293T cells transfected with pCAGGS-CA/09NA, a plasmid that contains the NA gene of CA/09 Easterbrook, J. D. et al. *Virology* 432, 39-44 (2012)). Positive hybridomas were subcloned twice by limiting dilution. Antibodies were purified from serum-free tissue culture supernatants using protein G columns (GE Healthcare, Uppsala, Sweden) and isotyped with the Pierce rapid isotyping kit (Pierce Biotechnology, Rockford, Ill., USA). The H and L chain genes of mAb CD6 were sequenced by ProMab Biotechnologies, Inc. (Albany, Calif., USA) and Syd Labs, Inc. (Malden, Mass., USA).

Preparation of Fab and Fab2.

Purified IgG (1 mg) was digested to Fab and Fc fragments by exposure to 40 μg activated papain (Sigma-Aldrich, St. Louis, Mo., USA) in a solution containing 10 mM cysteine, 100 mM sodium acetate pH 5.5, 125 μM EDTA for 2-4 h at 37° C. Fab2 was produced by digestion with pepsin (Sigma-Aldrich, St. Louis, Mo., USA) for 2-4 h at 37° C. Fab and Fab2 fragments were subsequently separated from Fc by affinity chromatography using a protein A HI-TRAP™ column (GE Healthcare, Uppsala, Sweden) and purified to homogeneity by size exclusion chromatography (SEC) (Tong, S. et al. *PLoS Pathog* 9, e1003657 (2013)). SDS-PAGE was performed to confirm the sizes of Fab and Fab2. The NATIVEPAGE™ Novex Bis-Tris gel, SIMPLYBLUE™ SafeStain staining solution and protein standard were purchased from Invitrogen, Inc. (Carlsbad, Calif., USA).

CA/09 NA Expression and Purification.

Recombinant CA/09 NA protein was expressed in a baculovirus expression system with an additional N-terminal cassette containing a His-tag, a tetramerization domain from the human vasodilator-stimulated phosphoprotein and a thrombin cleavage site (Xu, X., et al. *J. Virol.* 82, 10493-10501 (2008)). Secreted protein was recovered from the culture supernatant and purified by metal affinity chromatography and SEC. For structural analyses, the protein was further subjected to thrombin cleavage and SEC.

Formation and Purification of the CD6 Fab/NA Complex.

CD6 Fab was mixed with purified, His-tag depleted, recombinant CA/09 NA monomer at a 1:1 molar ratio of Fab to NA. The resulting CD6 Fab/NA complex was purified away from unbound substrates by SEC in a buffer comprising 50 mM Tris-HCl (pH 8.0), 150 mM NaCl. The CD6 Fab/NA complex eluted as a single peak between the 158 kD and 670 kD molecular weight markers and was concentrated to 15 mg $ml^{-1}$ for subsequent crystallization trials.

Crystallization and data collection of the CD6 Fab/NA complex. Initial sparse-matrix crystallization screening was carried out using a TOPAZ™ Free Interface Diffusion (FID) Crystallizer system (Fluidigm Corporation, San Francisco, Calif.). Hits were obtained after 24 hours in several conditions containing the precipitant polyethylene glycol (PEG) variables. Following optimization and translation to sitting drop vapor diffusion, diffraction quality crystals were obtained at 23° C. against a reservoir containing 0.09 M malonic acid, 0.013M ammonium citrate tribasic, 0.006 M succinic acid, 0.015 M DL-malic acid, 0.02 M sodium acetate, 0.025 M sodium formate, 0.008 M ammonium tartrate dibasic, 0.1M HEPES:NaOH, and 10% (w/v) PEG 8000, final pH 7.0 (condition 68 from the MCSG-3 screen, Microlytic North America). The CD6 Fab/NA complex dataset was collected from a single crystal to 2.8 Å resolution at the Advanced Photon Source (APS) SER CAT 22-ID beamline (wavelength 1.0 Å). Data were processed with DENZO-SCALEPACK suite (Otwinowski, Z. & Minor, W. Scalepack Manual. (1997)).

Structure Determination and Refinement.

The CD6 Fab/NA complex structure was determined at 2.8 Å resolution by the molecular replacement method using Phaser (McCoy, A. J. et al., *Acta Crystallogr D Biol Crystallogr* 61, 458-64 (2005)). A strong solution was obtained for the NA component of the complex using a single monomer of NA (PDB: 4B7M) (van der Vries, E. et al. *PLoS Pathog* 8, e1002914 (2012). An initial search for CD6 Fab determined the position of the variable (Fv) domains using the Fv component of a mouse $IgG_1$ Fab (PDB: 1WEJ (Mylvaganam, S. E. et al., *J Mol Biol* 281, 301-22 (1998)) as a search model. A subsequent search using the constant (Fc) domains of a mouse $IgG_{2a}$ Fab (PDB: 3FO9) Zhu, X. et al., *J Am Chem Soc* 131, 18206-7 (2009)) located the Fc region. Two NA monomers and two Fabs occupy the asymmetric unit.

Rigid-body and restrained refinement of the molecular replacement solution was carried out using REFMAC5 (CCP4. The CCP4 suite: programs for protein crystallography. *Acta Crystallogr D Biol Crystallogr* 50, 760-3 (1994)) and model building was performed in Coot (Emsley, P. & Cowtan, K. *Acta Crystallogr D Biol Crystallogr* 60, 2126-32 (2004)). $2F_o$-$F_c$ electron density was well defined throughout the model. Restrained refinement of the structure was completed in REFMAC5 using TLS refinement (Winn, M. D. et al. *Acta Crystallogr D Biol Crystallogr* 57, 122-33 (2001)). The final model was assessed using MolProbity (Davis, I. W. et al. *Nucleic Acids Res* 35, W375-83 (2007)). In the final model, 95% of the residues were in favored regions of Ramachandran plot, with 5% in additional allowed regions.

Plaque Assay.

Confluent MDCK cells in 6-well plates were inoculated with diluted virus. After 1 hour (h) incubation at 37° C., cells were overlaid with agar supplemented with mAb at indicated concentrations. Cells inoculated with virus and overlaid with agar without mAb were set up as controls. When examining the effect of antibody CD6 on virus entry, CA/09 virus was pre-mixed with CD6 and incubated for 1 h at 37° C. before inoculation of cells. After 1 h incubation of cells with the inoculum, cells were washed with PBS to remove CD6, and then covered with agar without antibody. On day 3 post virus inoculation, cells were stained with crystal violet solution to visualize plaques.

Site-Directed Mutagenesis.

Nucleotide changes corresponding to a panel of single amino mutations and a double mutation were introduced into the CA/09 NA gene in pCAGGS-CA/09NA plasmid with QUICKCHANGE® multisite-directed mutagenesis kit (Stratagene, La Jolla, Calif., USA). Mutant plasmids were sequenced to verify the presence of introduced mutations and the absence of additional, unwanted mutations.

Cell-Based ELISA.

CA/09 NA and its mutants were expressed on 293T cells by transfecting with wt or mutant pCAGGS-CA/09NA plasmids using LIPOFECTAMINE™ 2000 reagent (Invitrogen, Grand Island, N.Y., USA). ELISA was performed with the transfected cells as described previously (Wan, H. et al. *J Virol* 87, 9290-300 (2013)). Hyperimmune mouse serum against CA/09-X179A virus (with hemagglutination inhibition titer ≥320) was used as a positive control and for examining the expression of NA. In assays to identify critical amino acids for mAb binding, mutations (W375A, W375G and N378A) that resulted in the absence of binding by mouse serum ($OD_{490}$<0.3) were not included in further analysis. For all other NAs (mutant and wt), the signals generated by mAb binding to each NA were normalized to those generated by mouse serum (the background signals generated with mock transfected cells were subtracted from both the mAb and mouse serum signals) and therefore expressed as relative binding.

Enzyme-Linked Lectin Assay (ELLA).

The inhibition of NA enzyme activity by mAbs was measured by ELLA in a 96-well plate format (Couzens, L. et al. *J Virol Methods* 210C, 7-14 (2014)). Briefly, mixtures of virus and serial dilutions of antibody were incubated in duplicate wells of a fetuin-coated plate. After overnight incubation at 37° C. the plates were washed and then incubated with peanut agglutinin conjugated to horse radish peroxidase. After 2 h incubation at room temperature, the plates were washed and substrate added. The reaction was stopped 10 min later and the optical density read at 490 nm. The $IC_{50}$ was determined by quadratic curve fitting (GraphPad PRISM®).

Selection of mAb Escape Variants and Identification of NA Mutations.

Escape variants were selected as previously reported (Wan, H. et al. *J Virol* 87, 9290-300 (2013); Gerhard, W. & Webster, R. G. *J Exp Med* 148, 383-92 (1978)). mAb CD6 was mixed with $10^6$ plaque forming units of $H6N1_{CA/09}$ virus and inoculated into 10-day-old embryonated chicken eggs. This reassortant virus was elected for generation of escape variants in order to keep the consistence of using H6 reassortant viruses in subsequent ELLA. As the initial selection did not result in escape variants that resisted inhibition by CD6 in plaque assay, further selections were performed. Briefly, allantoic fluid (P1) from the initial selection was pooled and inoculated into eggs to allow the expansion of residual parent virus (if any) and potential variants. Allantoic fluid collected from these eggs (P2) was pooled, mixed with mAb CD6 and inoculated into eggs again. This process was repeated 2 more times, and the resultant P5 allantoic fluid was collected from individual eggs and tested in plaque assay. Three large plaques that formed in the presence of CD6 were picked and expanded in eggs. P6 viruses (expanded from each single plaque) were characterized and sequenced. The NA gene was amplified by RT-PCR[49] and PCR products were sequenced.

Prophylactic and Therapeutic Studies.

All mouse studies followed approved protocols. Female DBA/2 mice (7-week-old, 5/cage) were received from The Jackson Laboratory (Bar Harbor, Me., USA) and housed with food and water supplied ad libitum. Cages were randomly assigned to experimental groups composed of 15 mice, a number adequate to demonstrate differences in survival (n=10) and lung virus titers (n=5). To examine the prophylactic efficacy of CD6, mAb was administered i.p. 12 h before intranasal challenge with 10 $LD_{50}$ of CA/09-X179A. On day 3 p.c., 5 mice in each group were euthanized and the lungs were collected for virus titration in MDCK cells. To examine the therapeutic efficacy, groups of DBA/2 mice (n=10) were treated with CD6 after virus infection. In all experiments body weight and mortality were monitored for up to 14 days p.c. Mice that were moribund or lost ≥25% weight were euthanized. The persons monitoring experimental animals but not the primary investigator were blinded to group allocation.

Phylogenetic Analyses.

pH1N1 NA gene sequences available from the GISAID Epiflu database (gisaid.org) excluding duplicates, those without full dates of collection or propagated in eggs (n=7958) were aligned using MAFFT (Katoh, K. et al., *Methods Mol Biol* 537, 39-64 (2009)). Neighbor-joining phylogenetic tree of all pH1N1 NA genes was constructed in MEGA version 5 using Tamura-Nei nucleotide substitutions model (Tamura, K. et al. *Mol Biol Evol* 28, 2731-9 (2011)). For Bayesian molecular clock analysis, a random sampling of 10 viruses per year since 2009 were added to a subset of viruses with mutations at NA amino acid residues 95, 449 or 451 and the current vaccine strain, CA/09, for a final dataset of 182 taxa. Temporal phylogenies were inferred using a log normal distribution relaxed molecular clock with the SRD06 substitution model in BEAST v1.7.0 using Bayesian ancestral state reconstruction (Drummond, A. J. et al., *Mol Biol Evol* 29, 1969-73 (2012). Chain lengths of 150 million steps were used with a 10% burn-in removed in two independent runs.

Example 2

Functional Characteristics of pH1N1 NA-Specific mAb CD6

Hybridomas secreting mAbs CD6 and HF5 were established through a fusion of Sp2/0 myeloma cells and splenocytes from a mouse immunized with CA/09. Both mAbs are of IgG2a isotype. The NA specificity of the mAbs was confirmed with cell-based ELISA, using 293T cells transiently expressing the NA of CA/09 as antigen (Wan, H. et al. *J Virol* 87, 9290-300 (2013)).

In ELISA using virus-coated plates, both mAbs bound CA/09, but did not bind a seasonal H1N1 virus BR/07, or the attenuated H5N1 virus A/Vietnam/1203/2004 (ΔVN/04). Binding to recombinant NA was not measurable in kinetic binding analyses using a BioLayer Interferometry (BLI) Octet Red system (Fortebio Inc.). The affinity (Kd) of CD6 measured by real time binding to recombinant CA/09 NA was ≈95 nM. Both CD6 and HF5 antibodies blocked NA activity in an enzyme-linked lectin assay (ELLA), resulting in decreased cleavage of fetuin by CA/09 NA (FIGS. 1A and 1B), with median inhibition concentrations ($IC_{50}$) of 44 and 26 ng ml$^{-1}$, respectively. In plaque assays with Madin-Darby canine kidney (MDCK) cells, both mAbs significantly reduced CA/09 plaque size (FIG. 1C). While the two antibodies were specific for CA/09 NA and did not reduce enzyme activity or plaque size of BR/07, CD6 inhibited the NA activity of VN/04 to a low but measurable degree at high concentrations in ELLA (FIG. 1A). Similarly, there was a slight reduction in the size of plaques formed by ΔVN/04 virus in the presence of CD6, but not HF5 (FIG. 1C).

Example 3 mAb CD6 is an Effective Prophylactic and Therapeutic Agent in Mice

Figure 4B:
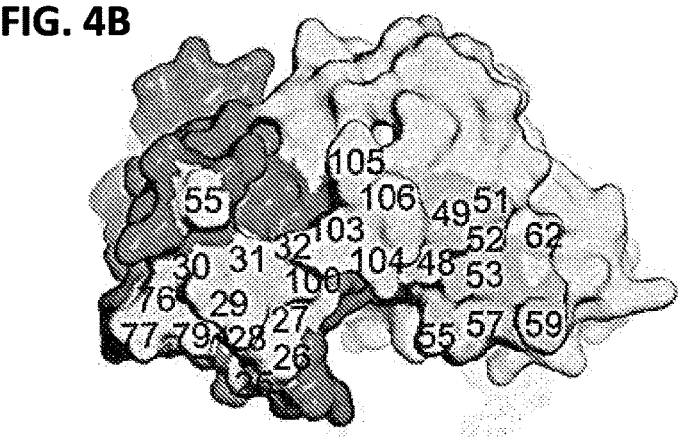

As mAb HF5 failed to bind recombinant NA, the characterization of CD6 was the primary focus, and HF5 was included in some assays as control. To evaluate the potential of mAb CD6 to protect against influenza, weight loss and survival of DBA/2 mice infected with 10 median lethal doses ($LD_{50}$) of CA/09-X179A, either before or after CD6 treatment, was monitored. In the prophylactic experiments, CD6 was administered intraperitoneally (i.p.) to groups of 15 mice 12 h before virus challenge. Mouse mAb 3A2 that is specific for the NA of seasonal H1N1 virus BR/07[15] was used as control. A single dose of CD6 at ≥0.5 mg $kg^{-1}$ protected all mice from death (FIG. 2A) and resulted in <12% weight loss (FIG. 8A). In contrast, the control mAb did not protect against weight loss or death. As expected, CD6 did not prevent infection, but resulted in significant reduction of lung virus titers that was proportional to the dose of mAb administered (FIG. 8B).

CD6 was also an effective therapeutic treatment for mice infected with CA/09-X179A (10 $LD_{50}$). A single dose of 5 mg $kg^{-1}$ given on day 1 post challenge (p.c.) protected all mice against death and weight loss (FIG. 2B and FIG. 8C). Protection was dependent on the time of mAb treatment, with administration of the same dose on either day 2 or day 3 p.c. resulting in survival of 40% and 20% of mice, respectively. None of the mice survived when the antibody was administered 4 days after infection. The therapeutic effectiveness of CD6 was also dependent on dose—while treatment with 5 mg $kg^{-1}$ on day 1 p.c. protected all mice against death, only 70% and 20% of mice treated with 2.5 and 1 mg $kg^{-1}$ respectively, survived. Survival at these low antibody doses was increased by repeat administration of mAb; 90% of mice survived when treated daily (on days 1, 2, 3 and 4 p.c.) with 2.5 or 1 mg $kg^{-1}$ CD6 (FIG. 2C). The daily treatment with low CD6 doses only had a small impact on weight loss (FIG. 8D).

Example 4

The CD6 Epitope is at the Interface of Adjacent NA Monomers

Structural analysis provides the only means to fully elucidate an antibody epitope and to identify the interactions that contribute to antibody binding. The crystal structure of the CD6 Fab and CA/09 NA (CD6 Fab/NA) complex was determined at 2.8 Å resolution. The purification, crystallization and refinement of CD6 Fab/NA complex are described in the methods, and statistics for data processing and refinement are presented in Table 1.

TABLE 1

Data collection and refinement statistics

| | CD6-CA/09 NA |
|---|---|
| Data collection | |
| Space group | C222 |
| Cell dimensions | |
| a, b, c (Å) | 141.74, 195.78, 141.92 |
| α, β, γ (°) | 90, 90, 90 |
| Resolution (Å) | 50-2.80 (2.87-2.80)[a] |
| $R_{sym}$ or $R_{merge}$ | 0.143 (0.521) |
| I/σI | 18.1 (4.4) |
| Completeness (%) | 93.5 (99.1) |
| Redundancy | 4.7 (5.0) |
| Refinement | |
| Resolution (Å)[b] | 50-2.80 (2.87-2.80) |
| No. reflections | 46132 |
| $R_{work}/R_{free}$ | 0.181/0.224 |
| No. atoms | |
| Protein | 12635 |
| Ligand/ion | 116 |
| Water | 181 |
| B-factors | |
| Protein | 48.1 |
| Ligand/ion | 82.0 |
| Water | 40.1 |
| r.m.s. deviations | |
| Bond lengths (Å) | 0.013 |
| Bond angles (°) | 1.60 |

[a]Values in parentheses are for highest-resolution shell.

[b]A single crystal was used for both structure determination at 2.8 Å resolution and refinement.

Comparison with NA structures previously reported (Li, Q. et al. *Nat Struct Mol Biol* 17, 1266-8 (2010); Amaro, R. E. et al. *Nat Commun* 2, 388 (2011); van der Vries, E. et al. *PLoS Pathog* 8, e1002914 (2012)) suggests that the binding of CD6 does not induce any major conformation changes to the CA/09 NA structure. While the 150-loop of the active site of pH1N1 NA has been reported in both an open and closed conformation (Amaro et al., supra; van der Vries et al., supra) in this Fab/NA complex structure, the CA/09 NA 150-loop adopts the reported open conformation. Additional positive electron density was observed at 3 of the 4 potential N-linked glycosylation sites Asn88, Asn146 and Asn235. Nine sugar residues were manually fitted into the density at these positions. These glycosylated sites are not within the CD6 epitope.

To date, three epitopes on NA have been structurally characterized, two from N9 NA-Ab complexes (Tulip, W. R. et al. *J Mol Biol* 227, 122-48 (1992); Malby, R. L. et al. *Structure* 2, 733-46 (1994)) and one from a N2 NA-Ab complex (Venkatramani, L. et al. *J Mol Biol* 356, 651-63 (2006)). Similar to these complexes, four CD6 Fabs bind to one NA tetramer. However, the CD6 epitope is novel, forming an antibody footprint that bridges two adjacent monomers in the NA tetramer (FIG. 3A). The CD6 heavy (H) and light (L) chains both contribute to the antibody footprint (FIG. 3B). Altogether there are 30 amino acids within NA that are in contact with the antibody. The H chain of CD6 Fab makes the majority of the antigen-antibody contacts, and forms a bridge between the neighboring NA monomers. The area on each monomer that is buried by CD6 was calculated by PISA (Krissinel, E. & Henrick, K. *J Mol Biol* 372, 774-97 (2007)) as 187 $Å^2$ and 528 $Å^2$ (FIG. 4A).

A large surface area of H and L chains (497 Å$^2$ and 392 Å$^2$) is buried (FIG. 4B) and, as for other NA-Fab complexes, the interacting faces of antigen and antibody show excellent shape complementarity.

The residues on the HCDR1 loop form multiple interactions with residues of one NA monomer: Pro93, Val94, Ser95, Trp358, Trp375, Ser388, Ile389, Asn449, Ser450 and Asp451 (Table 2 and FIG. 9A).

TABLE 2

Contacts between buried surface residues of CD6 and CA/09 NA

| NA monomer A | NA monomer B | Type of contact | Light chain | Heavy chain |
|---|---|---|---|---|
| Pro93 | | Hydrophobic | | Thr31 |
| | | Hydrophobic | | Ser55 |
| Val94 | | Hydrophobic | | Thr28 |
| | | Water | | Asn30 |
| | | Hydrophobic | | Thr31 |
| Ser95 | | Hydrophobic | | Thr28, Thr31, Tyr32 |
| | Ile216 | Hydrophobic | | Tyr106 |
| | Lys217 | Water | | Tyr104 |
| | Trp219 | Hydrogen bond | Ser55 | |
| | Arg220 | Hydrogen bond | Val57 | |
| | | Hydrophobic | Phe59 | |
| | Asn221 | Hydrogen bond | Ser55 | |
| | Gln250 | Hydrophobic | Phe59 | |
| | Ala251 | Hydrophobic | Phe59 | |
| | Ser252 | Hydrophobic | Phe59 | |
| | Lys254 | Water | Tyr48 | Tyr104 |
| | | Hydrophobic | Asn52 | |
| | Lys262 | Hydrophobic | | Tyr105 |
| | Ile263 | Hydrophobic | | Tyr105/Tyr106 |
| | Val264 | Hydrophobic | | Tyr105/Tyr106 |
| | Lys265 | Hydrophobic | | Tyr106 |
| | Ser266 | Hydrophobic | Ala49 | Tyr106 |
| | | Water | Asn52 | |
| | | Hydrogen | | |
| | Val267 | Hydrophobic | Ser51 | |
| | Glu268 | Hydrogen | Ser51 | |
| | | Hydrophobic | Asn52 | |
| | | Hydrogen | Leu53 | |
| | Asn270 | Hydrophobic | Ser62 | |
| Asn355 | | Hydrophobic | | Ser77 |
| Trp358 | | Hydrophobic | | Thr28 |
| Trp375 | | Water | | Phe29 |
| | | Water | | Ser79 |
| | | Hydrophobic | | Phe27 |
| | | Hydrophobic | | Thr28 |
| | | Hydrophobic | | Asn30 |
| Pro377 | | Hydrophobic | | Ser77 |
| | | Hydrophobic | | Asp76 |
| Asn378 | | Hydrophobic | | Ser77 |
| Ser388 | | Hydrogen | | Gly26 |
| | | Hydrogen | | Ser79 |
| | | Hydrophobic | | Ser25 |
| | | Hydrophobic | | Gly26 |
| | | Hydrophobic | | Phe27 |
| Ile389 | | Hydrophobic | | Gly26 |
| | | Hydrophobic | | Phe27 |
| | | Hydrophobic | | Thr28 |
| Asn449 | | H bond | | Thr31 |
| | | Hydrophobic | | Thr31 |
| | | Hydrophobic | | Ile103 |
| Ser450 | | Hydrophobic | | Ile103 |
| Asp451[a] | | H bond | | Tyr104 |
| | | Water | | Arg100 |
| | | Hydrophobic | | Tyr104 |

[a]Asp451 forms an H-bond with Thr215 of the neighboring NA monomer.

Figure 4C:
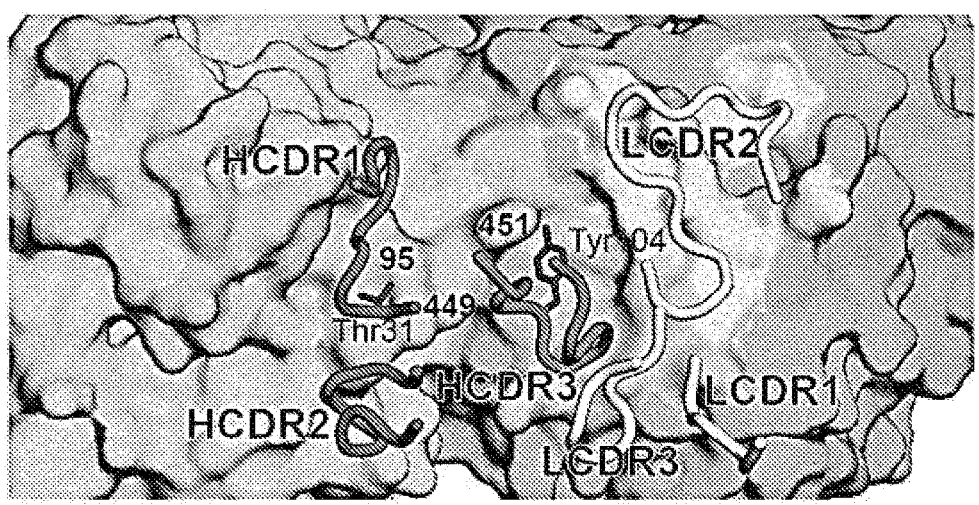
Figure 8A:
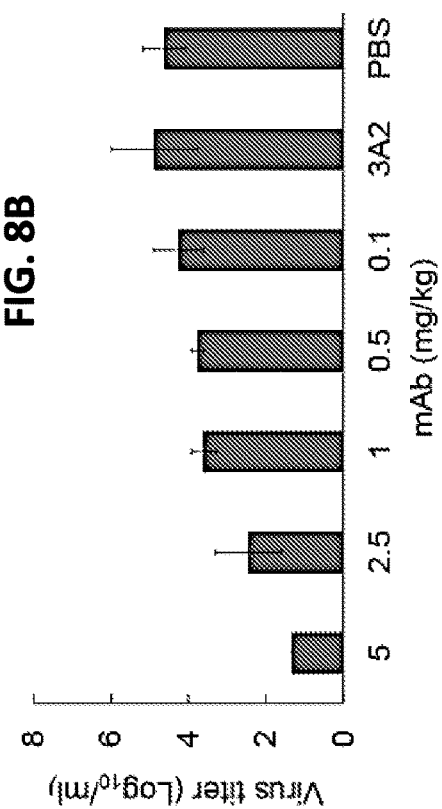
FIGS. 8A-8D. Clinical and virologic evidence of CD6 efficacy in prophylactic and therapeutic studies. (8A) Weight loss of mice (n=10) in prophylactic studies. Female DBA/2 mice were injected i.p. with mAb CD6 12 h before challenge with 10 LD$_{50}$ of CA/09-X179A. The survival curves are shown in FIG. 2A. (8B) Lung virus titers of mice (n=5) in prophylactic studies. Mice were treated with CD6 and infected as described in (8A) and then euthanized on day 3 p.c. The lungs were collected and homogenized for virus titration in MDCK cells. The dotted line denotes the detection limit (2.2 Log$_{10}$ TCID$_{50}$ ml$^{-1}$). A titer of 1.7 Log$_{10}$ TCID$_{50}$ ml$^{-1}$ was arbitrarily set to represent titers below the detection limit. (8C) Weight loss of mice (n=10) in single dose therapeutic studies. Female DBA/2 mice were infected intranasally with 10 LD$_{50}$ of CA/09-X179A and 5 mg kg$^{-1}$ of mAb CD6 was administered i.p. 1, 2, 3 or 4 days later. (8D) Weight loss of mice (n=10) treated therapeutically with single or multiple doses of CD6. As described for (8C), DBA/2 mice were infected with CA/09-X179A and treated with either 2.5 or 1 mg kg$^{-1}$ CD6 24 h later (d1) only or once daily (24 h intervals) for 4 days (d1-4). The survival curves for these experiments are shown in FIGS. 2B and 2C.
Figure 8B:
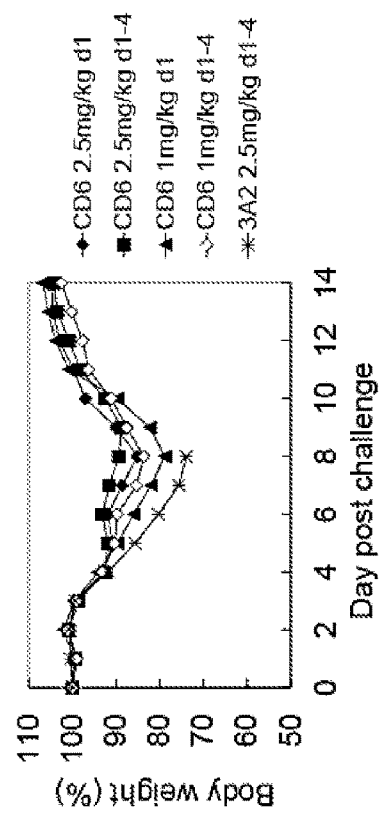
Figure 8C:
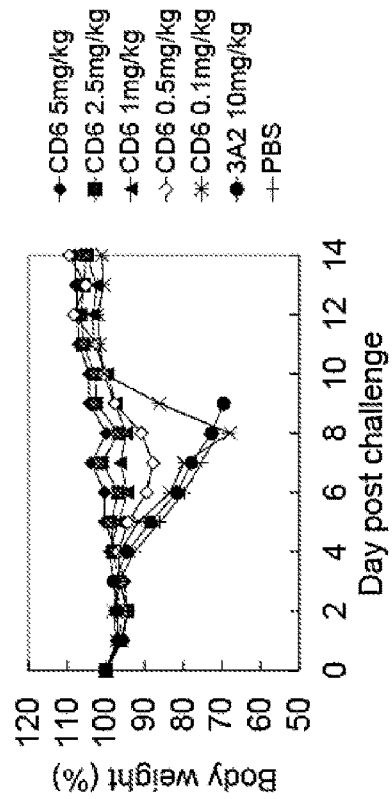
Figure 8D:
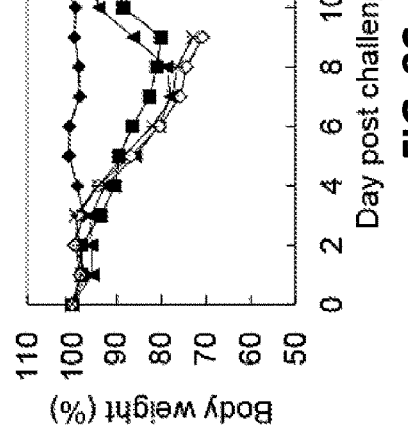
Figure 9A:
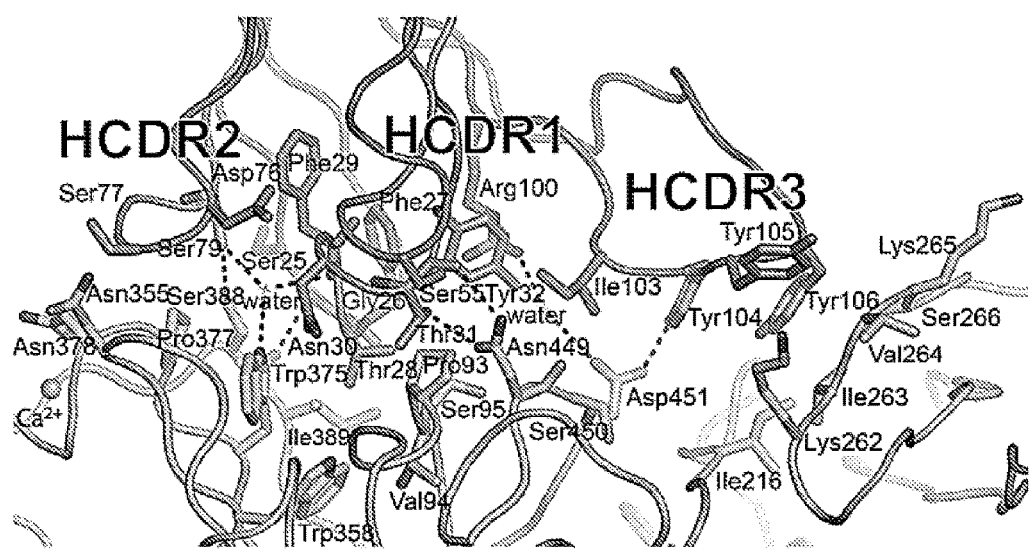
FIGS. 9A-9B. Detailed analysis of the CD6 antibody interface with the NA. (9A) The interface of H chain and CA/09 NA dimer. H$_2$O molecules that mediate interactions at the interface are highlighted as red crosses. (9B) The interface of LCDR2 and the CA/09 NA monomer. Residues key to the antibody association are highlighted in sticks and hydrogen bonds are shown as dashed lines. Interactions were analyzed using MONSTER (Salerno, W. J., Seaver, S. M., Armstrong, B. R. & Radhakrishnan, I. *Nucleic Acids Res* 32, W566-8 (2004)), PISA (Krissinel, E. & Henrick, K. *J Mol Biol* 372, 774-97 (2007)) and HBPLUS (McDonald, I. K. & Thornton, J. M. *J Mol Biol* 238, 777-93 (1994)).
Figure 9B:
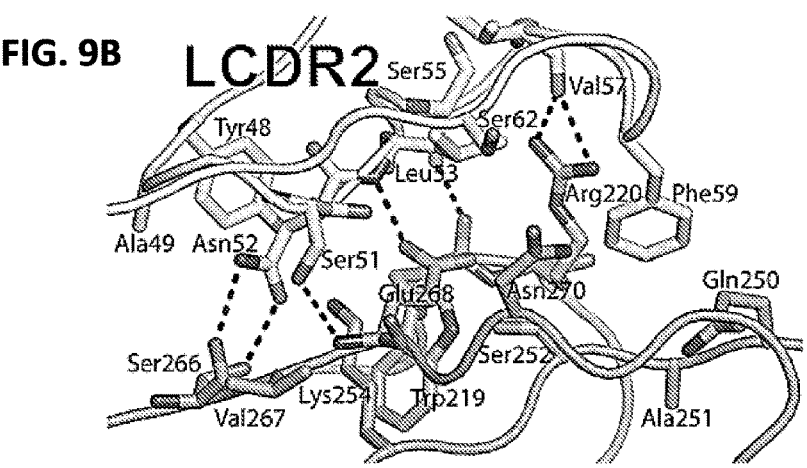

Residues Asn355, Pro377, and Asn378 of the same monomer have interactions with residues close to the HCDR2 loop, while Asn449 and Ser450 on this same monomer have hydrophobic interactions with Ile103 in the HCDR3 loop. Asp451 of the NA interacts with the HCDR3 loop, forming both a hydrogen bond with Tyr104 and an indirect interaction with Arg100 through a water molecule. Ser95, Asn449 and Asp451 are in close proximity to one another, forming a focal point of interactions with HCDR1 (including a hydrogen bond to Thr31) and HCDR3 (including a hydrogen bond to Tyr104) (FIG. 4C). HCDR3 is unique in that this loop extends between the NA monomers. Ile103, Tyr 104, Tyr105 and Tyr106 at the tip of the HCDR3 loop consequently are in positions to have hydrophobic interactions with the main chain atoms of residues in both NA monomers: Asn449, Ser450, Asp451 of one monomer and Ile216, Lys262, Ile263, Val264, Lys265 and Ser266 of the neighboring monomer (FIG. 9A). For the L chain, only the residues in and around the LCDR2 loop contribute to the antibody footprint, forming hydrophobic interactions with the second NA monomer residues Trp219, Arg220, Gln250, Ala251, Ser252, Lys254, Ser266, Val267, Glu268 and Asn270 (Table 2 and FIG. 9B).

Example 5

Identification of Amino Acids Important for CD6 Binding

Based on the above structural analyses, site-directed mutagenesis was performed to construct a panel of CA/09 NA-expressing plasmids, with mutations at positions identified as potentially important for CD6 binding based on their surface exposure, charge and the comparison of the NA sequences of BR/07, CA/09 and VN/04. The impact of each NA mutation on CD6 binding was determined by ELISA, in which 293T cells transfected with mutant expression plasmids were used as antigen. Of the single point mutations tested, those at positions at 375 and 378 (W375A, W375G and N378A) did not support expression of NA, as examined with mouse serum against CA/09 (data not shown). The impact of substitutions at another 15 NA residues was determined by comparing the relative binding of CD6 to each mutant NA and the wild-type (wt) CA/09 NA. The S95N substitution decreased the binding of CD6 (ELISA signal (OD$_{490}$) with CD6<0.4) but not CA/09-specific mouse serum (OD$_{490}$~1.2), while a conservative substitution (to Ala) at this position did not affect the binding (FIG. 5A; OD values with both CD6 and mouse serum were ~1.1, resulting in relative binding close to that of wt CA/09 NA). Although the hydroxyl group of Ser95 in NA does not interact directly with CD6, Ser95 contributes to the interaction with antibody through hydrophobic contacts with multiple residues (Thr28, Thr31 and Tyr32) of the HCDR1 loop (FIG. 9A). Structural modeling suggests that a substitution with a bulky hydrophilic side chain such as Asn could potentially disrupt binding in this region, in particular the hydrogen bonds between Asn449 of the NA with Thr31 of the HCDR1 loop. Asn is present at position 95 in the NA of VN/04, partially explaining why CD6 cannot bind to this virus. Residues at positions 220, 221, 250, 263, 264, 267, 270 and 389 of the CA/09 NA were mutated to those present in BR/07 (Table 3).

TABLE 3

Comparison of the 30 residues in the CD6 epitope to those in the NA of BR/07 and VN/04 viruses

| Virus | 93 | 94 | 95 | 216 | 217 | 219 | 220 | 221 | 250 | 251 | 252 | 254 | 262 | 263 | 264 |
|---|---|---|---|---|---|---|---|---|---|---|---|---|---|---|---|
| CA/09 | P | V | S | I | K | W | R | N | Q | A | S | K | K | I | V |
| BR/07 | S | I | . | . | . | . | K | K | A | . | . | . | . | V | T |
| VN/04 | . | I | N | . | . | . | . | . | . | . | . | . | . | V | . |

| Virus | 265 | 266 | 267 | 268 | 270 | 355 | 358 | 375 | 377 | 378 | 388 | 389 | 449 | 450 | 451 |
|---|---|---|---|---|---|---|---|---|---|---|---|---|---|---|---|
| CA/09 | K | S | V | E | N | N | W | W | P | N | S | I | N | S | D |
| BR/07 | . | . | I | . | . | . | . | . | . | . | . | V | . | . | . |
| VN/04 | . | . | . | . | D | . | . | . | . | . | . | V | . | . | . |

*a*Residues identical to those in CA/09 NA are shown as dots.

While R220K and I263V (Val263 is also present in VN/04 NA) mutations resulted in 34% and ~20% reduction in CD6 binding (FIG. 5A), respectively, no single mutation completely abolished binding. These data suggest that the lack of binding to BR/07 and VN/04 NA by CD6 is determined by multiple interactions and may reflect differences in the quaternary structure of the NA tetramers.

Figure 10:
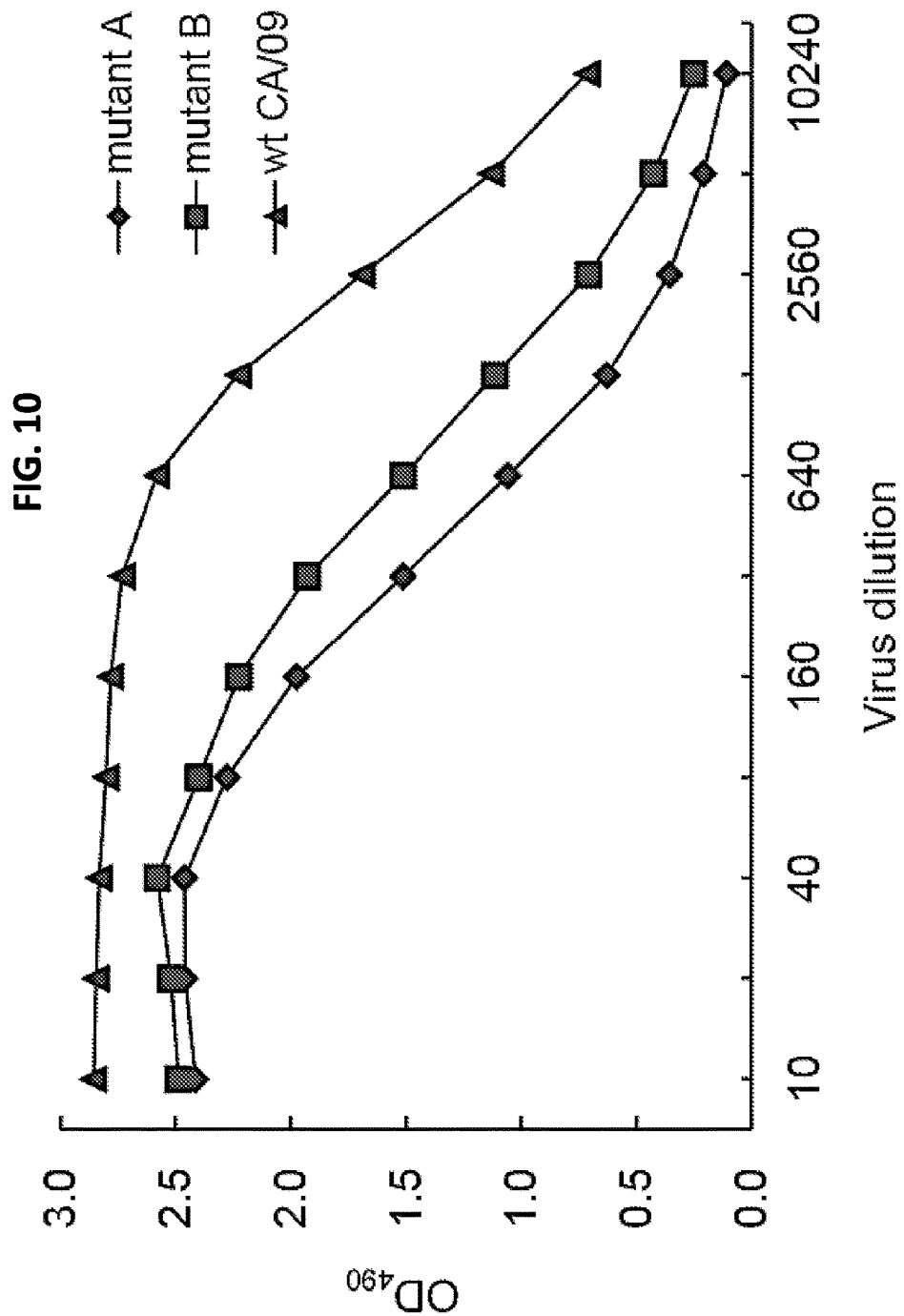
FIG. 10: The NA of escape mutants selected by mAb CD6 is less efficient than wt CA/09 NA. Enzyme activity was measured with fetuin (MW: 49 kD) as substrate in ELLA, as described in Methods. Briefly, two representative escape mutants (mutants A and B, see the legend to FIG. 5) and virus containing wt CA/09 NA, which have the same hemagglutination assay titer (1024), were serially diluted and added to 96-well plates coated with fetuin, followed by incubation overnight at 37° C.; the plates were washed and then incubated with peanut agglutinin conjugated to horse radish peroxidase to detect galactose exposed by the removal of sialic acid from fetuin by NA; the signal was developed using o-phenylenediamine dihydrochloride (OPD) as substrate. Shown are representative data from one of three independent assays.

To identify mutations in NA that would allow replication of virus in the presence of CD6, escape variants were selected in eggs inoculated with a mixture of CD6 and H6N1$_{CA/09}$ virus. Several rounds of selection were required before escape variants that resisted inhibition by CD6 in plaque assays were identified. All of the 12 variants selected had a double mutation, N449D and D451G, in the NA. As indicated by two representative variants (labeled as mutants A and B in FIG. 5B), the NA enzyme activity of these variants was still effectively inhibited by mAb HF5, but was resistant to inhibition by CD6 (FIG. 5B), suggesting that these two residues are critical for the interaction between CD6 and CA/09 NA. Indeed, in ELISA with NA expressed on 293T cells, D451G mutation reduced the relative binding of CD6 to below 10%, while the N449D/D451G double mutation abolished CD6 binding (FIG. 5A). In both the single and double mutants, the expression of NA was decreased but detectable with mouse serum (OD$_{490}$~0.65), suggesting that these changes destabilize the NA protein. The NA with N449D and D451G double mutation was less efficient than the wt NA in cleaving the substrate (FIG. 10), suggesting that its stability/activity was impaired. Interestingly, the N449D mutation alone did not have a big impact on CD6 binding. An N449K mutation, present in some recent pH1N1 isolates, did not significantly reduce CD6 binding either (FIG. 5A). These data suggest that residue 451 is a pivotal contact for CD6. Asp451 interacts directly with Tyr104 and indirectly, via a water molecule, with Arg100 on HCDR3 of CD6 (FIG. 9A). In addition, its main chain oxygen interacts with the hydroxyl of Thr215 in the neighboring NA monomer. Thus, a mutation at this residue could affect mAb binding either directly or indirectly by destabilizing the NA dimer. Selection of the double N449D and D451G mutation in escape variants suggests a potential compensatory effect of N449D to stabilize the dimer since this latter mutation does not diminish CD6 binding on its own.

Example 6

CD6 Inhibits NA Activity by Steric Hindrance

Figure 11A:
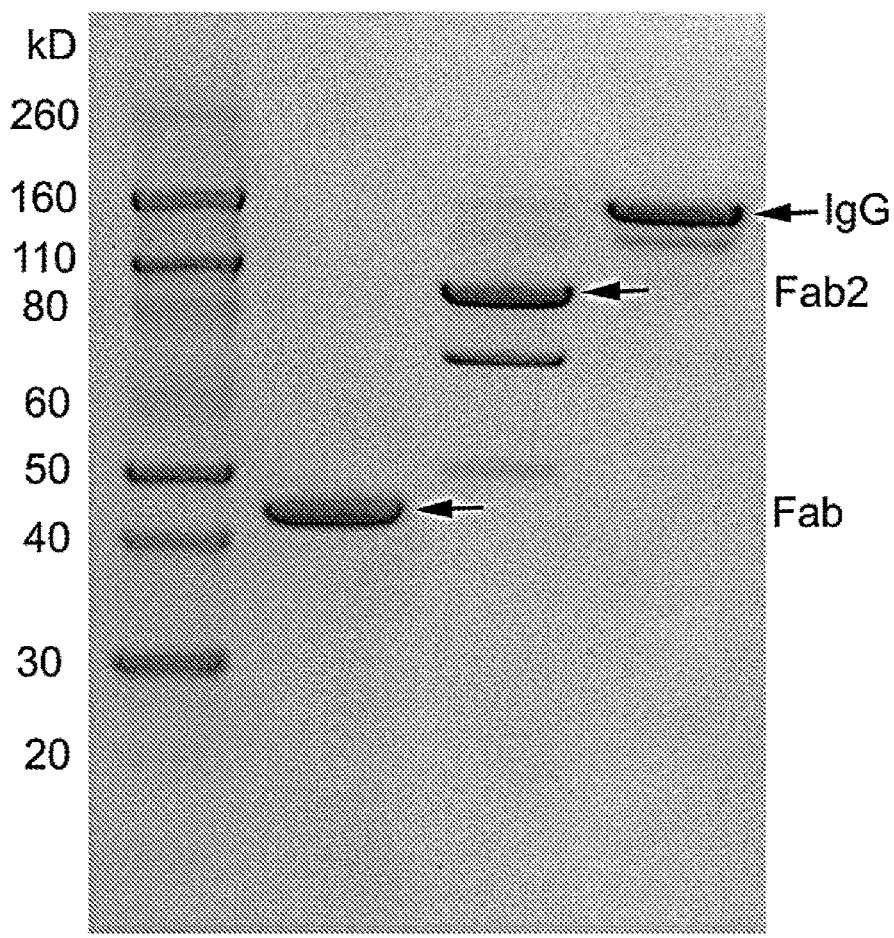
FIGS. 11A-11B. CD6 Fab and Fab2 retain ability to bind NA. (11A) SDS-PAGE of CD6 Fab (lane 2), Fab2 (lane 3) and whole IgG (lane 4). Lane 1: Novex sharp pre-stained protein standard (Invitrogen, Carlsbad, Calif., USA; catalog number: LC5800). Lanes 2-4: CD6 Fab, CD6 Fab2 and whole IgG. (11B) Binding of CD6 Fab, Fab2 and the whole IgG to CA/09 NA measured in ELISA. HRP conjugated goat-anti-mouse IgG (Fab specific) (Sigma-Aldrich, St. Louis, Mo., USA; catalog number: A2304) was used to detect the bound antibody. Shown are representative data from one of three independent assays.
Figure 11B:
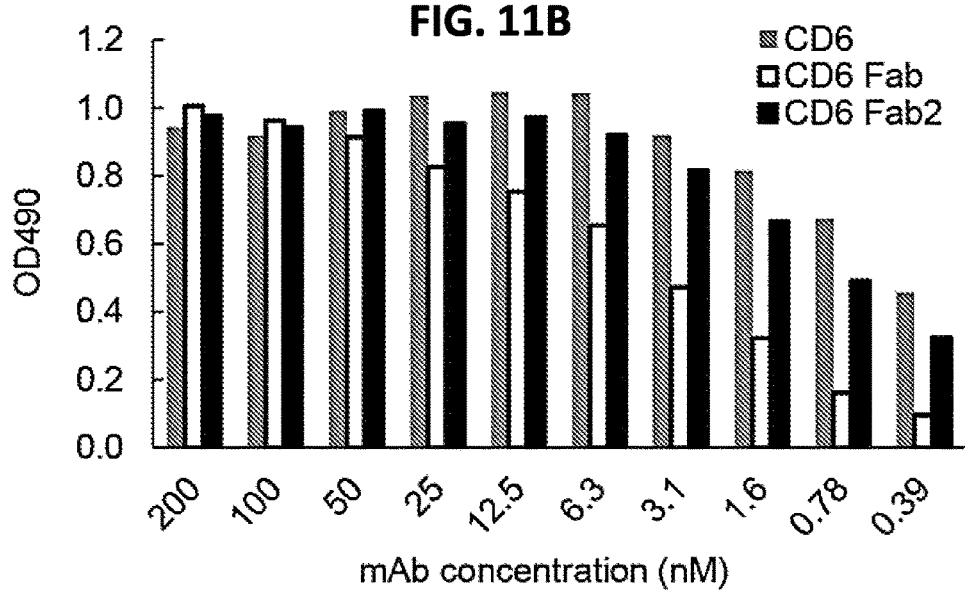

As the X-ray crystallography showed that the binding by CD6 Fab did not change the conformation of NA, it is likely that CD6-mediated inhibition of NA is through steric hindrance, i.e., CD6 blocks the access of substrate to the NA active site. This hypothesis is supported by different experimental approaches. First, the inhibition of NA activity by CD6 was affected by the size of the substrate. While CD6 inhibited the cleavage of fetuin (FIG. 1A), a large molecule with a molecular weight (MW) of 49 kD, it did not inhibit NA from cleaving a small substrate 2'-(4-methylumbelliferyl)-α-D-N-acetylneuraminic acid (MU-NANA; MW: 489 D) (FIG. 6A). This also confirms that CD6 binding does not have an allosteric effect on the enzyme active site. Unlike CD6, antibody HF5 inhibited the cleavage of both fetuin and MU-NANA by CA/09 NA (FIG. 1B and FIG. 6A). Second, the inhibition of NA activity by CD6 was impacted by the size of antibody. In assays using fetuin as substrate, the whole CD6 molecule (MW: 150 kD) inhibited NA activity most efficiently, with slightly less inhibition by the CD6 Fab2 (MW: 110 kD). However, there was little inhibition by the CD6 Fab (MW: 50 kD) even at the highest tested concentration of 40 nM (20 μg ml$^{-1}$) (FIG. 6B). This low level of inhibition was not due to the lack of binding of NA by the CD6 Fab, as ELISA results showed similar binding of NA by Fab, Fab2 and the whole IgG, especially at higher concentrations (FIG. 11). These data demonstrate that CD6 inhibits NA activity through steric hindrance rather than though structural distortion to inactivate the enzyme.

Because binding of NA antibody may also interfere with neighboring HA molecules, it was tested whether the bound CD6 molecule also hinders HA function. Pre-mixing CA/09 virus with CD6 before infecting MDCK cells did not affect the number and size of CA/09 plaques (FIG. 6C); however, when CD6 was supplemented in the agar overlay instead of being added to the virus inoculum, it inhibited the formation of CA/09 plaques (FIG. 1C and FIG. 6C). This finding shows that CD6 inhibited virus release from infected cells, rather than blocking virus attachment and entry into cells.

Example 7

Figure 12:
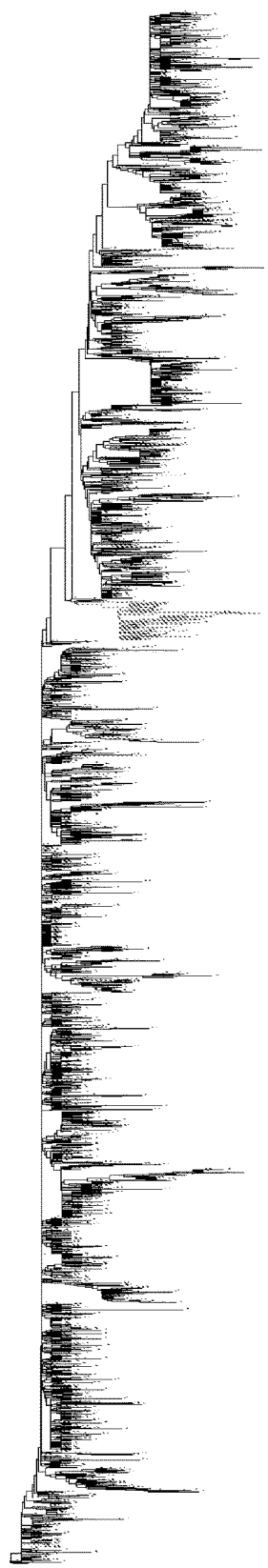
FIG. 12. Phylogenetic tree of pH1N1 NAs. The tree was constructed with n=7958 pH1N1 NA gene sequences available from the GISAID Epiflu database (on the internet, gisaid.org). Since the phylogenetic tree includes analysis of a large number of NA sequences, color annotation was used to point out the relatively few viruses carrying amino acid changes in NA that may contribute to CD6 binding; a magnification 3200-fold allows the annotation and name of each strain to be read. Amino acid changes within the CD6 epitope are annotated on the phylogenetic tree as follows: NA sequences that have changes at residue 95 are shown as diamonds; changes at residue 449 are shown as triangles; changes at residue 451 which do not have D451G in the sequence are shown as open circles; changes of D451G alone are shown as closed circles; and changes that include D451G and N386S are shown as closed squares.

Influenza Variants with Amino Acid Changes within the CD6 Epitope are Infrequent in Nature To determine whether the circulating pH1N1 viruses with changes in the CD6 epitope have emerged, all available pH1N1 NA gene sequences from GISAID (www.gisaid.org) were analyzed, excluding duplicates, those without full dates of collection or propagated in eggs. It was found that since the emergence of pH1N1 virus in 2009, very few viruses with NA mutations at amino acids 95 (n=109; 1.5%) or 449 (n=38; 0.5%) have emerged (out of 7958 available pH1N1 NA sequences). However, more viruses have been isolated with a substitution at Asp451 (n=196; 2.5%). The D451G mutation that reduces CD6 binding arose sporadically among several different NA lineages since 2009 (FIG. 12), and was for a time fixed in the clade 6A subset of pH1N1 viruses. A Bayesian molecular clock analysis was performed to estimate the date of origin for the D451G mutation in the NA gene from clade 6 and showed that it arose in early 2010 (2010.026, Bayesian confidence interval, 2008.824-2010.929) along with an additional mutation N386S, within NA genetic clade 6A. Although Asn386 is a predicted glycosylation site, occupancy of this site was not apparent in the final structure. However, the B-factors for this residue are higher than its neighboring residues, suggesting that this site may indeed be glycosylated. The D451G mutation was noticeable in the NA of viruses sequenced in 2012 (Table 4) but was present in a much smaller proportion of sequences in 2013 (~3% of available pH1N1 NA sequences).

Consistent with the greatly reduced CD6 binding to the D451G mutant NA of CA/09 observed in cell-based ELISA (FIG. 5A), this mutation alone resulted in significant loss of CD6's ability to inhibit enzyme activity (FIG. 7A). Since this mutation is present in clade 6A NA of some viruses isolated in 2012 (FIG. 12), it was tested whether this clade of NA had become resistant to inhibition by CD6. Surprisingly, it observed that the NA of A/Bangladesh/2021/2012 (BA/12), a reference pH1N1 virus that has a clade 6A NA, retained sensitivity to CD6 inhibition (FIG. 7A). Besides the D451G mutation, BA/12 NA has additional changes, including V106I, V241I, N248D, N369K and N386S. It is not known how these additional changes help to retain the sensitivity of BA/12 NA to CD6 inhibition. Unlike CD6, the control mAb HF5 did not inhibit the NA of CA/09 when it was engineered to contain an N369K mutation, suggesting that HF5 recognizes an epitope with amino acid 369 as one of the key contacts. This mutation is contained in the NA of BA/12 and therefore, as expected, BA/12 NA was not susceptible to HF5 inhibition (FIG. 7B). It is encouraging that CD6 remains effective against mutant H1N1 viruses with variations in the CD6 epitope and the epitopes recognized by other antibodies (e.g., the HF5 epitope); continued monitoring on the sensitivity of pH1N1 viruses to CD6 will help to determine whether CD6-resistant variants can arise.

While variants with amino acid changes within the CD6 epitope are infrequent, some pH1N1 strains have developed resistance to current antiviral drugs, including NA inhibitors (Storms, A. D. et al. *Emerg Infect Dis* 18, 308-11 (2012); Memoli, M. J. et al. *Clin Infect Dis* 50, 1252-5 (2010)). The

TABLE 4

Variation of CD6 epitope residues in pH1N1 viruses

Mutation rate by year % (number of pH1N1 isolates with mutation)[a]

| Residue | 2009 | 2010 | 2011 | 2012 | 2013 | Total |
|---|---|---|---|---|---|---|
| Pro93 | 0.05 (2) | 0.5 (6) | 0.84 (9) | 0.16 (1) | 1.22 (10) | 0.35 (28) |
| Val94 | 0.02 (1) | 0.08 (1) | 0.09 (1) | 0.33 (2) | 0.24 (2) | 0.09 (7) |
| Ser95[b] | 2.13 (91) | 0.67 (8) | 0.28 (3) | 0.66 (4) | 0.37 (3) | 1.37 (109) |
| Ile216 | 0.16 (7) | | | 0.33 (2) | 0.24 (2) | 0.14 (11) |
| Lys217 | 0.07 (3) | 0.17 (2) | | 0.82 (5) | 0.12 (1) | 0.14 (11) |
| Trp219 | | | 0.09 (1) | | | 0.01 (1) |
| Arg220 | 0.23 (10) | 0.67 (8) | 1.49 (16) | 1.48 (9) | 8.19 (67) | 1.39 (111) |
| Asn221 | 0.07 (3) | 0.25 (3) | | 0.66 (4) | 0.24 (2) | 0.15 (12) |
| Gln250 | | 0.08 (1) | | | | 0.01 (1) |
| Ala251 | 0.02 (1) | | | | | 0.01 (1) |
| Ser252 | | | | | | |
| Lys254 | | 0.08 (1) | | | | 0.01 (1) |
| Lys262 | 0.09 (4) | 0.08 (1) | 0.28 (3) | | 0.12 (1) | 0.11 (9) |
| Ile263 | 0.28 (12) | 0.76 (9) | 0.19 (2) | 0.33 (2) | 0.12 (1) | 0.33 (26) |
| Val264 | 0.23 (10) | 2.27 (27) | 2.52 (27) | 0.99 (6) | 1.34 (11) | 1.03 (82) |
| Lys265 | 0.02 (1) | 0.08 (1) | 0.09 (1) | | 0.24 (2) | 0.06 (5) |
| Ser266 | | | | | 0.12 (1) | 0.01 (1) |
| Val267 | 0.07 (3) | 0.08 (1) | 0.28 (3) | 0.66 (4) | | 0.14 (11) |
| Glu268 | 0.02 (1) | 0.08 (1) | | | | 0.03 (2) |
| Asn270 | 0.16 (7) | 0.25 (3) | 0.37 (4) | 0.33 (2) | 0.49 (4) | 0.25 (20) |
| Asn355 | 0.07 (3) | | 0.28 (3) | 0.16 (1) | 0.12 (1) | 0.10 (8) |
| Trp358 | | 0.08 (1) | | | 0.12 (1) | 0.03 (3) |
| Trp375 | | | | | | |
| Pro377 | | 0.08 (1) | 0.09 (1) | | 0.12 (1) | 0.04 (3) |
| Asn378 | | | | 0.37 (4) | 0.12 (1) | 0.06 (5) |
| Ser388 | 0.26 (11) | 0.34 (4) | 0.09 (1) | | | 0.20 (16) |
| Ile389 | 0.23 (10) | 1.17 (14) | 4.19 (45) | 3.79 (23) | 3.18 (26) | 1.48 (118) |
| Asn449 | 0.14 (6) | 0.25 (3) | 0.19 (2) | 1.15 (7) | 2.44 (20) | 0.48 (38) |
| Ser450 | 0.07 (3) | 0.25 (3) | 0.28 (3) | 0.16 (1) | 2.44 (20) | 0.15 (12) |
| Asp451 | 0.26 (11) | 1.34 (16) | 2.61 (28) | 18.78 (114) | 3.18 (26) | 2.46 (196) |
| Total | 4268 | 1192 | 1073 | 607 | 818 | 7958 |

[a]Data were generated with 7958 pH1N1 NA sequences available from GISAID (www.gisaid.org).
[b]Residues in bold represent those identified to be critical for the binding of NA by mAb CD6.

Figure 13:
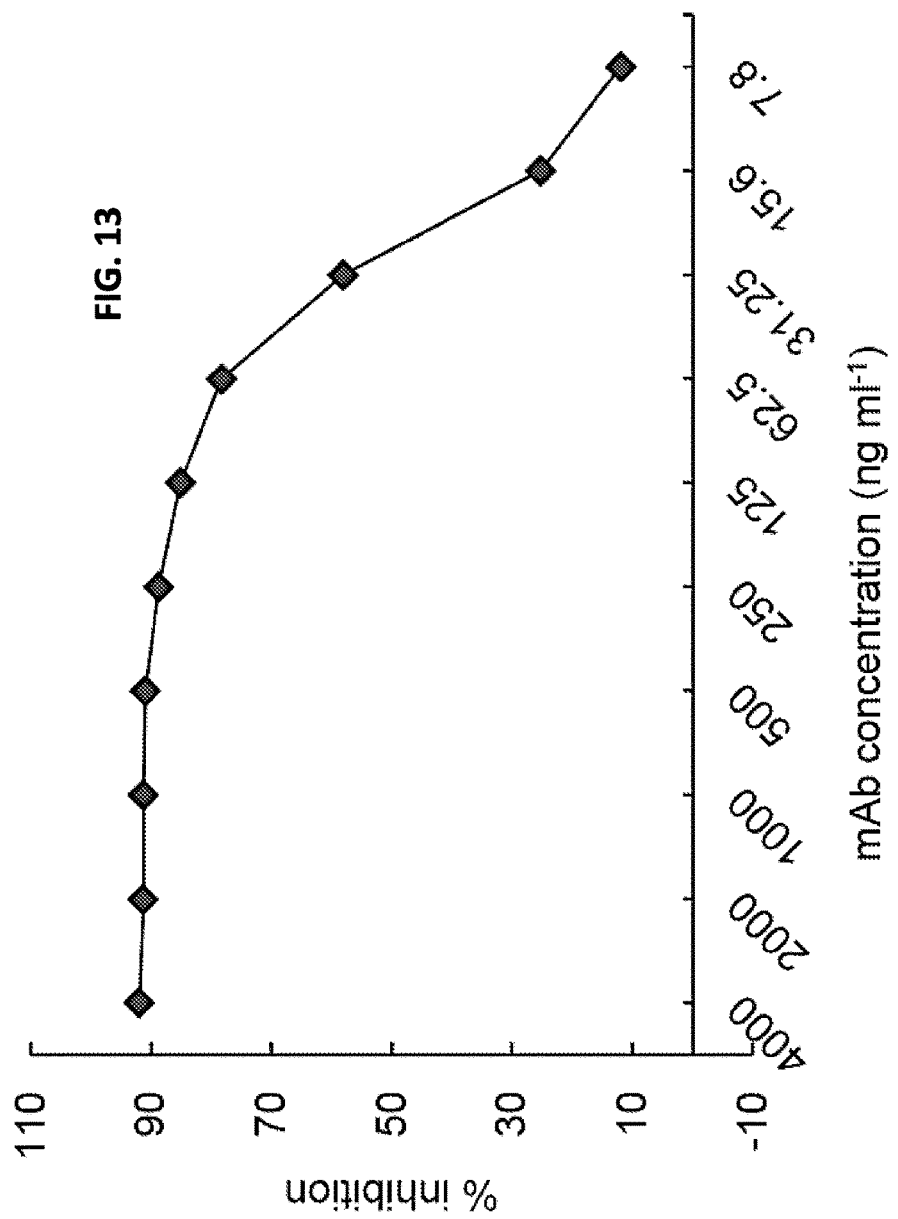
FIG. 13. Inhibition of the NA activity of A/Bethesda/NIH107-D31/2009 virus by antibody CD6. The pH1N1 virus has an H275Y mutation in the NA, and therefore is resistant to NA inhibitors oseltamivir and peramivir. The inhibition was measured with ELLA, in which fetuin (MW: 49 kD) was used as substrate. Serial dilutions of antibody CD6 were added to wells prior to the addition of virus. Shown are representative data from one of three independent assays.

The change in proportion of pH1N1 viruses with the D451G mutation corresponds with the decreased circulation of pH1N1 viruses from genetic group 6A since 2012. Approximately 95% of the viruses that circulated in 2013 contained NA of genetic clade 6B, which retains the CD6 epitope. To date, none of the NA sequences available in GISAID contain the N449D/D451G double mutation.

ability of antibody CD6 to inhibit the NA activity of A/Bethesda/NIH107-D31/2009, a pH1N1 virus which is resistant to both oseltamivir and peramivir due to a H275Y mutation in the NA (Memoli, M. J. et al. *J Infect Dis* 203, 348-57 (2011); Memoli et al., 2010, supra) was tested. CD6 inhibited the drug-resistant virus at very low concentrations ($IC_{50}$: 29 ng ml$^{-1}$) (FIG. 13), highlighting the potential of the CD6 epitope to serve as a target for alternative antibody therapeutics against pH1N1 virus infection.

The results presented herein show that CD6, a NA-specific mAb, protects mice against lethal challenge with the reassortant pH1N1 virus CA/09-X179A, making it an antibody candidate for treating infection with pH1N1 viruses, especially those resistant to licensed NA inhibitors. The CD6 epitope was elucidated by x-ray crystallography and the interactions that are most important for activity were investigated. The data show that the CD6 epitope is unique, spanning neighboring NA monomers, with 30 amino acids serving as antibody contacts.

The results presented herein provide the first structural report for a N1 NA/mAb complex. In addition, unlike the N2 (Gulati, U. et al., *J Virol* 76, 12274-80 (2002)) and N9 (Tulip, W. R. et al., *J Mol Biol* 227, 122-48 (1992); Malby, R. L. et al., *Structure* 2, 733-46 (1994); Colman, P. M. et al., *Nature* 326, 358-63 (1987); Lee, J. T. et al., *Virology* 300, 255-68 (2002))/Fab crystal structures that define epitopes on the upper face of individual NA monomers, the CD6 epitope differs by spanning the lateral face of neighboring N1 monomers. Although an epitope present in intact dimers was also proposed for the N8 subtype-specific mAb (N8-4) based on analysis of mAb escape mutants (Sato, T et al., *J Virol* 68, 1790-6 (1994)), the epitope was never structurally defined. Epitopes that span the monomers of NA and HA may be overlooked due to the use of screening assays that do not retain the quaternary protein structure. For HA, most of the mAbs reported, including those targeting conserved antigenic sites, bind to single HA1/HA2 monomers. Nevertheless, mAbs that bind simultaneously to two HA monomers have occasionally been described (Barbey-Martin, C. et al. *Virology* 294, 70-4 (2002); Iba, Y. et al., *J Virol* 88:13 7130-7144 (2014), suggesting that the molecular structure of HA allows antibodies to be generated that bind across the monomer-monomer interface of the trimer.

The mAbs that span HA monomers are efficient in neutralizing virus in vitro (Barbey-Martin C. et al., 2002, supra; Iba, Y. et al., 2014, supra) and thus are likely to be protective in vivo. The in vivo studies disclosed herein showed that NA-specific mAb CD6 protected mice against severe disease. When given prophylactically, a low dose of 0.5 mg kg$^{-1}$ protected all mice against lethal CA/09-X179A virus challenge. In the therapeutic study, a single dose of 5 mg kg$^{-1}$ or multiple doses of a lower dose (2.5 or 1 mg kg$^{-1}$) protected mice from lethal virus challenge. These findings evidence that the interface of either HA or NA monomers is a target for the development of therapeutic antibodies against influenza.

The atomic structure of CA/09 NA in complex with CD6 Fab identified 30 amino acids that have contact with antibody. This number of contacts is far greater than those observed for other NA/Fab complexes—mAbs NC10 and NC41 have 14 and 17 amino acid contacts in N9 (Malby, R. L. et al., 1994, supra), respectively, while mAb Mem5 contacts 17 amino acids in N2 (Venkatramani, L. et al. *J Mol Biol* 356, 651-63 (2006)). With a larger number of contacts between NA and mAb, it might be less likely for single mutations in NA to eliminate mAb binding, even though the antibody avidity may change to some degree. In the case of CD6, it required multiple rounds to select escape mutant viruses. These escape variants bear double mutations N449D/D451G in NA, rather than single amino acid mutation as often observed in mutant selection with other NA mAbs (Wan, H. et al. *J Virol* 87, 9290-300 (2013); Air, G. M. et al. *Virology* 145, 237-48 (1985); Webster, R. G. et al. *J Virol* 61, 2910-6 (1987)). Interestingly, residues 449 and 451, together with residue 95, are present as a cluster and therefore possibly form an important anchor for CD6 binding.

The epitope targeted by CD6 remains largely conserved, although mutations at some of the residues in CD6 epitope have occurred at a low rate. None of the pH1N1 NA sequences available in GISAID contain both N449D and D451G, the mutations identified in CD6 escape variants. A small proportion of pH1N1 viruses contain the D451G single substitution in NA. This single change in the NA of CA/09 reduced CD6 binding, however additional mutations in the NA might have helped some of these variant viruses to retain sensitivity to CD6, as demonstrated by our analysis with a representative virus BA/12.

The findings that CD6 inhibited NA cleavage of large molecule fetuin but not the small substrate MU-NANA suggested that this antibody inhibited NA activity by blocking access of substrate to the enzyme active site. This concept is in agreement with the structural observations; there was no distortion of the NA structure in complex with CD6, and although the boundary of the CD6 epitope, formed by the HCDR2 loop, is distant from the NA active site, amino acid contacts for the L chain on the neighboring monomer are in close proximity to the active site. Thus, CD6 is likely to block the active site of the monomer to which the L chain binds, with four CD6 molecules needed to inhibit all NA active sites of a tetramer.

Another observation that supports a mechanism of steric hindrance is that the size of the CD6 molecule impacts inhibition. In the in vitro assays, CD6 Fab2 inhibited CA/09 NA to a greater degree than CD6 Fab, and the best inhibition was observed with whole CD6 IgG. In the case of the interaction between NA and the whole CD6 molecule, the other Fab arm as well as the Fc region of the antibody may contribute to blocking access of substrate to NA, either by obstructing the active site by its bulk, or by cross-linking adjacent NA tetramers. While this may be important therapeutically, the antigen binding fragments can still be used in diagnostic assays.

Disclosed herein is the structure of NA subtype N1 in complex with a highly protective mAb that binds an epitope that spans adjacent NA monomers. Without being bound by theory, the large number of interactions between NA and CD6 are likely to stabilize the complex. The apparent need for two amino acid changes in CD6 epitope to enable antibody escape consequently reduces the likelihood of generating CD6-resistant variants. The absence of NA sequences with changes at both 449 and 451 residues give confidence that CD6-resistant viruses are not currently in circulation. These observations show that mAb CD6 is suitable as a prophylactic or therapeutic treatment against H1N1 influenza, and is of particular value in face of emerging NA-inhibitor resistant variants. Vaccines and therapeutic antibodies can be developed that target similar epitopes in NAs of other influenza types and subtypes, including those with pandemic potential.

Example 8

Additional Material and Methods for Examples 9-13

Viruses and Antibodies.

The wt pH1N1 virus A/California/07/2009 (CA/09) and vaccine candidate virus CA/09-179A were propagated in 9-11 days old embryonated chicken eggs and titrated in eggs or Madin-Darby canine kidney (MDCK) cells. $H6N1_{BR/07}$ and $H6N1_{CA/09}$ reassortant viruses, which contain the hemagglutinin (HA) gene of H6N2 virus A/turkey/Massachusetts/3740/1965 and the NA gene of CA/09 or a seasonal H1N1 A/Brisbane/59/2007 (BR/07), were rescued using reverse genetics (Sandbulte et al., Proc Natl Acad Sci USA 108:20748-20753, 2011) and grown in 9-11 days old embryonated chicken eggs for determining the inhibitory effect of antibodies. Viruses used for ELISA were inactivated with β-propiolactone (Sigma-Aldrich, St. Louis, Mo.) and purified by sucrose gradient centrifugation. Virus counting was performed as reported (Plant and Ye, J Gen Virol 96:752-755, 2015) using Virus Counter 2100 (ViroCyt, Boulder, Colo.). Hybridomas that secrete MAbs were generated as previously described (Wan et al., J Virol 87:9290-9300, 2013; Wan et al., Nat Commun 6:6114, 2015) and cultured in CELLINE™ Device (BD Biosciences, San Jose, Calif.). MAbs were purified using protein G columns (GE Healthcare, Uppsala, Sweden) according to the instructions provided by the manufacturer.

Site-Directed Mutagenesis.

Nucleotide changes corresponding to single mutations (S339A, S364N, N369K, N397K and N449D) were introduced into the CA/09 NA gene in pCAGGS-CA/09 NA plasmid (Easterbrook et al., Virology 432:39-44, 2012) with QUICKCHANGE® multi site-directed mutagenesis kit (Stratagene, La Jolla, Calif.). The resulting plasmids were sequenced to verify the presence of introduced mutations and the absence of additional, unwanted mutations.

Cell-Based ELISA.

The assay was performed as previously described (Wan et al., J Virol 87:9290-9300, 2013). NA was expressed on 293T cells by transfecting with wt or mutant plasmids using LIPOFECTAMINE™ 2000 (Invitrogen Inc., Grand Island, N.Y.). Briefly, 293T cells at approximately 90% confluence in 96-well plates were incubated with a mixture of plasmid (0.2 μg/well) and LIPOFECTAMINE™ 2000 (0.5 μl/well) in Opti-MEM I medium (50 μl/well) (Invitrogen, Grand Island, N.Y.) for 6 h. The mixture was removed and fresh medium added. Forty-eight hours after the addition of transfection mixture, the cells were fixed with 0.05% glutaraldehyde for 15 min at room temperature. The cells were washed and then blocked with 3% BSA in PBS for 1 h at 37° C. Cells were then incubated with MAbs (1 μg/ml), followed by incubation with peroxidase-conjugated goat-anti-mouse IgG (Sigma-Aldrich, St. Louis, Mo.). Both incubations were for 1 h at 37° C. The signal was developed using o-phenylenediamine dihydrochloride (OPD) as substrate. The reaction was stopped with 1N $H_2SO_4$ and $OD_{490}$ values were read. Expression of NA was confirmed with hyperimmune mouse serum against CA/09 (with hemagglutination inhibition (HI) titer ≥320). The signals generated by MAb binding to mutant NAs were normalized to that generated by hyperimmune mouse serum and therefore expressed as relative binding. A >20% decrease in relative binding compared to wt NA was arbitrarily considered significant for the purpose of epitope identification.

Conventional ELISA.

Native and denatured preparations of purified CA/09-X179A virus were coated onto ELISA plates (10 μg/ml, 100 μl/well). The purified virus was denatured by suspension in 1% sodium dodecyl sulfate (SDS) and 50 mM dithiothreitol (DTT) followed by heating at 95° C. for 5 min before dilution in coating buffer. The virus-coated plates were blocked and then incubated with HF5 (1 μg/ml for native virus and 2 μg/ml for denatured virus) and controls. Mouse serum against CA/09 virus (with HI titer ≥320) and rabbit MAb clone 001 (Sino Biological, Beijing, China) that binds to CA/09 NA under both reducing and non-reducing conditions were used as positive controls, while MAb 3A2 that is specific to the NA of BR/07-like H1N1 virus was included as negative control. After an additional incubation with peroxidase-conjugated goat-anti-mouse IgG or peroxidase-conjugated goat-anti-rabbit IgG (Sigma-Aldrich, St. Louis, Mo.), the signal was developed using OPD as substrate. The reaction was stopped with 1N $H_2SO_4$ and $OD_{490}$ values were read.

Plaque Assay.

MDCK cells growing in 6-well- or 12-well plates were infected with 20-30 plaque forming units (pfu) of virus for 1 h at 37° C. After the removal of viral inoculum, cells were washed with PBS and overlaid with agar supplemented with MAbs and 1 μg/ml of trypsin. Cells were incubated at 37° C., 5% $CO_2$ for 3 days, followed by fixing with methanol and staining with crystal violet solution to visualize plaques. Infected cells that did not contain antibody in the agar overlay were set up as control. To measure the sizes (diameters) of plaques, plaque images were magnified in Photoshop (CS6 extended), 20 plaques were randomly selected for each antibody concentration, the diameters were determined using measurement tool within the software, converted to real sizes (mm) and compared to those of the control plaques.

Virus Growth Kinetics.

MDCK cells in 12-well plates were inoculated with CA/09 virus at a multiplicity of infection (MOI) of 0.001 for 1 h (run in duplicate wells). The inoculum was removed by extensive washing with PBS, and cells were maintained in Opti-MEM I medium (Invitrogen, Grand Island, N.Y.) supplemented with 1 μg/ml of trypsin and various concentrations of each MAb. Supernatants were sampled at time points 0, 8, 10, 24, 36 and 48 h post infection (p.i.). Virus in the supernatant was titrated with plaque assay.

Enzyme-Linked Lectin Assay (ELLA).

The inhibition in NA activity was measured with ELLA as described previously (Couzens et al, J Virol Methods 210C: 7-14, 2014). Briefly, serial dilutions of mouse sera or MAbs were mixed with a predetermined amount of virus diluted in PBS containing 1% BSA and 0.05% Tween 20 (PBST). The mixture was transferred to 96-well plates coated with fetuin (Sigma-Aldrich, St. Louis, Mo.) and incubated at 37° C. overnight. Plates were washed with PBST, followed by the addition of peanut agglutinin conjugated to peroxidase (Sigma-Aldrich, St. Louis, Mo.). Plates were incubated at room temperature for 2 h in the dark and washed with PBST before the addition of OPD substrate. The reaction was stopped by adding 1N $H_2SO_4$ and $OD_{490}$ values were read. The NA inhibition (NI) titer was expressed as the reciprocal of the highest dilution that exhibited ≥50% inhibition of NA activity or the 50% inhibition concentration ($IC_{50}$) that was determined by non-linear regression analysis (GraphPad Prism 5).

Absorption of Passively Administered MAbs.

Female DBA/2 mice (8 weeks old, The Jackson Laboratory) were used in animal studies. Antibody or PBS was administered intraperitoneally (i.p.) to groups of mice (n=3) at a dose of 5 mg/kg of weight. Mouse sera were collected 1, 3, 6, 9 and 14 days after antibody or PBS injection and stored at −80° C. until NI titers were measured by ELLA.

Prophylactic and Therapeutic Studies.

Female DBA/2 mice (8 weeks old, The Jackson Laboratory) were used in prophylactic and therapeutic studies. To determine the impact of MAbs administered before infection (prophylactic efficacy), groups of mice (n=14 or 20) were treated with antibodies HF5 and CD6 at doses of 0.2, 1 and 5 mg/kg, or with antibodies 4E9 and 1H5 at doses of 5, 10 and 15 mg/kg, or with the control antibody 3A2 at 5 or 15 mg/kg. Each dose was administered i.p. in a volume of 200 μl. Twelve hours later, mice were challenged intranasally (i.n.) with 10 $MLD_{50}$ of CA/09. On days 6 and 8 post challenge (p.c.), 3 mice from each group were euthanized, and the lungs collected for viral titration in MDCK cells. In the study to evaluate the therapeutic benefit of MAbs HF5, CD6 and 1H5, groups of mice (n=14 or 20) were infected i.n. with 10 $MLD_{50}$ of CA/09 before MAb treatments: each MAb was delivered i.p. once (on day 1 p.c.), twice (on days 1 and 5 p.c.), or three times (on days 1, 2 and 3 p.c.). HF5 and CD6 were each administered at 5 mg/kg; 1H5 was administered at 10 mg/kg, while the control antibody 3A2 was administered at either 5 or 10 mg/kg. On days 6 and 8 p.c., 3 mice from each group were euthanized for titration of lung viral titers. For antibodies HF5 and CD6 administered prophylactically (5 mg/kg) or therapeutically (3 doses of 5 mg/kg), an additional 6 mice were included in order to determine viral titers in lungs collected on days 10 and 12 p.c. In all groups, the remaining mice (8 per group) were weighed on day 0 or day 1 before virus challenge and monitored daily for 14 days for weight loss and survival. Mice that lost ≥25% of weight were euthanized.

Identification of CA/09 Escape Mutants in MAb-Treated Mice.

Lung samples from mice in the prophylactic and therapeutic studies were examined for the presence of escape variants in plaque assays by supplementing the agar overlay with the selecting MAb (2 μg/ml). Plaques that were larger than the control (wt CA/09 in the presence of each antibody) were picked and expanded in 9-11 days old embryonated chicken eggs. Allantoic fluid was collected for the sequencing of NA gene.

RT-PCR and Gene Sequencing.

Viral RNA was extracted from allantoic fluid with RNeasy® Mini Kit (Qiagen Corporate, Valencia, Calif.). cDNA synthesis and PCR were performed as previously described (34) to amplify the NA gene. PCR products were sequenced at the Core Facility, CBER, FDA.

Enzyme Activity.

NA activities of MAb escape mutants and wt CA/09 were compared in ELLA and MU-NANA assay. The latter assay was performed using 4-methylumbelliferyl-N-acetyl-α-D-neuraminic acid (MU-NANA, Sigma, St Louis, Mo.) as substrate. Serial dilutions of virus were mixed with an equal volume (50 μl) of 100 μM MU-NANA in PBS (pH 7.4) and incubated at 37° C. for 1 h. The reaction was stopped by the addition of 0.1 M glycine (pH 10.7)-25% ethanol and fluorescence was read (excitation 355 nm, emission 460 nm).

Statistical Analysis.

Data were analyzed with one way analysis of variance (ANOVA, GraphPad Prism 5) using Dunnett's multiple comparison test. P values <0.05 were considered statistically significant.

Example 9

MAbs Used in the Study Recognize Different Epitopes of the pH1N1 Virus NA

Four N1-specific MAbs were used. Two of the MAbs, HF5 and CD6, bind to the NA of CA/09. NA residues 95, 449 and 451 are important for binding of CD6. Antibodies 4E9 and 1H5 are broadly-reactive with the NA of H1N1 (including seasonal and pandemic H1N1) and H5N1 viruses, with NA residues 273, 338 and 339 being the important contacts (Wan et al., J Virol 87:9290-9300, 2013; Wan et al., Nat Commun 6:6114, 2015).

Figure 14A:
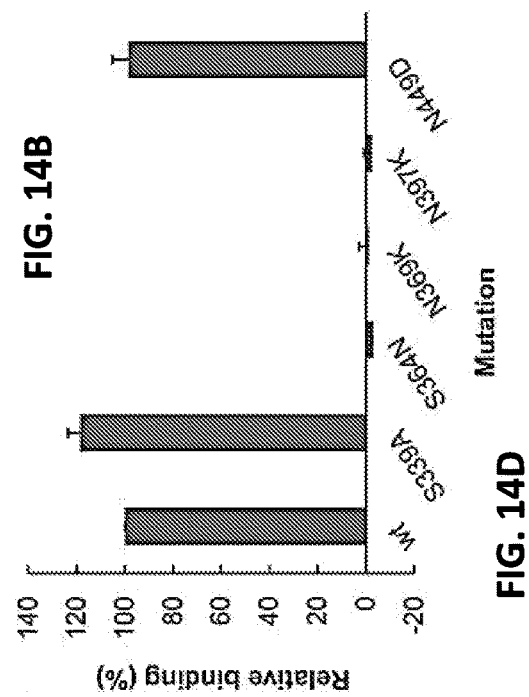
FIGS. 14A-14 D. MAbs HF5, CD6, 4E9 and 1H5 bind different epitopes in the NA of pH1N1 virus. (14A) MAb HF5 binds to native but not denatured CA/09-X179A. Data from ELISA show binding of HF5 to purified whole virus (solid bars) but not CA/09-X179A that has been dissociated and heat denatured (hatched bars). Assay controls are labeled as: serum (mouse serum against CA/09 virus), 001 (rabbit MAb against CA/09 NA), 3A2 (MAb specific to the NA of BR/07-like H1N1 virus). Shown are mean OD values of two independent assays run in duplicate wells; standard deviation (SD) is shown with an error bar. (14B) Binding of MAb HF5 to a panel of mutant CA/09 NAs expressed on 293T cells. The binding was measured by cell-based ELISA, with signals normalized to those obtained with mouse serum against CA/09 and is therefore expressed as relative binding. Shown are mean+SD of two independent assays run in duplicate wells. (14C) A model that depicts the residues in an NA dimer (Protein Data Bank code 3NSS) that are important for the binding of MAbs HF5, CD6 as well as 4E9 and 1H5 (highlighted in black). The image was generated with Pymol software (Delano Scientific). (14D) The same model as in (14C) shown from a different view.
Figure 14B:
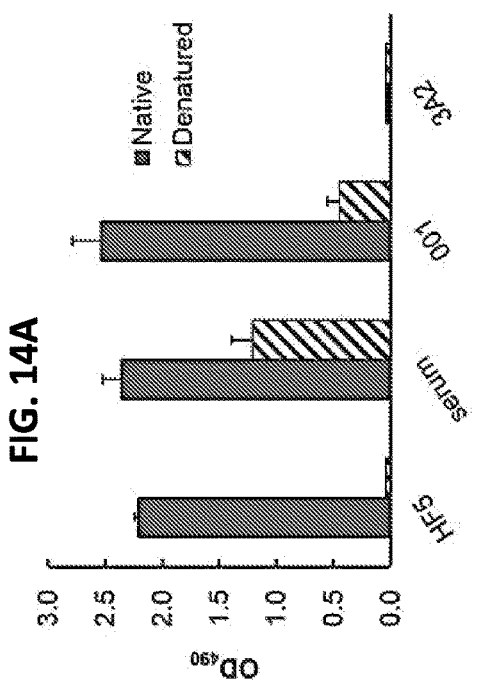
Figure 14C:
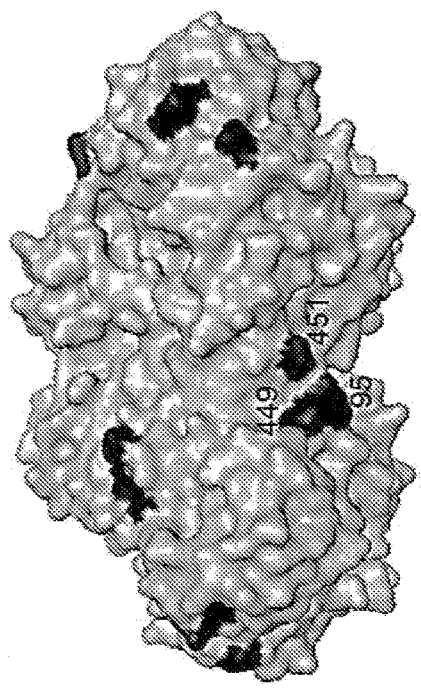
Figure 14D:
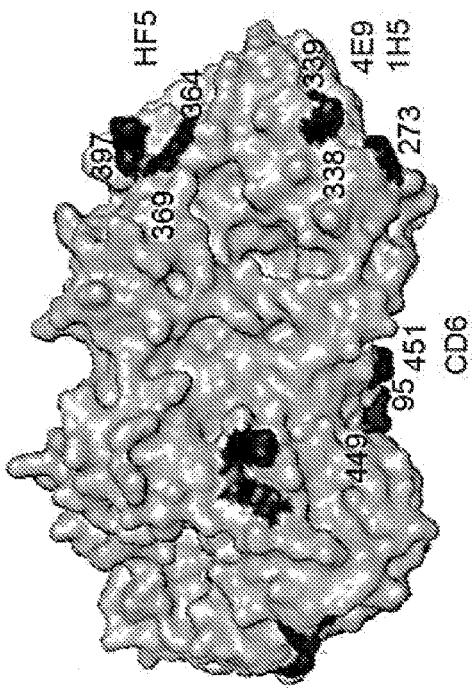

The epitope recognized by HF5 is not fully elucidated. In ELISA using CA/09-X179A virus-coated plates, HF5 bound to native virus, but not denatured virus, indicating that HF5 epitope is dependent on the native conformation (FIG. 14A). NI assays suggested that HF5 may bind to an epitope involving residue 369 (see above). The binding of HF5 to various mutant CA/09 NAs transiently expressed on 293T cells was examined. Cell-based ELISA with these mutant NAs clearly demonstrated that an N to K mutation at residue 369 abolished the binding of NA by HF5 (FIG. 1B). This finding confirms that residue 369 is a key contact in the HF5 epitope. In addition, S364N and N397K mutations in NA resulted in complete loss of HF5 binding in cell-based ELISA. Residues 364, 369 and 397 are in close proximity to one another and are clearly important contacts for HF5. The HF5 epitope is therefore distinct from the CD6 epitope as well as the epitope recognized by antibodies 4E9 and 1H5. Thus, the antigenic domains recognized by these four MAbs represent three different epitopes in N1 of pH1N1 virus (FIGS. 14C and D).

Example 10

HF5 and CD6 Inhibit NA Activity and Virus Growth More Efficiently than MAbs 4E9 and 1H5

Figure 15A:
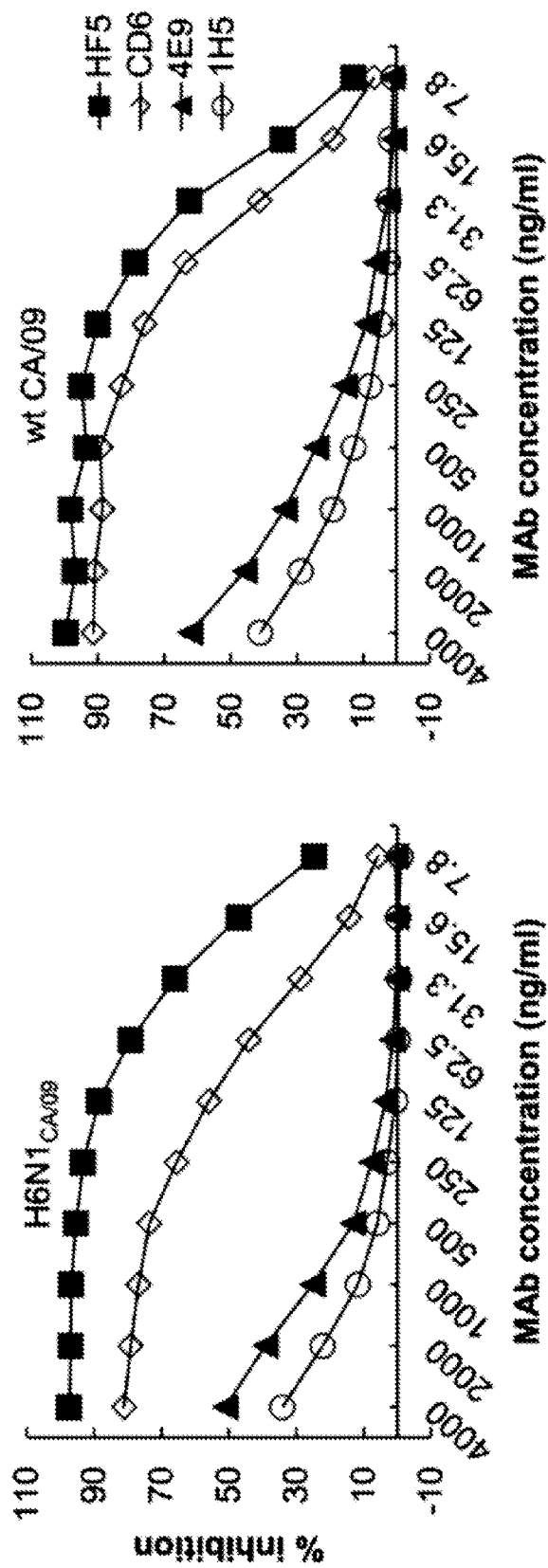
Figure 15C:
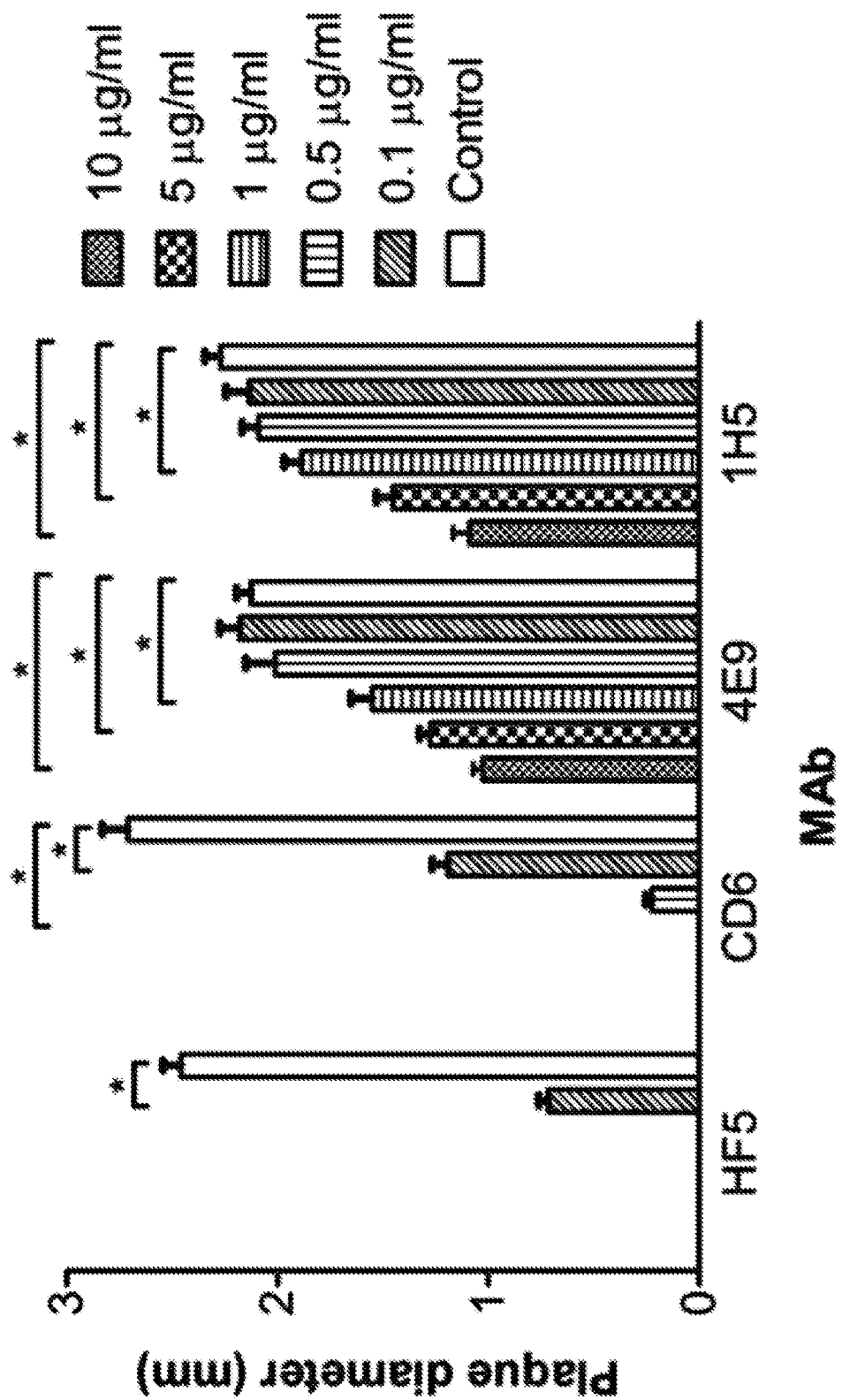

Studies using $H6N1_{CA/09}$ virus in ELLA demonstrated that HF5 and CD6 are more effective in inhibiting the NA activity of pH1N1 virus than 4E9 and 1H5 (see above). This difference in inhibitory efficacy was also observed with wt CA/09 in ELLA: the median inhibition concentration ($IC_{50}$) of CD6 and HF5 was <100 ng/ml, while that of 4E9 and 1H5 was >2 μg/ml (FIG. 15A). The effect of the four MAbs on the growth of wt CA/09 in MDCK cells was compared. Antibody 3A2, which is reactive only to BR/07-like H1N1 viruses, was included as a negative control. In plaque assay, both HF5 and CD6 inhibited CA/09 plaque formation or resulted in smaller plaques when the agar overlay was supplemented with either MAb. Only pinpoint plaques were formed at MAb concentrations ≥1 μg/ml. When applied at 0.5 μg/ml, HF5 still efficiently inhibited CA/09 plaque formation, while clear, small plaques were observed in the presence of CD6. The superior inhibitory effect of HF5 was also observed at the lowest concentration of MAb tested: CA/09 plaques were observed at 0.1 μg/ml of either antibody, but plaques formed in the presence of HF5 were slightly smaller than those formed in the presence of CD6 (FIGS. 15B and 15C).

In comparison to HF5 and CD6, inhibition of plaque formation by MAbs 4E9 and 1H5 was poor. There was no reduction in plaque size at 0.1 or 0.5 µg/ml MAb but when the agar overlay was supplemented with ≥1 µg/ml MAb, both 4E9 and 1H5 reduced the size of CA/09 plaques. Compared to the average size of CA/09 plaques formed in the presence of 10 µg/ml of the control antibody 3A2 (2.1 mm), plaques formed in the presence of 4E9 were significantly smaller (p<0.001), with average diameters of 1.6, 1.3, and 1.0 mm at antibody concentrations of 1, 5, and 10 µg/ml, respectively. Similar results were observed with MAb 1H5 (FIGS. 15B and 15C). Thus, the plaque assays revealed that HF5 and CD6 were more effective than 4E9 and 1H5 in inhibiting CA/09 spread. This result is consistent with the ability of each MAb to inhibit NA activity.

Figure 15D:
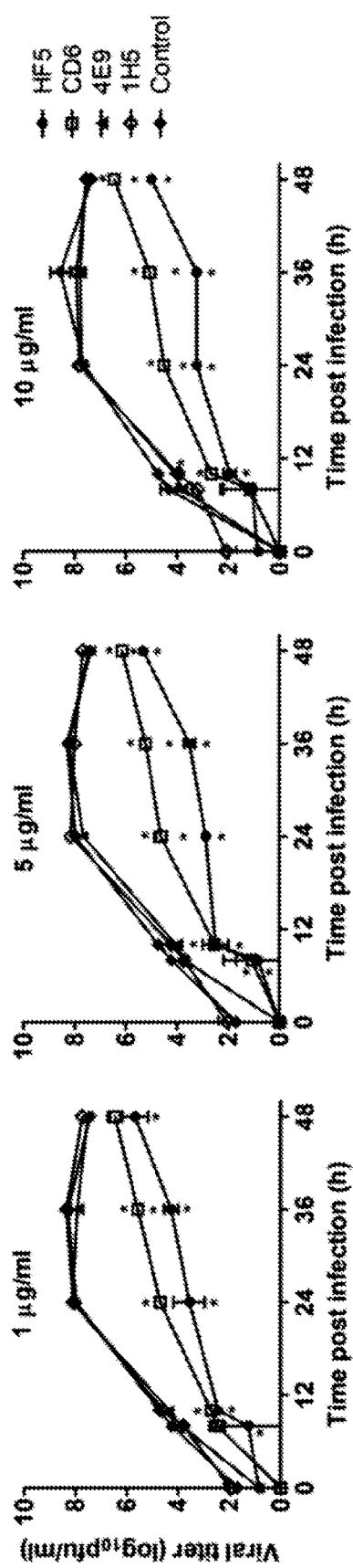

Since the four MAbs inhibited NA activity and virus spread with different efficiency, it was tested whether the inhibitory potential could be extended to multiple cycles of virus replication. MDCK cells were infected with CA/09 at a MOI=0.001 and maintained in media supplemented with each MAb. HF5 and CD6 inhibited the growth of CA/09 at all of the concentrations tested (1, 5 or 10 µg/ml), with viral titers that were lower than those observed with the control antibody 3A2 at each of the examined time points (FIG. 15D). The presence of HF5 and CD6 retarded virus growth: peak viral titers were not attained in the presence of these MAbs until 48 h, when most of the cells had died, whereas peak titers were measured at 36 h in the presence of control MAb 3A2. The peak titers in control culture supernatants were significantly (~100-fold, p<0.01 or 0.001) higher than in supernatants containing HF5 and CD6. The absence of a dose-dependent effect with HF5 and CD6 suggests that maximal inhibition was obtained at the lowest concentration examined, 1 µg/ml. This is consistent with the fact that this concentration is ~20-50 times greater than the $IC_{50}$ of the two antibodies measured by ELLA.

In contrast, mAbs 4E9 and 1H5 did not inhibit virus growth at any of the concentrations tested (except for 10 µg/ml at 10 h p.i.), as reflected by viral titers similar to those detected in the presence of control antibody 3A2. This is also consistent with the fact that these two antibodies failed to effectively inhibit the NA activity of CA/09.

HF5 and CD6 inhibited virus replication to a similar extent at early time points (8 and 10 h). However, viral titers measured in HF5 culture supernatants were all lower than those in CD6 samples at 24, 36 and 48 h (FIG. 15D), suggesting that HF5 was more effective than CD6 in inhibiting multiple cycles of CA/09 replication.

Example 11

HF5 and CD6 are Superior to 4E9 and 1115 in Protecting Mice Against Wt CA/09 when Administered Before Challenge Since the in vitro assays demonstrated that MAbs HF5 and CD6 inhibited CA/09 more efficiently than 4E9 and 1H5, it was investigated whether this corresponds to differences in protection against virus challenge in vivo. CD6 and two N1 broadly-reactive antibodies, 1H5 and 3H10, all protected mice against lethal challenge with a vaccine candidate virus CA/09-X179A (Wan et al., J Virol 87:9290-9300, 2013, and data presented above), although the latter two MAbs required higher doses than CD6 to achieve full protection. It was determined whether similar amounts of antibody would protect mice against a more virulent pH1N1 virus challenge.

CA/09-X179A is a reassortant virus that contains the HA, NA and PB1 genes of CA/09, and the 5 additional gene segments from A/Puerto Rico/8/1934 (PR8) (Robertson et al., Vaccine 29:1836-1843, 2011). The CA/09-X179A stock has titers of $3.2 \times 10^8 EID_{50}$/ml and $1.85 \times 10^5$ $MLD_{50}$/ml (measured with DBA/2 mice) (Table 5), thus ~1,730 $EID_{50}$ of this virus equals 1 $MLD_{50}$.

TABLE 5

Infectious titers and viral particle count of CA/09-X179A and wt CA/09 stocks

| Virus | Titer[a] | | Virus count[b] |
|---|---|---|---|
| | $MLD_{50}$/ml | $EID_{50}$/ml | Viral particles/ml |
| CA/09-X179A | $1.85 \times 10^5$ | $3.2 \times 10^8$ | $7.1 \pm 1.8 \times 10^8$ |
| wt CA/09 | $3.3 \times 10^7$ | $5.9 \times 10^8$ | $9.8 \pm 2.9 \times 10^8$ |

[a]$MLD_{50}$ was measured in DBA/2 mice. Infectious virus titers were determined in 9-12 day old embryonated eggs and are not reported as plaque forming units because the CA/09-X179A virus induced opaque, small plaques in MDCK cells that were difficult to count accurately.
[b]Number of viral particles were counted with Virus Counter 2100 (ViroCyt, Boulder, CO). Shown are the average of three counts that used 1:5, 1:10 and 1:20 dilutions of each viral stock.

By comparison, the wt CA/09 stock has titers of $5.9 \times 10^8 EID_{50}$/ml and $3.3 \times 10^7 MLD_{50}$/ml, therefore ~18 $EID_{50}$ corresponds to 1 $MLD_{50}$. Virus count confirmed that the concentration of viral particles in each stock was similar: $7.1 \pm 1.8 \times 10^8$ and $9.8 \pm 2.9 \times 10^8$ viral particles/ml, respectively, indicating that ~3,900 CA/09-X179A or ~30 CA/09 viral particles equal 1 $MLD_{50}$. These data show that wt CA/09 is more virulent than CA/09-X179A, with ~100-fold less wt CA/09 constituting 1 $MLD_{50}$ in DBA/2 mice. This study tested the efficacy of MAbs HF5, CD6, 4E9 and 1H5 against the more virulent wt CA/09 virus in the DBA/2 mouse model.

Figure 16M:
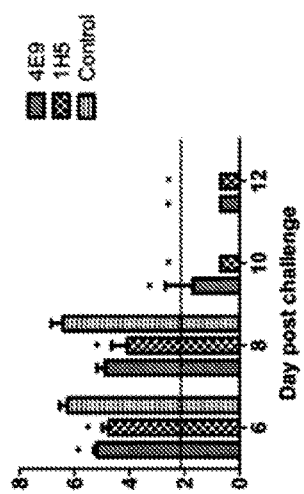
FIGS. 16A-16O. Prophylactic efficacy of MAbs HF5, CD6, 4E9 and 1H5 against lethal pH1N1 virus challenge in mice. DBA/2 mice (n=14 or 20 per group) were treated i.p. with HF5, CD6, 4E9 or 1H5 at indicated doses, followed by challenge i.n. with 10 $MLD_{50}$ CA/09 12 h later. MAb 3A2, which is specific to the NA of seasonal H1N1 virus BR/07, was used as a negative control. Survival (panels 16A, 16D, 16G, 16J and 16M) and weight loss (panels 16B, 16E, 16H, 16K and 16N) (n=8 per group) were monitored for up to 14 days. Lungs were collected on different days and viral titers (panels 16C, 16F, 16I, 16L and 16O) were determined by titrating in MDCK cells. Titers are expressed as $\log_{10}$ $TCID_{50}$/ml (n=3); SD is shown with an error bar. The dotted lines denote the detection limit 2.2 $\log_{10}$ $TCID_{50}$/ml. A titer of 0.7 $\log_{10}$ $TCID_{50}$/ml was arbitrarily assigned to samples below the detection limit. Viral titers of the control groups at day 8 p.c. were used for analysis of titers measured on days 10 and 12 p.c. because none of the mice in control groups survived at these time points. Significant differences between titers measured in each group and MAb 3A2-treated control groups are shown as *, p<0.05.
Figure 16N:
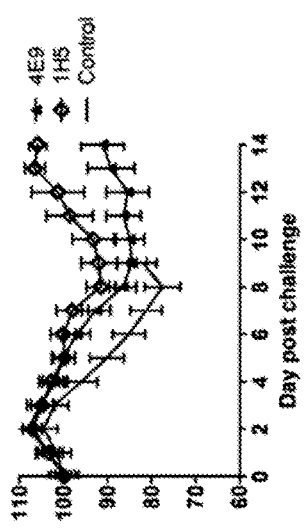

To examine the prophylactic efficacy, various doses of each MAb were administered i.p. to DBA/2 mice 12 h before challenge with 10 $MLD_{50}$ of wt CA/09. The doses of MAb used in this study were guided by results of previous studies with the less virulent virus. HF5 and CD6 were used at doses of 0.2, 1 and 5 mg/kg, while 4E9 and 1H5 were used at doses of 5, 10 and 15 mg/kg. Survival (FIGS. 16A, 16D, 16G, 16J and 16M) and weight loss (FIGS. 16B, 16E, 16H, 16K and 16N) were monitored daily. As shown in FIG. 16, the prophylactic effect of MAbs HF5 and CD6 was dose dependent, with greatest survival at the highest dose. HF5 was more effective than CD6, as either 1 or 5 mg/kg of HF5 resulted in maximum protection (~90% survival), whereas a 5 mg/kg dose of CD6 protected all mice from death, and 1 mg/kg of CD6 resulted in 25% survival. No mice that received 0.2 mg/kg of antibody survived. Consistent with the in vitro observations, higher doses of antibodies 4E9 and 1H5 were needed to protect against lethal wt CA/09 infection. 4E9 did not protect any mice from death at 5 mg/kg, while 1H5 protected ~40% of mice. At 10 and 15 mg/kg, 4E9 resulted in partial protection (~20% and 50%), but was not as effective as 1H5, which protected ~60% and ~80% of mice (FIGS. 16J and 16M). All mice in the control groups (injected with antibody 3A2 at 5 or 15 mg/kg) died or had to be euthanized within 9-10 days p.c. In all groups, mice began to lose weight on day 3 p.c.; however, mice that received 1 or 5 mg/kg of HF5, or 5 mg/kg of CD6, lost less weight than other groups (FIGS. 16B, 16E, 16H, 15K and 16N).

Figure 16O:
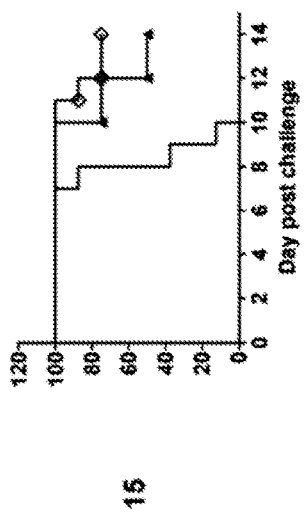

To determine whether MAb treatment reduced viral load in mice, three animals from each group were sacrificed on days 6 and 8 p.c. (and also on days 10, 12 for mice treated with HF5 and CD6 at 5 mg/kg, or with 4E9 and 1H5 at 15 mg/kg), and viral load in the lungs was measured (FIGS. 16C, 16F, 16I, 16L and 16O). High viral titers were detected in all groups of mice on days 6 and 8 p.c. For mice that received the lowest dose of either HF5 or CD6 (0.2 mg/kg), the lung viral titers were similar to those detected in the control group (mice received 5 mg/kg of MAb 3A2). Increasing the HF5 and CD6 doses to 1 or 5 mg/kg resulted in ~10-fold reduction in lung viral titers, except that a more dramatic reduction (~300-fold) was observed on day 8 p.c. in mice that received 5 mg/kg of CD6. As the virus was not cleared by day 8 p.c., additional mice in the 5 mg/kg groups were examined for viral titers on days 10 and 12 p.c. Viral titers were below the detection limit on both days in mice treated with CD6. Virus took longer time to clear from the lungs of mice treated with HF5; there was a ~100-fold reduction in viral titers on day 10 p.c. compared to day 8 p.c., but it was not until day 12 p.c. that the viral load was reduced to below the detection limit (FIG. 16I). For mice that received MAb 4E9 or 1H5, a reduction of viral load was evident in the group given 15 mg/kg antibody; at this dose, virus was cleared by day 12 in mice treated with 4E9, and by day 10 in those treated with 1H5 (FIG. 16O). Taken together, these results indicate that NA antibodies are able to protect mice from challenge with a lethal dose of a more virulent virus, and that the effective dose reflects in vitro functional properties of the MAbs.

To confirm that the differences in protection were not due to differences in absorption of the tested MAbs into the circulatory system, we measured the NI titers in mouse sera after i.p. injection of 5 mg/kg of each MAb. Table 6 demonstrates the MAbs were effectively absorbed into the circulatory system.

TABLE 6

Serum NI titers after passive transfer of N1-specific MAbs

| Day of sera collection[a] | Serum NI titer against homologous viral NA[b] | | | | | |
|---|---|---|---|---|---|---|
| | HF5 | CD6 | 4E9 | 1H5 | 3A2 | PBS |
| 1 | 5120 | 2560 | 5120 | 640 | >5120 | <10 |
| 3 | 2560 | 5120 | 2560 | 640 | >5120 | <10 |
| 6 | 2560 | 1280 | 1280 | 320 | >5120 | <10 |
| 9 | 2560 | 1280 | 640 | 80 | >5120 | <10 |
| 14 | 1280 | 640 | 80 | 40 | >5120 | <10 |

[a]Mouse sera were collected on 1, 3, 6, 9 and 14 days after i.p. injection of each MAb (5 mg/kg) or PBS.
[b]NI titers were measured in ELLA with H6N1 reassortant viruses that contain the HA gene of H6N2 virus A/turkey/Massachusetts/3740/1965 and the NA gene of CA/09 (H6N1$_{CA/09}$) or the NA gene of BR/07 (H6N1$_{BR/07}$) virus. Sera from HF5 and CD6 groups were titrated against H6N1$_{CA/09}$; sera from 4E9, 1H5 and 3A2 groups were titrated against H6N1$_{BR/07}$; sera from the PBS group were titrated against both viruses. Shown are the titers from sera pooled from 3 mice at each time point.

High NI titers were measured against the homologous NA on day 1 after administration of the MAbs. These levels were maintained throughout the testing period for CD6 and HF5, but serum NI titers declined at later time points for mice treated with MAbs 4E9 and 1H5 (8-16 fold reduction compared to titers on day 1). These data confirm that differences in MAb protective efficacy were likely due to differences in functional attributes of the MAbs and not an effect of MAb absorption.

Example 12

11F5 and CD6 Protect Mice Against Lethal CA/09 Challenge when Administered Therapeutically To examine the therapeutic efficacy of these MAbs, DBA/2 mice were infected with 10 MLD$_{50}$ of wt CA/09 before administering each antibody. 4E9 was not included in this study due to its poor effectiveness in the prophylactic study compared to the other three MAbs. After challenge with wt CA/09, each antibody was administered i.p. at doses of 5 (HF5 and CD6) or 10 mg/kg (1H5) once (on day 1 p.c.), twice (on days 1 and 5 p.c.), or three times (on days 1, 2 and 3 p.c.). As shown in FIG. 17 (see FIGS. 17A, 17D, 17G), all treatments with HF5 protected ≥75% of the challenged mice from death. For antibody CD6, 50% of mice that received two or three doses survived the challenge, while a single 5 mg/kg dose only protected 25% of the mice. Administration of 1H5 did not result in significant protection; only 1 out of the 8 mice that received three 10 mg/kg doses of this antibody survived.

Mice in all groups began to lose weight on day 3 p.c. (FIGS. 17B, 17E and 17H), and the surviving mice began gaining weight by days 9 to 11 p.c. The HF5 treated mice generally lost less weight than the CD6 treated ones: the maximum weight loss observed in HF5 treated mice was ~17%, while the maximum weight loss observed in CD6 treated mice was 24% (FIG. 17B).

Similar to the observation in prophylactic study, high viral titers were measured in the lungs of mice on days 6 and 8 p.c. in all groups, although the titers in lungs of mice that received HF5 or CD6 were slightly lower than in the control group (mice received antibody 3A2) (see FIGS. 17C, 17F and 17I). To further investigate virus clearance in mice treated with each MAb, we measured viral load at later time points in lungs of mice that received three doses (on days 1, 3 and 5 p.c.) of HF5 or CD6. By day 10, virus was cleared in mice that received HF5, while virus in CD6 treated mice did not clear until day 12 p.c.

Example 13

HF5 Selects Escape Mutants In Vivo

Figure 18A:
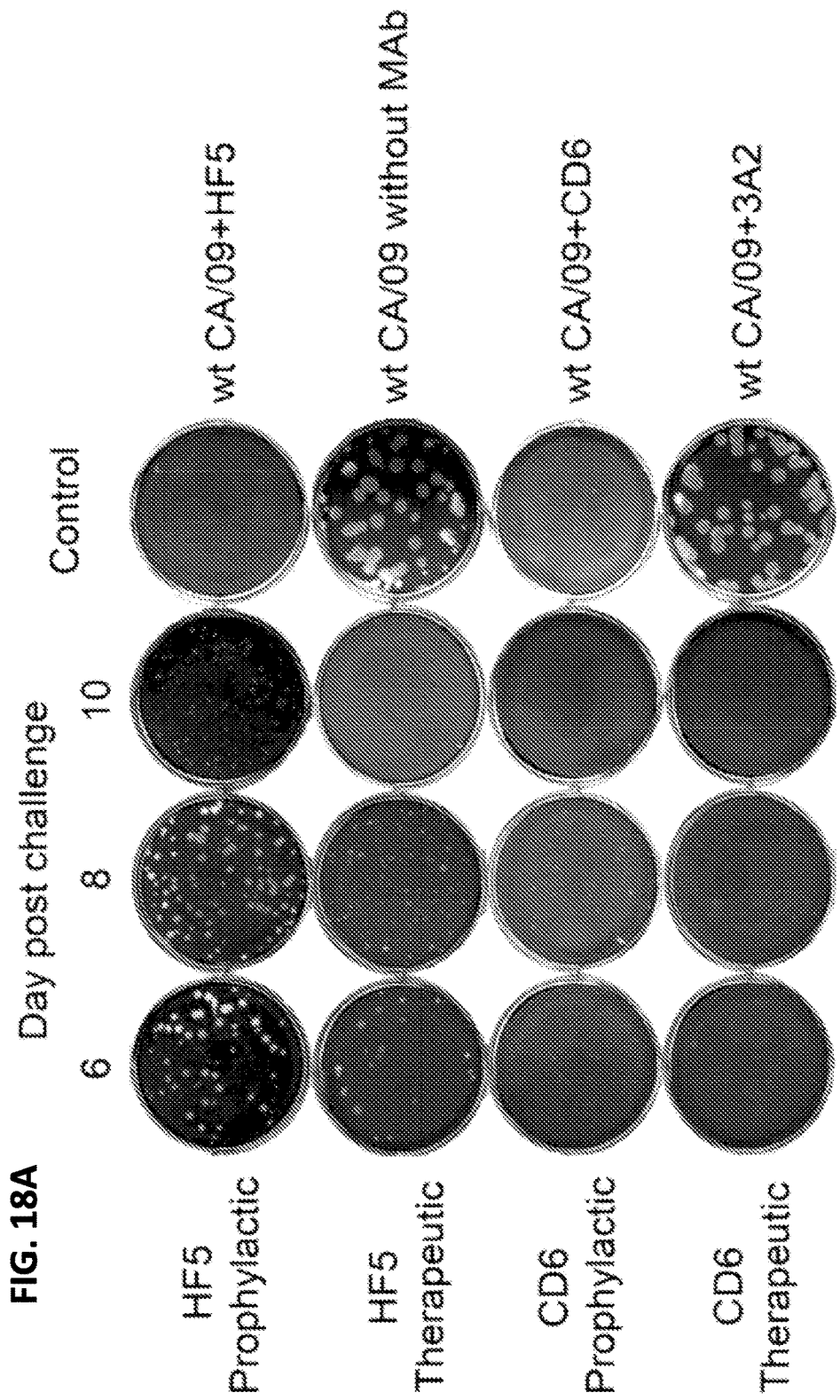
FIGS. 18A-18D. MAb HF5 selected escape mutants of pH1N1 virus in mice. (18A) Lung samples from mice collected on days 6, 8 and 10 p.c. in aforementioned prophylactic (5 mg/kg of MAb before CA/09 challenge) and therapeutic (three doses of 5 mg/kg MAb after CA/09 challenge) studies were homogenized and the supernatant was tested in plaque assay, in which MAb HF5 or CD6 was supplemented in the agar overlay. (18B) and (18C) Enzyme activity of CA/09 escape variants selected with HF5: the NA activity of CA/09 variants with S364N or N397K mutations in the NA were compared with that of the wt parent virus in (18B) MU-NANA assay that uses a small substrate and (18C) ELLA that uses a large substrate, fetuin. The three viruses were adjusted to contain the same number of viral particles per ml and tested in duplicate. Relative fluorescence units (RFUs) and OD values generated with mutants are expressed as a percentage of the signals obtained with the wt CA/09. (18D) CA/09 mutants with S364N mutation (left panel) or N397K mutation (middle panel) in the NA were examined for their NA sensitivity to MAbs HF5, CD6 and 3A2 in ELLA. wt CA/09 (right panel) was included for comparison.

To further evaluate the potential of MAbs HF5 and CD6 as prophylactic and therapeutic agents, these two MAbs were examined to see if they selected escape mutants of CA/09 in vivo. Mouse lungs collected on days 6, 8 and 10 p.c. from the prophylactic (administration of 5 mg/kg of antibody 12 h before challenge with wt CA/09) and therapeutic (three doses administered at 5 mg/kg on days 1, 2 and 3 p.c. following challenge with wt CA/09) studies were tested for the presence of escape mutants. This was examined by isolating viral plaques from supernatants of lung homogenates with MAb (2 µg/ml) in the agar overlay. Despite the presence of antibody HF5 in the agar overlay, clear, big plaques were observed with lung samples from mice treated with HF5 either prophylactically or therapeutically (FIG. 18A), indicating that escape mutants of CA/09 had emerged in both treatments. However, in the presence of CD6, no plaques that were bigger than those of wt CA/09 were observed with lung supernatants from CD6 treated mice, demonstrating the absence of escape mutants that are resistant to the inhibition by CD6. HF5-selected mutant viruses were expanded by picking plaques and culturing in eggs. Sequencing of the mutant viruses revealed S364N or N397K mutation in the NA of viruses selected in the prophylactic treatment, and S364N mutation in the NA of mutant viruses from the therapeutic treatment. wt CA/09 virus that was used for challenge (egg passage 6/MDCK passage 1) was grown in eggs for the same amount of time (48 h) as virus plaques isolated from the lungs of MAb-treated mice; no NA sequence change was detected in the resultant virus (egg passage 7/MDCK passage 1), confirming that the mutations observed in the NA of HF5 escape mutants were not the result of passaging the virus in eggs.

Figure 18C:
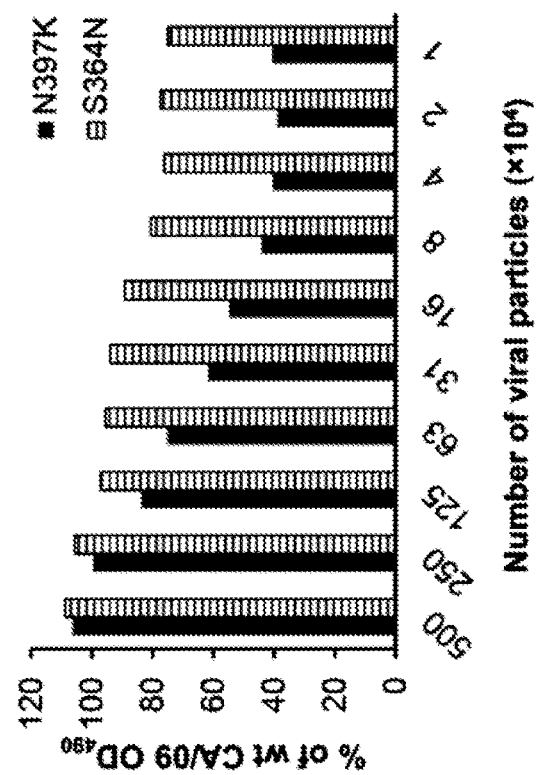
Figure 18B:
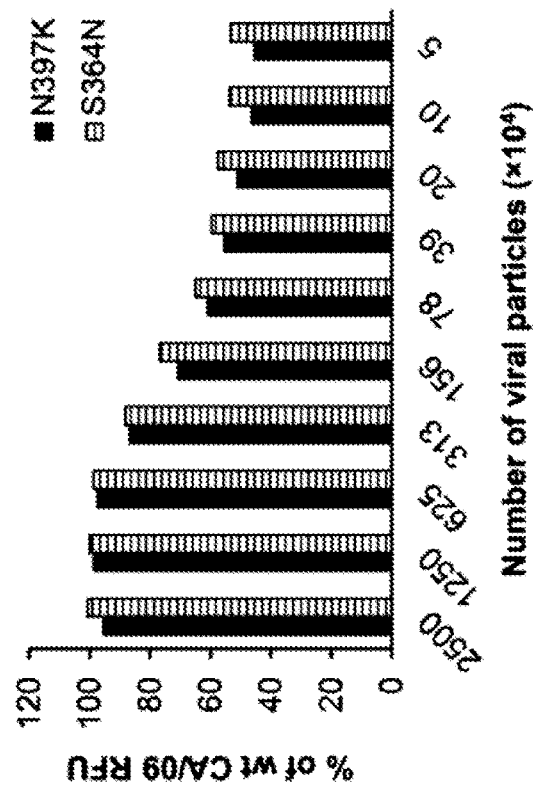
Figure 18D:
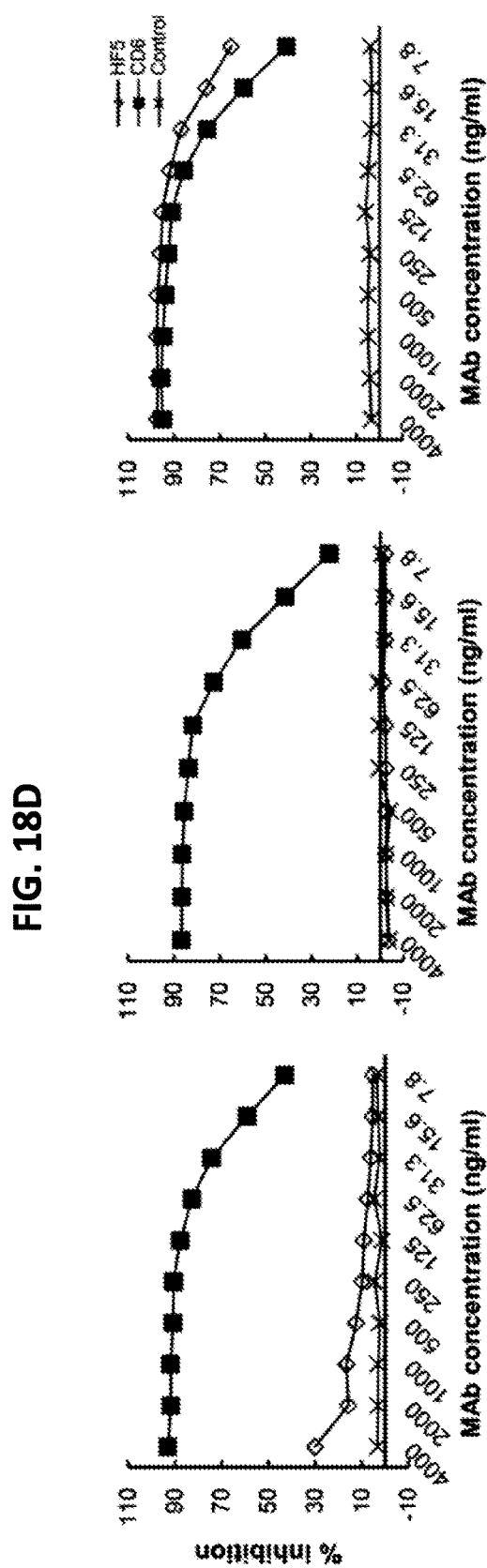

The NA activity of the mutant viruses, especially the virus with N397K mutation in the NA, was less than that of wt CA/09 when measured using either a small substrate MU-NANA (FIG. 18B) or large substrate fetuin (FIG. 18C). NI assays were performed to confirm the resistance of mutant viruses (with S364N and N397K in the NA, respectively) to antibody HF5; while HF5 effectively inhibited wt CA/09 NA, it failed to inhibit either mutant virus (FIG. 18D). This is consistent with the observation in cell-based ELISA, which indicates that S364N and N397K mutations result in a dramatic reduction in the binding of HF5 to NA (FIG. 14A). As shown in FIG. 18D, both of the mutant viruses retain sensitivity to inhibition by CD6.

Thus, the in vitro properties of four NA-specific MAbs, HF5, CD6, 4E9 and 1H5, and test the efficacy of these MAbs in vivo against wt pH1N1 virus CA/09. It is clear that the epitopes recognized by HF5, CD6 and group B MAbs (e.g., 4E9 and 1H5) are different from each other, although we cannot exclude that these epitopes may overlap to some extent. The CD6 epitope and the epitope recognized by group B MAbs are located relatively lateral in the NA head in relation to the enzyme active site (see above). Residues 364, 369 and 397, identified in the present study to be critical for the binding by MAb HF5, are located in a region of a polypeptide chain which encircles the enzyme active site pocket. Therefore, the HF5 epitope is likely at closer proximity to the NA active center than epitopes recognized by CD6 as well as 4E9 and 1H5.

The in vitro properties of these NA MAbs correspond to the relative distance of the epitopes to the NA active center. For instance, in the lectin-based NI assay, HF5 inhibited CA/09 NA more efficiently than did the other three MAbs. HF5 also inhibited plaque formation and the growth kinetics of CA/09 virus to a greater extent than CD6 and the group B antibodies. HF5 exhibited higher efficacy than 4E9 and 1H5, and even CD6, in protecting mice from lethal challenge with CA/09. These findings indicated that for NA MAbs, the in vitro properties (reduction in plaque size, inhibition of virus growth in cell culture and inhibition of NA activity as measured with ELLA) are generally consistent with each other, and correlate with the in vivo effectiveness in protecting against influenza virus.

When administered at effective doses (e.g., ≥1 mg/kg prophylactically or 5 mg/kg therapeutically), HF5 appeared to be a suitable treatment. However, it rapidly selected escape mutants of CA/09 virus in vivo, which diminishes its potential to serve as a therapeutic against pH1N1 virus infection. In fact, the N397K mutation, detected in the NA of escape mutants from the HF5 treated mice, has occurred in the current circulating pH1N1 viruses (Takashita et al., Euro Surveill 19, November to December 2013; Takashita et al., Antimicrob Agents Chemother 59:2607-2617). In addition, the N369K mutation, which abolishes the binding of HF5 to CA/09 NA, was selected soon after the introduction of pH1N1 virus into the human population and by 2011 was present in ≥99% of the circulating strains (Hurt et al., J Infect Dis 206:148-157, 2012). This suggests that the HF5 epitope is probably also targeted by the human NA-specific antibodies, which resulted in antigenic drift of this epitope. The prevalence of N369K, and to a lesser extent, N397K mutations in circulating pH1N1 viruses (Okomo-Adhiambo et al., Emerg Infect Dis 21:136-141, 2015) indicate that antibodies elicited against the HF5 epitope in humans no longer bind to the majority of circulating pH1N1 viruses.

Thus, although MAb HF5 is more effective in inhibiting NA of the prototype pH1N1 virus CA/09, it is not a suitable candidate for further development as a therapeutic.

It was interesting to find that mutant viruses with S364N and N397K, but not N369K mutation in the NA, were selected by MAb HF5 in mice. This phenomenon was also noted for N9-specific MAb NC41: when MAbs that bind N9 were used to select escape variants, mutations at residue 369 were selected by some MAbs, but not by NC41, even though x-ray crystallography shows that both heavy and light chains of the antibody have contact with amino acid 369 (Air et al., J Virol 64:5797-5803, 1990). It is likely that the amino acid changes selected are unique to each antibody. In addition, the selective pressure exerted by human immune response (elicited by either natural infection or vaccination) might be different from that by mouse MAb HF5, which may result in different amino acid mutations in the NA. However, the reasons for selecting specific mutations are likely to be complex and as these examples show, are sometimes not easily predicted.

In contrast to various mutations within the HF5 epitope that are observed in the NA of circulating pH1N1 viruses, phylogenetic analysis shows that the CD6 epitope has remained largely conserved. The N449D/D451G double mutation in CA/09 NA, which was selected in vitro (Wan et al., Nat Commun 6:6114, 2015), has not been identified in natural pH1N1 viruses so far, highlighting the potential of antibody CD6 to serve as an ideal target for antiviral development. It is noteworthy that the D to G mutation at residue 451, one of the important contacts in the CD6 epitope, has been detected in some circulating pH1N1 strains. However, it does not appear to affect the inhibition by CD6, as additional amino acid mutations in the NA may help these strains to retain the sensitivity to CD6 (see above). Taken these into consideration, antibody CD6 is more ideal than HF5 for serving as an antiviral, even though it is slightly less effective than HF5 in inhibiting CA/09 NA activity.

MAb CD6 protected all mice after a single dose of 1 mg/kg administered prophylactically or a single dose of 5 mg/kg administered therapeutically. High doses (15 mg/kg) of the broadly-reactive group B MAbs 1H5 and 3H10 also provided full protection against lethal challenge with this virus. In the present study, however, group B MAb 4E9 failed to result in similar protective efficacy against the wt CA/09, and a higher dose of CD6 was needed to obtain optimal protection. These data reflect a difference in virulence of wt CA/09 and CA/09-X179A in the DBA/2 mouse model. The more stringent conditions imposed by using the more virulent virus in the mouse model is an important step toward development of antivirals.

Antibodies vary in their properties, including specificity, affinity and the ability to neutralize/inhibit virus. The efficacy of NA-specific MAbs is largely due to reduced release of newly formed virus particles from infected cells although clearance of virus-infected cells through complement or antibody-dependent cytotoxicity mechanisms may also contribute to their effectiveness. The results disclosed herein suggest that the rate at which virus replication is reduced by NA-specific MAbs could depend on the virus strain. At high doses (≥2.5 mg/kg), prophylactic treatment with MAb CD6 cleared CA/09-X179A vaccine virus from the lungs of mice by day 3 p.c., however the same MAb applied at a higher dose (5 mg/kg) did not result in clearance of the more virulent wt CA/09 until after day 10 p.c. Regardless of initial effectiveness, antibodies that select escape variants may quickly become obsolete as antigenic drift variants become predominant in the circulating virus population. NA antibodies such as CD6 that bind to conserved antigenic domains and also have inhibitory properties are more likely to be effective against a broad range of circulating viruses and are less likely to select escape variants. A mixture of MAbs with specificity for different NA epitopes, or a mixture of NA- and HA-specific MAbs, can be used in combination to further minimize the generation of escape mutants and improve treatment.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

---

We claim:

1. An isolated monoclonal antibody or antigen binding fragment thereof comprising a heavy chain variable domain and a light chain variable domain,
wherein the heavy chain variable domain comprises a heavy chain complementarity determining region (HCDR)1, an HCDR2 and an HCDR3, and wherein and wherein the light chain variable domain comprises a light chain complementarity determining region (LCDR)1, an LCDR2 and an LCDR3,
wherein the heavy chain variable comprises the HCDR1, HCDR2 and HCDR3 of SEQ ID NO: 1,
wherein the light chain variable domain comprises the LCDR1, LCDR2 and LCDR3 of SEQ ID NO:2, and wherein the HCDR1, HCDR2, HCDR3, HCDR3, LCDR1, LCDR2 and LCDR3 are all determined using the same method according to Kabat, Chothia, or IMGT,
and wherein the monoclonal antibody specifically binds neuraminidase of an N1 subtype influenza virus.

2. The isolated monoclonal antibody or antigen binding fragment of claim 1, wherein the HCDR1 comprises the amino acid sequence set forth as amino acids 26 to 33 of SEQ ID NO: 1, the HCDR2 comprises the amino acid sequence set forth as amino acids 51 to 60 of SEQ ID NO: 1, and the HCDR3 comprises the amino acid sequence set forth as amino acids 99 to 113 of SEQ ID NO: 1, and wherein the LCDR1 comprises the amino acid sequence set forth as amino acids 27 to 31 of SEQ ID NO: 2, the LCDR2 comprises the amino acid sequence set forth as amino acids 49 to 51 of SEQ ID NO:2, and the LCDR3 comprises the amino acid sequence set forth as amino acids 88 to 96 of SEQ ID NO: 2.

3. The isolated monoclonal antibody or antigen binding fragment of claim 2, wherein the heavy chain variable domain comprises a serine (S) at amino acid 25, an aspartic acid (D) at amino acid 76, a serine (S) at amino acid 77, and a serine (S) at amino acid 79.

4. The isolated monoclonal antibody or antigen binding fragment of claim 2, wherein the heavy chain variable domain comprises a serine (S) at amino acid 25, a glycine (G) at amino acid 26, a phenylalanine (F) at amino acid 27, a threonine (T) at amino acid 28, a phenylalanine (F) at amino acid 29, an asparagine (N) at amino acid 30, a threonine (T) at amino acid 31, a tyrosine (Y) at amino acid 32, a serine (S) at amino acid 55, an aspartic acid (D) at amino acid 76, a serine (S) at amino acid 77, a serine (S) at amino acid 79, an arginine (R) at amino acid 100, an isoleucine (I) at amino acid 103, a tyrosine (Y) at amino acid 104, a tyrosine (Y) at amino acid 105, and a tyrosine (Y) at amino acid 106.

5. The isolated monoclonal antibody or antigen binding fragment of claim 2, wherein the light chain variable domain comprises a tyrosine (Y) at amino acid 48, an asparagine (N) at amino acid 52, a leucine (L) at amino acid 53, a serine (S) at amino acid 55, a valine (V) at amino acid 57, an phenylalanine (F) at amino acid 59, and a serine (S) at amino acid 62.

6. The isolated monoclonal antibody or antigen binding fragment of claim 2, wherein the light chain variable domain comprises a tyrosine (Y) at amino acid 48, an alanine (A) at amino acid 49, a serine (S) at amino acid 51, an asparagine (N) at amino acid 52, a leucine (L) at amino acid 53, a serine (S) at amino acid 55, a valine (V) at amino acid 57, a phenylalanine (F) at amino acid 59, and a serine (S) at amino acid 62.

7. The isolated monoclonal antibody or antigen binding fragment of claim 1, wherein the heavy chain variable domain comprises the amino acid sequence set forth as SEQ ID NO: 1.

8. The isolated monoclonal antibody or antigen binding fragment of claim 1, wherein the light chain variable domain comprises the amino acid sequence set forth as SEQ ID NO: 2.

9. The isolated monoclonal antibody of claim 1, wherein the antibody is an IgG, IgM or IgA.

10. The isolated monoclonal antibody or antigen binding fragment of claim 1, wherein the monoclonal antibody or antigen binding fragment is humanized or chimeric.

11. The isolated monoclonal antibody or antigen binding fragment of claim 1, wherein the monoclonal antibody or antigen binding fragment specifically binds the neuraminidase of influenza virus A(H1N1)pdm09.

12. The isolated antigen binding fragment of the isolated monoclonal antibody of claim 1.

13. The isolated antigen binding fragment of claim 12, wherein the fragment is a Fab fragment, a Fab' fragment, a F(ab)'2 fragment, a single chain Fv protein (scFv), or a disulfide stabilized Fv protein (dsFv).

14. The isolated antigen binding fragment of claim 13, wherein the fragment is the F(ab)'2 fragment.

15. The isolated monoclonal antibody or antigen binding fragment of claim 1, wherein the antibody or antigen binding fragment is labeled.

16. The isolated monoclonal antibody or antigen binding fragment of claim 15, wherein the label is a fluorescent, an enzymatic, or a radioactive label.

17. A composition comprising an effective amount of the monoclonal antibody or antigen binding fragment of claim 1, and a pharmaceutically acceptable carrier.

18. The composition of claim 17, further comprising a second monoclonal antibody or antigen binding fragment thereof that specifically binds a second influenza virus protein.

19. The composition of claim 18, wherein the second influenza virus protein is a neuraminidase.

20. The composition of claim 19, wherein the second monoclonal antibody or antigen binding fragment binds a different epitope of neuraminidase, or wherein the second influenza virus protein is a hemagglutinin.

21. The composition of claim 20, wherein the second influenza virus protein is an H1N1 influenza virus protein, an H5N1 influenza virus protein, an H2N2 influenza virus protein, an H3N2 influenza virus protein, or an H7N9 influenza virus protein.

22. An isolated nucleic acid molecule encoding the monoclonal antibody or antigen binding fragment of claim 1.

23. The isolated nucleic acid molecule of claim 22, operably linked to a promoter.

24. An expression vector comprising the isolated nucleic acid molecule of claim 23.

25. An isolated host cell transformed with the expression vector of claim 24.

26. A method for inhibiting and/or treating an influenza infection in a subject, comprising:
    administering to the subject a therapeutically effective amount of the antibody or antigen binding fragment of claim 1, a nucleic acid molecule encoding the antibody or the antigen binding fragment, or a vector including the nucleic acid molecule,
    thereby inhibiting and/or treating the influenza virus infection in the subject.

27. The method of claim 26, further comprising:
    administering to the subject a therapeutically effective amount of an anti-viral agent.

28. The method of claim 27, wherein the anti-viral agent is human intravenous immunoglobulin, oseltamivir, zanamivir, peramivir, amantadine or rimantadine.

29. A method of detecting an influenza virus infection in a subject comprising:
    contacting a biological sample from the subject with the monoclonal antibody or antigen binding fragment of claim 1; and
    detecting antibody bound to the sample,
    wherein the presence of antibody bound to the sample indicates that the subject has an influenza virus infection.

30. The method of claim 29, wherein the monoclonal antibody or antigen binding fragment is directly labeled.

31. The method of claim 29, further comprising:
    contacting the sample with a second antibody that specifically binds the isolated monoclonal antibody or antigen binding fragment; and
    detecting the binding of the second antibody,
    wherein an increase in binding of the second antibody to the sample as compared to binding of the second antibody to a control sample detects the presence of an influenza virus infection the subject.

32. The method of claim 31, wherein the biological sample is a nasal wash, a lung aspirate, a throat swab, a sputum sample or a saliva sample.

33. A method of identifying a protein as a vaccine candidate, comprising:
    contacting the protein with the monoclonal antibody or antigen binding fragment of claim 1 under conditions sufficient to form an immune complex; and
    detecting the presence of an immune complex,
    wherein the presence of the immune complex indicates that the protein is a vaccine candidate for an influenza virus infection.

34. The method of claim 33, wherein the monoclonal antibody or antigen binding fragment is directly labeled.

35. The method of claim 33, further comprising:
    contacting the immune complex with a second antibody that specifically binds the isolated monoclonal antibody or antigen binding fragment; and
    detecting the binding of the second antibody to the immune complex,
    wherein binding of the second antibody to the immune complex indicates that the protein is a vaccine candidate for an influenza virus infection.

36. A method for determining the quantity of neuraminidase in a sample, comprising:
    contacting a sample with the monoclonal antibody or antigen binding fragment of claim 1 under conditions sufficient to form an immune complex; and
    quantifying the amount of the immune complex, thereby determining the quantity of neuraminidase in the sample.

37. The method of claim 36, wherein the monoclonal antibody or antigen binding fragment is directly labeled.

38. The method of claim 36, wherein quantifying the amount of the immune complex comprises:
    contacting the sample with a second antibody that specifically binds the monoclonal antibody or antigen binding fragment; and
    quantifying binding of the second antibody to the immune complex,
    wherein the quantity of the second antibody bound to the immune complex quantifies the amount of neuraminidase present in the sample.

39. A method for determining the potency of a neuraminidase inhibitor, comprising:
    performing an enzyme linked immunosorbant assay (ELISA) or enzyme linked lectin assay (ELLA) using the neuraminidase inhibitor,
    wherein the monoclonal antibody or antigen binding fragment of claim 1 is used as a positive control or reference standard in the ELISA or ELLA.

* * * * *

UNITED STATES PATENT AND TRADEMARK OFFICE
CERTIFICATE OF CORRECTION

PATENT NO.       : 10,072,070 B2
APPLICATION NO.  : 15/532059
DATED            : September 11, 2018
INVENTOR(S)      : Wan et al.

Page 1 of 1

It is certified that error appears in the above-identified patent and that said Letters Patent is hereby corrected as shown below:

In the Claims

Column 83, Lines 15-16, in Claim 1 "(HCDR)1, an HCDR2 and an HCDR3, and wherein and wherein the light chain variable domain comprises," should read --(HCDR)1, an HCDR2 and an HCDR3, and wherein the light chain variable domain comprises--.

Signed and Sealed this
Thirty-first Day of December, 2019

Andrei Iancu
*Director of the United States Patent and Trademark Office*